US012027236B2

(12) United States Patent
Aiden et al.

(10) Patent No.: US 12,027,236 B2
(45) Date of Patent: Jul. 2, 2024

(54) LINEAR GENOME ASSEMBLY FROM THREE DIMENSIONAL GENOME STRUCTURE

(71) Applicants: THE BROAD INSTITUTE, INC., Cambridge, MA (US); BAYLOR COLLEGE OF MEDICINE, Houston, TX (US)

(72) Inventors: Erez Aiden, Houston, TX (US); Olga Dudchenko, Houston, TX (US); Eric Lander, Cambridge, MA (US)

(73) Assignees: THE BROAD INSTITUTE, INC., Cambridge, MA (US); BAYLOR COLLEGE OF MEDICINE, Houston, TX (US)

( * ) Notice: Subject to any disclaimer, the term of this patent is extended or adjusted under 35 U.S.C. 154(b) by 993 days.

(21) Appl. No.: 16/247,502

(22) Filed: Jan. 14, 2019

(65) Prior Publication Data

US 2019/0279740 A1 Sep. 12, 2019

Related U.S. Application Data

(60) Provisional application No. 62/617,289, filed on Jan. 14, 2018.

(51) Int. Cl.
| | |
|---|---|
| *G01N 33/48* | (2006.01) |
| *G16B 30/10* | (2019.01) |
| *G16B 30/20* | (2019.01) |
| *G16B 40/00* | (2019.01) |
| *G16B 45/00* | (2019.01) |
| *G16B 50/00* | (2019.01) |

(52) U.S. Cl.
CPC ............ *G16B 30/10* (2019.02); *G16B 30/20* (2019.02); *G16B 40/00* (2019.02); *G16B 45/00* (2019.02); *G16B 50/00* (2019.02)

(58) Field of Classification Search
None
See application file for complete search history.

(56) References Cited

FOREIGN PATENT DOCUMENTS

WO 2016089920 A1 6/2016

OTHER PUBLICATIONS

Marie-Nelly, Hervé, et al. "High-quality genome (re) assembly using chromosomal contact data." Nature communications 5.1 (2014): 1-10.*
Silva, Genivaldo GZ, et al. "Combining de novo and reference-guided assembly with scaffold_builder." Source code for biology and medicine 8.1 (2013): 1-5.*
Harmon, A., "Team of Rival Scientists Comes Together to Fight Zika", N. Y. Times, Mar. 30, 2016.
Gnerre, Sante et al. "High-quality draft assemblies of mammalian genomes from massively parallel sequence data", Proc. Natl. Acad. Sci., vol. 108, No. 4, pp. 1513-1518, Jan. 25, 2011.
Williams, Louise et al., "Paired-end sequencing of Fosmid libraries by Illumina", Genome Res., vol. 22, pp. 2241-2249, 2012.
Aiden, Erez et al., "Comprehensive mapping of long range interactions reveals folding principles of the human genome", Science, vol. 326, Issue 5950, pp. 289-293, Oct. 9, 2009.
Rao, Suhas et al., "A three-dimensional map of the human genome at kilobase resolution reveals principles of chromatin looping", Cell., vol. 159, pp. 1665-1680, Published online: Dec. 11, 2014.
Kaplan, Noam et al., "High-throughput genome scaffolding from in-vivo DNA interaction frequency", Nat Biotechnol., vol. 31, pp. 1143-1147, pp. 1-10, Dec. 2013.
Marie-Nelly, H. et al., "High-quality genome (re)assembly using chromosomal contact data", Nat. Commun., vol. 5, Issue 5695, Published: Dec. 17, 2014.
Peichel, C.L. et al., "Improvement of the Threespine Stickleback Genome Using a Hi-C-Based Proximity-Guided Assembly", bioRxiv, 068528, pp. 1-21 (2016).
Putnam, N. H. et al., "Chromosome-scale shotgun assembly using an in vitro method for long-range linkage", Genome Res., vol. 26, pp. 342-350, ePublished Feb. 4, 2016.
Burton, J. N. et al., "Chromosome-scale scaffolding of de novo genome assemblies based on chromatin interactions", Nat. Biotechnol, vol. 31, pp. 1119-1125, ePublished: Jul. 31, 2014.
Bickhart, D. M. et al., "Single-molecule sequencing and conformational capture enable de novo mammalian reference genomes", bioRxiv, 064352, posted online: Jul. 18, 2016.
Session, A. M. et al., "Genome evolution in the allotetraploid frog *Xenopus laevis*", Nature, pp. 538, pp. 336-343, Published: Oct. 20, 2016.
Love, R. R. et al., "Evaluation of DISCOVAR de novo using a mosquito sample for cost-effective short-read genome assembly", BMC Genomics, vol. 17, Issue 187, pp. 1-10, Mar. 5, 2016.
Lander, E.S. et al., "Initial sequencing and analysis of the human genome", Nature, vol. 409, pp. 860-921, Feb. 15, 2001.
Venter, J. C. et al., "The Sequence of the Human Genome", Science, vol. 291, pp. 1304-1351, Feb. 16, 2001.
Pendleton, M. et al., "Assembly and diploid architecture of an individual human genome via single-molecule technologies", Nat. Methods, vol. 12, pp. 780-786, Aug. 2015.
Jaffe, D. B. et al., "Whole-genome sequence assembly for mammalian genomes: Arachne 2", Genome Res., vol. 13, pp. 91-96, Jan. 2003.

(Continued)

*Primary Examiner* — Anna Skibinsky
(74) *Attorney, Agent, or Firm* — F. Brent Nix, Esq.; Johnson, Marcou, Isaacs & Nix, LLC

(57) ABSTRACT

Provided herein includes a method for generating an error-corrected genome assembly for an organism comprising: generating a genomic contact map derived from a DNA proximity ligation assay conducted on one or more samples from the organism or a closely related species; superimposing a reference assembled genome derived from whole genome sequencing of one or more samples from the organism on top of the genomic contact map using computer software; correcting errors in the reference assembled genome through a computer user interface to obtain a corrected assembly file, wherein errors in the reference assembled genome are visualized by observing aberrant contacts in the genomic contact map; and applying the corrected assembly file to the reference assembled genome.

9 Claims, 69 Drawing Sheets

(56) References Cited

OTHER PUBLICATIONS

Nene, V. et al., "Genome sequence of Aedes aegypti, a major arbovirus vector", Science, vol. 316, pp. 1718-1723, Published: Jun. 22, 2007.
Juneja, P. et al., "Assembly of the genome of the disease vector Aedes aegypti onto a genetic linkage map allows mapping of genes affecting disease transmission", PLoS Negl. Trop, Dis. 8, e2652, pp. 1-11, Jan. 30, 2014.
Arensburger, P. et al., "Sequencing of Culex quinquefasciatus establishes a platform for mosquito comparative genomics", Science, vol. 330, pp. 1-5, Oct. 1, 2010.
Hickner, P.V. et al., "Composite linkage map and enhanced genome map for Culex pipiens complex mosquitoes", J. Hered., vol. 104, Issue 5, pp. 649-655, Advance Access Publication: Jul. 11, 2013.
Durand, N. C. et al., "Juicer Provides a One-Click System for Analyzing Loop-Resolution Hi-C Experiments", Cell Syst., vol. 3, pp. 95-98, Jul. 2016.
Durand, N. C. et al., "Juicebox Provides a Visualization System for Hi-C Contact Maps with Unlimited Zoom", Cell Syst., vol. 3, pp. 99-101, Jul. 2016.
Hübner, M. R. et al., "Chromatin Dynamics", Annu. Rev. Biophys., vol. 39, pp. 471-489 Jun. 9, 2010.
Ferguson-Smith, M. A. et al. "Mammalian karyotype evolution", Nat. Rev. Genet., vol. 8, pp. 950-962, Dec. 2007.
Sanborn, A. L. et al., "Chromatin extrusion explains key features of loop and domain formation in wild-type and engineered genomes", Proc. Natl. Acad. Sci vol. 112, pp. E6456-E6465, Published online: Oct. 23, 2015.
Tange, O., "GNU Parallel: The Command-Line Power Tool", ;Login: USENIX, vol. 36, pp. 42-47, Feb. 2011.
Harris, Robert S, "Improved Pairwise Alignment of Genomic DNA", A Thesis in Computer Science and Engineering, The Pennsylvania State University, College of Engineering, pp. 1-74, Dec. 2007.
Kruskal, J. B., "On the Shortest Spanning Subtree of a Graph and the Traveling Salesman Problem", Proc. Am. Math. Soc., vol. 7, pp. 48-50 (Feb. 1956).
Vinson, J. P. et al., "Assembly of polymorphic genomes: algorithms and application to Ciona savignyi", Genome Res., vol. 15, pp. 1127-1135, Aug. 2005.
Chin, C.S. et al., "Phased Diploid Genome Assembly with Single Molecule Real-Time Sequencing", Nat. Methods., vol. 13, No. 12, pp. 1050-1056, Dec. 2016.
Darrow, E. M. et al., "Deletion of DXZ4 on the human inactive X chromosome alters higher-order genome architecture", Proc. Natl. Acad. Sci., vol. 113, pp. E4504-E4512, Jul. 18, 2016.
Weisenfeld, N. I. et al., "Comprehensive variation discovery in single human genomes", Nat. Genet., vol. 46, pp. 1350-1355, Dec. 2014.
Li, H. et al., "Fast and accurate short read alignment with Burrows-Wheeler transform", Bioinformatics, vol. 25, Issue 14, pp. 1754-1760, Jul. 15, 2009.
Cao, H. et al., "Rapid detection of structural variation in a human genome using nanochannel-based genome mapping technology", GigaScience. vol. 3:34, Dec. 30, 2014.
Timoshevskiy, V. A. et al., "Genomic composition and evolution of Aedes aegypti chromosomes revealed by the analysis of physically mapped supercontigs", BMC Biol., vol. 12, Issue 27, Published: Apr. 14, 2014.
Unger, M. F. et al., "A standard cytogenetic map of Culex quinquefasciatus polytene chromosomes in application for fine-scale physical mapping", Parasit. Vectors, vol. 8, Issue 307, Jun. 6, 2015.
Naumenko, A. N. et al., "Correction: Mitotic-Chromosome-Based Physical Mapping of the Culex quinquefasciatus Genome", PloS One, vol. 10, e0127565, pp. 1-3, May 8, 2015.
Giraldo-Calderón, G. I. et al., "VectorBase: an updated bioinformatics resource for invertebrate vectors and other organisms related with human diseases", Nucleic Acids Res., vol. 43, pp. D707-713, Published online: Dec. 15, 2014.
Yates, A. et al., "Ensembl 2016", Nucleic Acids Res., vol. 44, pp. D710-D716, Published online: Dec. 19, 2015.
Varoquaux, N. et al., "Accurate identification of centromere locations in yeast genomes using Hi-C", Nucleic Acids Res., vol. 43, Issue 11, pp. 5331-5339, Published online: May 4, 2015.

\* cited by examiner

Aedes aegypti assembly AaegL2

Assisted assembly of the Squirrel monkey genome from the common marmoset genome and comparison to a de novo assembly of the same species Reference-assisted assembly of 3 zebra genomes from a horse genome Meta Hi-C maps can be used to assemble all members of the community at the same time A meta Hi-C map of a cow blood-fed mosquito and a meta Hi-C map from cow milk Human chromosome X Using a loop call to identify relative orientation of two genomic sequences.

Band-tailed pigeon *(Patagiaenas fasciata)* a b

Common wombat (Vombatus ursinus)   Virginia opossum (Didelphis virginiana)   Common raccoon (Procyan latar)

LINEAR GENOME ASSEMBLY FROM THREE DIMENSIONAL GENOME STRUCTURE

CROSS-REFERENCE TO RELATED APPLICATION

This application claims the benefit of U.S. Provisional Application No. 62/617,289, filed Jan. 14, 2018. The entire contents of the above-identified application are hereby fully incorporated herein by reference.

STATEMENT REGARDING FEDERALLY SPONSORED RESEARCH

This invention was made with government support under Grant Nos. HG003067, OD008540, HG009375, and HL130010 awarded by the National Institutes of Health, and Grant No. PHY1427654 awarded by the National Science Foundation. The government has certain rights in the invention.

BACKGROUND

Generating a high-quality genome sequence is a critical foundation for the analysis of any organism. Yet it remains a challenge, especially for genomes containing substantial repetitive sequence, such as Aedes aegypti, the principal vector of the Zika virus. Recently, an international consortium was organized to better understand Zika's principal vector by improving the quality of the A. aegypti genome (1).

Currently, most genomes are assembled from a deep collection of short DNA sequence reads. These data are combined with linking information, which makes it possible to estimate the distance between individual sequences; such linking information is typically obtained by sequencing paired ends from a DNA clone library with a characteristic insert size. On the basis of sequence overlap, the reads are assembled into contiguous sequences (contigs); by means of the linking information, the contigs are ordered and oriented with respect to one another into larger scaffolds (2). Within scaffolds, adjacent contigs are often separated by a gap, which corresponds to a region that is hard to assemble from the available sequence reads (for example, due to repetitive sequence or low coverage), but that can nevertheless be spanned by using the linking information to determine the contigs at either end of the gap. Long links, from large-insert clones such as Fosmids, have been especially valuable (3). Such clone libraries provide physical coverage (defined as the average number of clones spanning a point in the genome), often in the range of 1000-fold. With this strategy, it has been possible to produce mammalian genome assemblies with scaffolds ranging from 1-15 megabases (2, 3). However, it has generally not been feasible to achieve scaffolds that span entire chromosomes, because some repetitive regions are too large and difficult to be spanned by the available clone libraries.

Recently, Hi-C, a method for determining the 3D configuration of chromatin, has emerged as a valuable source of data for genome assembly (Lieberman-Aiden, van Berkum et al. 2009; Burton et al. 2013; Dudchenko et al. 2017). In Hi-C, DNA sequences that are near one another in 3D are transformed into chimeras through proximity ligation, and these "contacts" are then cataloged using high-throughput DNA sequencing. Because 3D proximity is closely correlated with proximity along the contour of the chromosome, Hi-C data has been used to create algorithms for scaffolding, phasing, and misjoin detection. Indeed, we recently showed that algorithmic analysis of Hi-C data using the 3D De Novo Assembly ("3D-DNA") algorithm makes it possible to generate de novo assemblies of mammalian genomes, with chromosome length scaffolds, at low cost (<$10,000) (Dudchenko et al. 2017).

SUMMARY

In one aspect, the present invention provides for a method for generating an error-corrected genome assembly for an organism comprising: generating a genomic contact map derived from a DNA proximity ligation assay conducted on one or more samples from the organism or a closely related species; superimposing a reference assembled genome derived from whole genome sequencing of one or more samples from the organism on top of the genomic contact map using computer software; correcting errors in the reference assembled genome through a computer user interface to obtain a corrected assembly file, wherein errors in the reference assembled genome are visualized by observing aberrant contacts in the genomic contact map; and applying the corrected assembly file to the reference assembled genome. The DNA proximity ligation assay may be Hi-C.

In certain embodiments, the reference assembled genome is generated using short-read sequencing technology, long-read sequencing technology, insert clones, linkage mapping data, physical mapping data, optical mapping date, or a combination thereof.

In certain embodiments, observing aberrant contacts in the genomic contact map is based, at least in part, on the frequency of contacts between one part of a contig or scaffold and other parts of the same contig or scaffold, or based on the frequency of contact between one part of a contig or scaffold and other contigs and scaffolds, or a combination thereof. The aberrant contacts may be misjoins, rearrangements, translocations, inversions, insertion, deletions, repeats, alignment errors, due to features of how the genome folds in three dimensions, cyclic permutations of the chromosomes, or a combination thereof. The translocations may be balanced translocations, unbalanced translocations, or a combination thereof. The repeats may be tandem repeats. In certain embodiments, a misjoin comprises a point along the diagonal of the contact map, a translocation comprises an extremely bright arrowhead motif pointing towards the diagonal of the contact map, and an inversion comprises two arrowhead motifs pointing at one another.

In certain embodiments, the organism is an animal or a plant.

In another aspect, the present invention provides for a computing system for generating an error-corrected genome assembly for an organism, said system comprising computer-executable instructions configured to superimpose a reference assembled genome derived from whole genome sequencing of one or more samples from the organism on top of a genomic contact map derived from a DNA proximity ligation assay conducted on one or more samples from the organism or a closely related species, and configured to allow visualization and correction of the assembled genome through a user interface, wherein correcting the assembled genome automatically corrects the genomic contact map. The DNA proximity ligation assay may be Hi-C.

In certain embodiments, the reference assembled genome is generated using short-read sequencing technology, long-read sequencing technology, insert clones, linkage mapping data, physical mapping data, optical mapping date, or a combination thereof.

In certain embodiments, visualization and correction of the assembled genome is based, at least in part, on the frequency of contacts between one part of a contig or scaffold and other parts of the same contig or scaffold, or based on the frequency of contact between one part of a contig or scaffold and other contigs and scaffolds, or a combination thereof.

In certain embodiments, the system allows visualizing and correcting misjoins, rearrangements, translocations, inversions, insertion, deletions, repeats, alignment errors, due to features of how the genome folds in three dimensions, cyclic permutations of the chromosomes, or a combination thereof. The translocations may be balanced translocations, unbalanced translocations, or a combination thereof. The repeats may be tandem repeats. In certain embodiments, a misjoin is visualized as a point along the diagonal of the contact map, a translocation is visualized as an extremely bright arrowhead motif pointing towards the diagonal of the contact map, and an inversion is visualized as two arrowhead motifs pointing at one another.

In certain embodiments, the organism is an animal or a plant.

In one aspect, the invention provides a method for de novo genome assembly comprising: generating a scaffold from sequencing reads derived from a DNA proximity ligation assay; generating a set of genomic sequencing contigs; and aligning the genomic sequencing contigs to the scaffold to generate a genome assembly. In one embodiment, the scaffold maps genomic loci that define one or more contact domains. In another embodiment, aligning the genomic sequencing contigs comprises determining a proper orientation of the genomic sequence contigs. In another embodiment, the proper orientation of the genomic sequence contigs is determined, at least in part, based on a frequency an end of a given contig forms contacts with other contigs. In another embodiment, the frequency is determined, at least in part, by application of a greedy algorithm.

In another aspect, the invention provides a method for de novo genome assembly comprising: combining reads from a DNA-DNA proximity ligation assay on a test sample with reads from a DNA-DNA proximity ligation assay of a reference sample to generate a combined 3D contact map; determining chromosomal breakpoints and/or fusions between the test sample and the reference sample from the combined contact map; realigning the test sample reads according to the determined breakpoints and/or fusions; and variant calling to replace one or more single nucleotide polymorphisms between the realigned test sample and the reference sample to derive a test sample reference genome. In one embodiment, the test sample. and the reference sample are from the same species. In another embodiment, the test sample and the reference sample are from closely related species.

In another aspect, the invention provides a method for de novo genome assembly comprising: generating a 3D contact map from sequencing reads derived from a DNA proximity ligation assay; ordering a set of genomic contigs based on the 3D contact map to generate a genome assembly. In one embodiment, the 3D contact map defines one or more contact domains. In another embodiment, the 3D contact map further defines centromere and telomere regions. In another embodiment, the method further comprises a correction step to remove undercollapsed heterozygosity. In another embodiment, aligning a set of genomic contigs comprises determining a proper orientation of the genomic sequence contigs. In another embodiment, the proper orientation of the genomic sequence contigs is determined based on identifying a proper orientation of CTCF motifs defining one or more contact domains in the 3D contact map. In another embodiment, the proper orientation of the genomic sequence is determined, at least in part, based on a frequency an end of a given contig forms contacts with an end of other contigs. In another embodiment, the frequency is determined, at least in part, by application of a greedy algorithm.

In another aspect, the invention provides a computer implemented method for de novo genome assembly comprising: receiving, using one or more computing devices a set of input scaffolds; correcting, using the one or more computing device, misjoined sequencing reads in the set of input scaffolds; generating, using the one or more computing devices, chromosome length scaffolds (megascaffold) from the corrected input scaffolds; and splitting, using the one or more computing device, the megascaffold into individual chromosome scaffolds. In one embodiment, the input scaffolds comprise contact frequencies as determined using a DNA-DNA proximity ligation assay. In another embodiment, the DNA-DNA proximity ligation assay is Hi-C. In another embodiment, the method further comprises removing tiny scaffolds prior to the correcting step. In another embodiment, a tiny scaffold is less than 15 kb and/or has a N50 length of less than 6.1 kb. In another embodiment, the method further comprises merging, by the one or more computing devices, assembly errors due to undercollapsed heterozygosity.

In another aspect, the invention provides a method for de novo genome assembly comprising generating a set of input sequencing reads derived from DNA-DNA proximity ligation assays conducted on one or more samples and ordering an orienting the input. The ordering an orienting of input sequencing reads may be based in part on frequency an end of a given sequencing read forms contact with other sequencing reads in the set. The frequency may be determined, at least in part, by application of a greedy algorithm or an optimization algorithm. The input sequencing reads may be contigs, scaffolds, or a combination thereof. The input sequencing reads may be generated using short-read sequencing technology, long-read sequencing technology, insert clones, linkage mapping data, physical mapping data, optical mapping date, sequencing reads from DNA-DNA proximity ligation assays, or a combination thereof. The input sequencing reads may be from a single species or multiple species.

In another aspect, the invention comprises a method for misassembly detection in genome assemblies comprising detecting errors in one or more genome assemblies based, at least in part, on the frequency of contacts between one part of a contig or scaffold and other pars of the same contig or scaffold, or based on the frequency of contact between one part of a contig or scaffold and other contigs and scaffolds, or a combination thereof. The errors may be misjoins, rearrangements, translocations, inversions, insertion, deletions, repeats, alignment errors, due to features of how the genome folds in three dimensions, cyclic permutations of the chromosomes, or a combination thereof. The translocations may be balanced translocations, unbalanced translocations, or a combination thereof. The repeats may be tandem repeats. In certain example embodiments, the frequency of contact is determined based on a contact matrix derived from a DNA-DNA proximity ligation assay, wherein reads are represented as pixels in the contact map and wherein the contact frequency is a function of distance from a diagonal of the contact matrix. The contact matrix may be used to derive an expected model to determine the contact frequency. The contigs and scaffolds may be first ordered and oriented using the methods disclosed to generate a draft assembly prior to detecting any errors. The draft assembly may then be further reordered and reoriented based on the detected errors to improve the overall genome assembly.

In another aspect, the invention comprises a method for merging assembly errors due to undercollapsed heterozygosity comprising identifying alternative haplotypes in a genome assembly based at least in part on a frequency of contact between a sequence and other loci in the genome, and removing or merging the alternative haplotypes to produce a single consensus sequence. The frequency of contact may also be used in combination with sequence identity analysis, coverage analysis, or both to identify alternative haplotypes. The frequency of contact may be determined based on a contact matrix derived from a DNA-DNA proximity ligation assay, wherein reads are represented as pixels in the contact map and wherein contact frequency is a function of distance from the diagonal of the contact matrix. In certain example embodiments, the alternative haplotype may be merged to increase contiguity of the genome assembly or otherwise removed. The identification of alternative haplotypes may be done simultaneously on multiple genome assemblies.

In another aspect, the invention provides a method for phasing different haplotypes comprising calculating a frequency of contact between loci containing particular variants, wherein the frequency of contact is determined using sequencing reads derived from a DNA proximity ligation assay, wherein the frequency of contact between two variants indicates if two variants are on the same molecule. In certain example embodiments, the frequency of contact between two variants is compared to an expected model to determine whether the two variants are on the same molecule. The expected model may be determined based on a contact matrix derived from a DNA proximity ligation assay, wherein reads are represented as pixels in the contact map and wherein contact frequency is a function of distance from a diagonal of the contact matrix. In certain example embodiments, the analysis may be done in an iterative fashion and wherein in data from DNA proximity ligation experiments is used to go from one possible phasing of a variant set to another possible phasing of a variant set. The analysis of the data from the DNA proximity ligation experiments is performed using gradient descent, hill-climbing, a genetic algorithm, reducing to an instance of the Boolean satisfiability problem (SAT) and solving, or using any combinatorial optimization algorithm.

In another aspect, the invention provides a method for reference-assisted genome assembly. Reads from DNA-DNA proximity ligation reads on a test sample may be aligned to a reference sequence derived from a control sample to generate a combined 3D contact map. The chromosomal breakpoints and/or fusions are identified between the test sample and the reference sample to create a proxy genome assembly. Variant calling may then be used to identify one or more small-scale changes, such as indels and singe nucleotide polymorphisms, between the realigned test sample and the control reference sequence. Local reassembly is then performed on the identified variants to address the one or more small-scale changes to generate a final output genome assembly. The test sample and the reference sample may be from the same or different species, or from closely related or distantly related species. The breakpoints and fusions may be identified using one of the embodiments disclosed above. In certain example embodiments, the breakage and fusion points are examined to determine regions of synteny between the test and reference samples and/or polymorphisms. The test sample may be aligned to the same or different reference sample, or multiple test samples may be aligned to may different reference sample sequences. The breakage and fusion points may be examined to infer phylogenetic relationships between samples. In certain example embodiment, multiple reference-assisted assemblies may be prepared at the same time.

In another aspect, the invention provides a method for de novo gene assembly, wherein proper orientation of contigs and/or scaffolds is determined, at least in part, by the relative orientation of certain DNA motifs. The motif may be a CTCF mediated loop. The proper orientation may be determined, at least in part, from DNA-DNA proximity ligation assays, which may used to generate a 3D contact map defining one or more contact domains, loops, compartment domains, links, compartment loops, superloops, one or more compartment interactions. The 3D contact map may also define centromere and telomere regions. In certain example embodiment, the DNA-DNA proximity ligation assay is Hi-C. In certain example embodiments, wherein massively multiplex single cell Hi-C is used to identify different subpopulations with differences in scaling and long range behavior. The DNA-DNA proximity ligation assay may be performed on synchronized populations of cells. In certain example embodiments, the cells may be synchronized in metaphase. The method may be performed on one or more cell treated to modify genome folding. Modifications may include gene editing, degradation of proteins that play a role in genome folding (such as HDAc inhibitors, Degron that target CTCF, Cohesin etc.), and/or modification of transcriptional machinery. The methods may be used to assemble transcriptomes. In certain example embodiments bisulfate treatment is applied to ligation junctions derived from a proximity ligation experiment and used to analyze proximity between DNA loci in sample, including the frequency of methylation for one or more basis in a sample.

These and other aspects, objects, features, and advantages of the example embodiments will become apparent to those having ordinary skill in the art upon consideration of the following detailed description of illustrated example embodiments.

BRIEF DESCRIPTION OF DRAWINGS

An understanding of the features and advantages of the present invention will be obtained by reference to the following detailed description that sets forth illustrative embodiments, in which the principles of the invention may be utilized, and the accompanying drawings of which.

Figure 1:
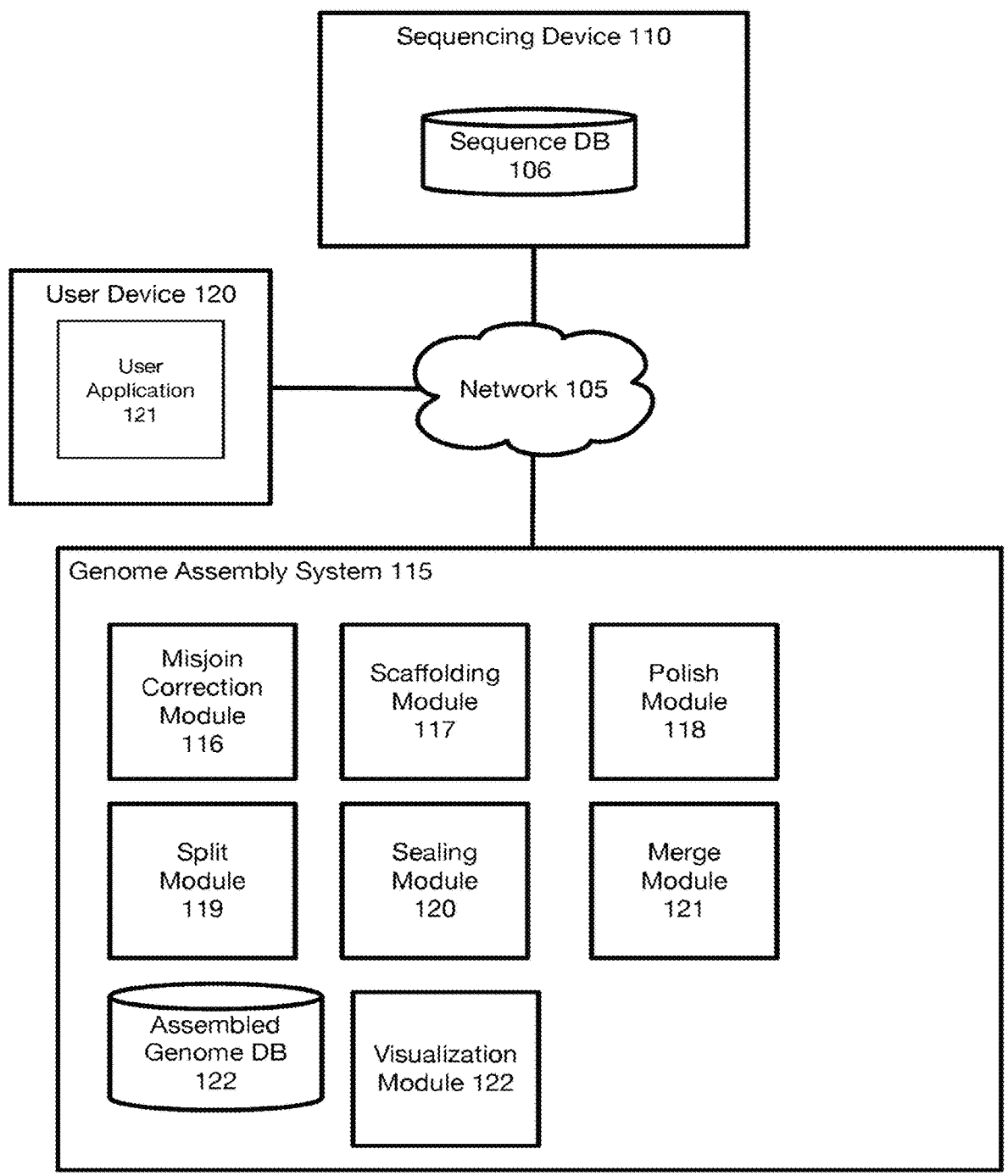
FIG. 1—Shows a block diagram depicting a system for generating genome assemblies, in accordance with certain example embodiments.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboraotry Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

As used herein the term "contig" refers to input sequences that are gap free and the term "scaffold" refers to input sequences that are permitted to contain gaps.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

The present invention provides a method for sequencing and assembling target genomes comprising generating a 3D contact map of chromatin loop structures in a target genome, the 3D contact map of chromatin loop structures defining spatial proximity relationships between genomic loci in the genome, and deriving a linear genomic nucleic acid sequence from the 3D map of chromatin loop structures.

Chromatin loop formation is the result of the presence of a pair of CTCF binding motifs in the convergent orientation on opposite strands of the DNA. The inventors have shown that a genome is partitioned into domains that are associated with particular patterns of histone marks that segregates into sub-compartments, distinguished by unique long-range contact patterns. Domain includes reference to superdomain and loop domain. A loop domain is a domain whose endpoints are anchored to form a chromatin loop. Loops are anchored at DNA sites bound by higher-order "loop anchor complexes" containing loop anchor proteins, including CTCF and cohesin, and other factors. Many loops demarcate domains; the vast majority of loops are anchored at a pair of convergent CTCF/RAD21/SMC3 binding sites. The pairs of CTCF motifs that anchor a loop are nearly all found in the convergent orientation. The inactive X chromosome (Xi) is found to be partitioned into two large "superdomains" whose boundary lies near the locus of the lncRNA DXZ4 (Chadwick, 2008). A network of extremely long-range (7-74 Mb) "superloops," has also been detected, the strongest of which are anchored at locations containing lncRNA genes (loc550643, XIST, DXZ4, and FIRRE). With the exception of XIST, all of these lncRNAs contain CTCF-binding tandem repeats that bind CTCF only on the inactive X.

Figure 27:
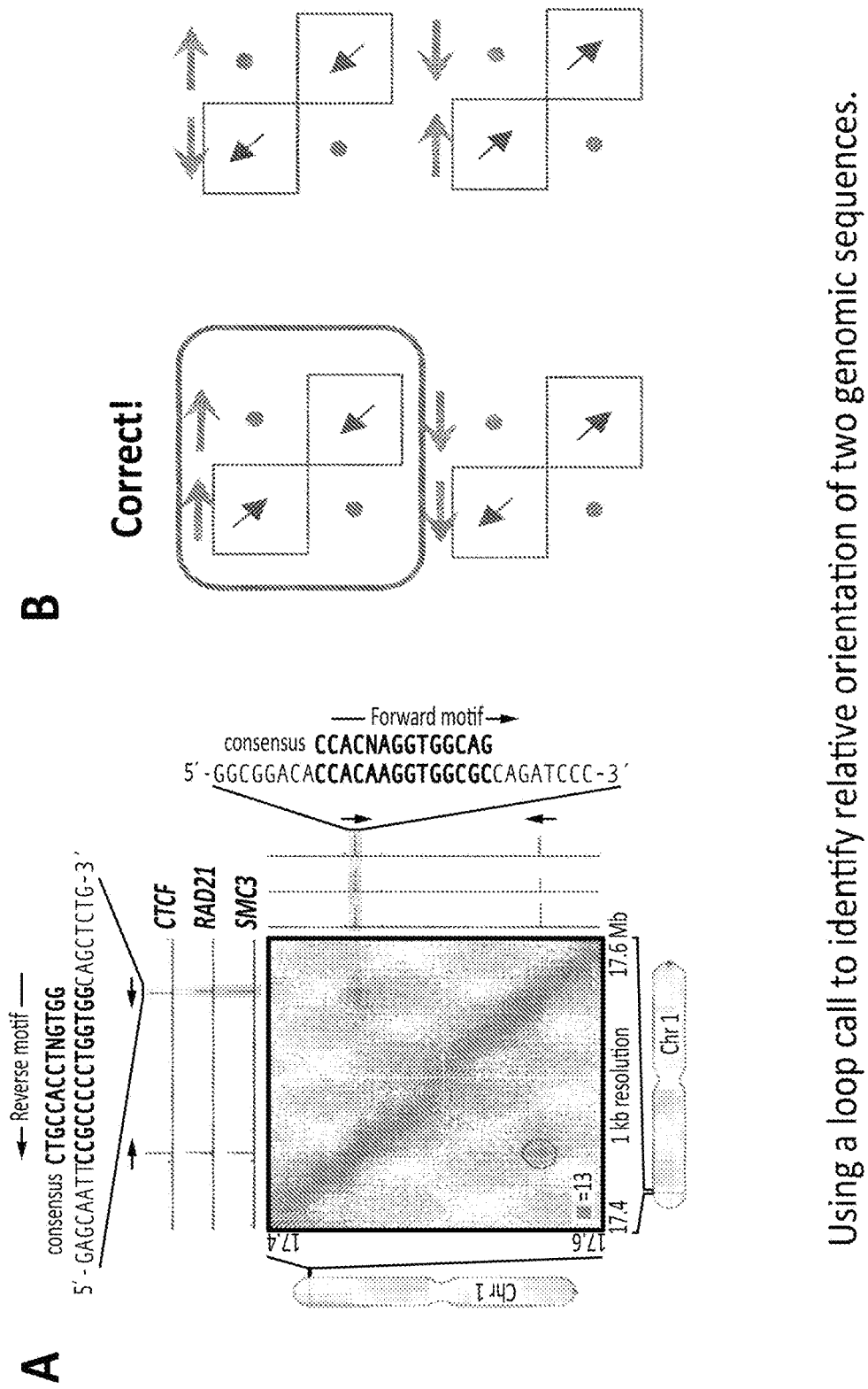
FIG. 27—Shows a schematic of how 3D features associated with oriented motifs can be used for genome assembly.
Figure 28:
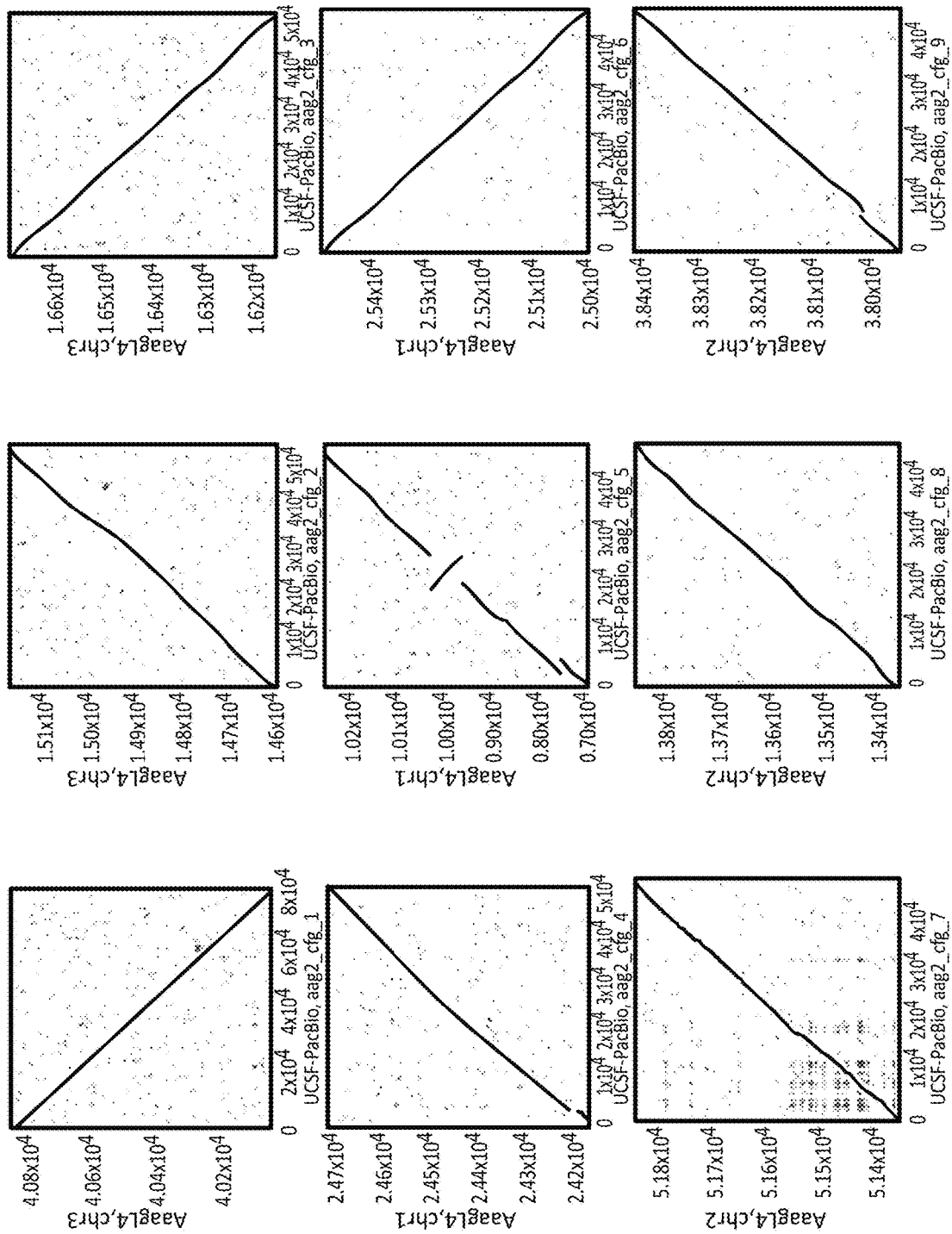
FIG. 28—Shows the AaegL4 genome, generated by ordering and orienting short contigs derived from the work of Nene et al. was aligned to the 9 largest contigs generated by Kunitomi et al. (average length 5.2 Mb) using the LastZ alignment algorithm (Robert S. Harris 2007). The resulting dot plots exhibit a strong correspondence between the two datasets for all contigs except contig #5, which reveals an inversion in the AaegL4 assembly. This inversion was confirmed upon examination of our in situ Hi-C data.
Figure 29:
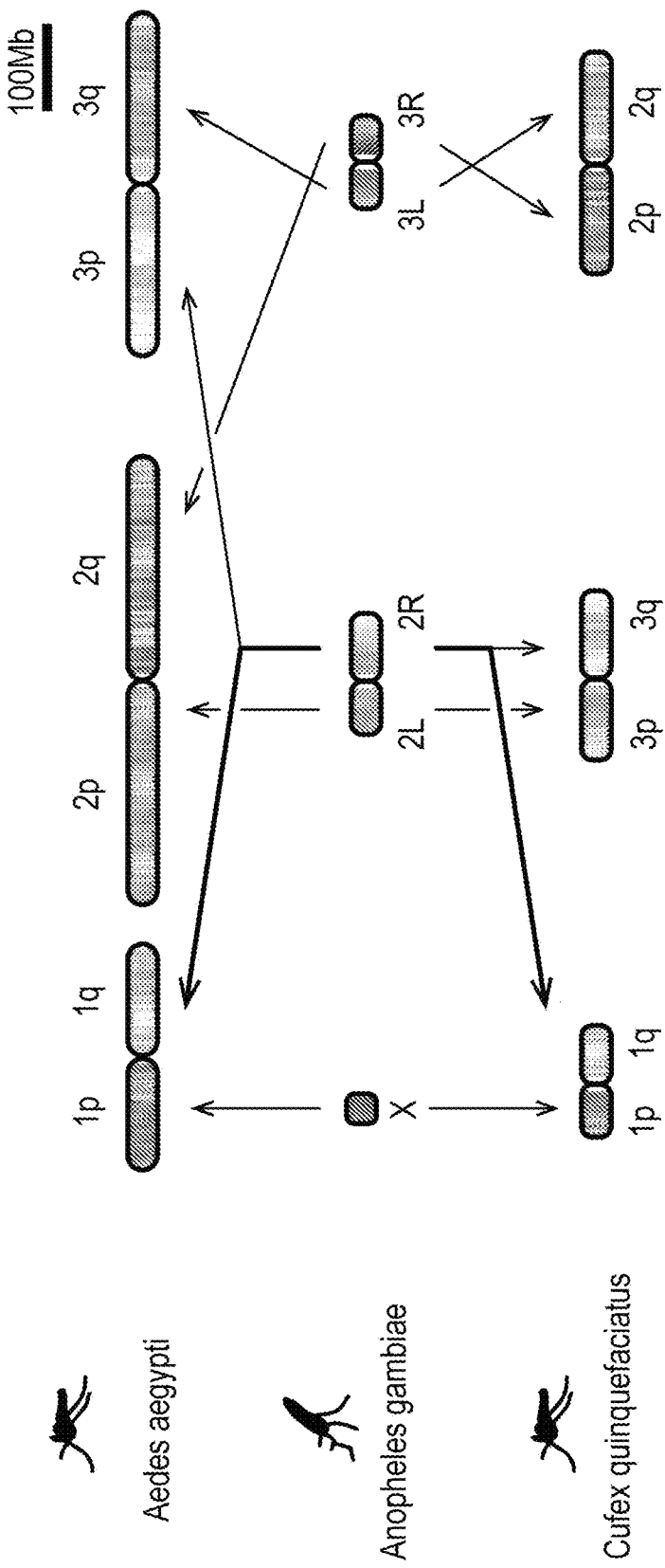
FIG. 29—Shows syntenic relationships between the *Aedes aegypti, Anopheles gambiae* and *Culex quinquefasciatus* mosquito genomes reveal conservation of the contents of ancestral chromosome arms. The *An. gambiae* mosquito is used as a reference. The chromosome arms of *Ae. aegypti* and *Cx. quinquefasciatus* are shown at 500 kb resolution. Each 500 kb pixel is a colored with a blend of colors corresponding to individual synteny blocks in *An. gambiae* weighted by block lengths. Chromosome arms deriving from the same ancestral arm exhibit similar colors. In one case, a single chromosome arm (*An. gambiae* 2R) corresponds to two arms in the other species. Chromosome arms are paired differently in each species.
Figure 30:
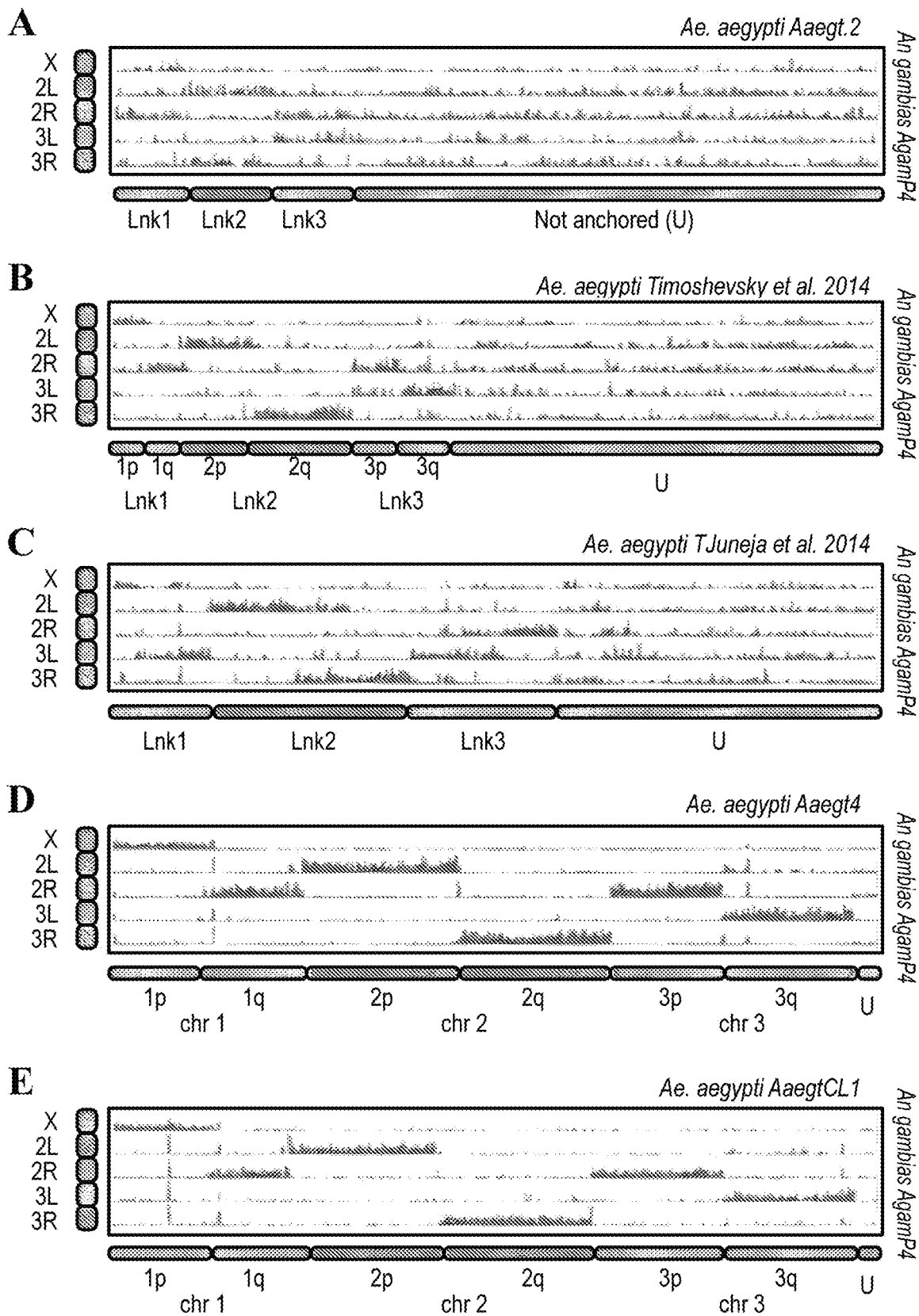
FIG. 30—Shows the AaegL4 and AaegCL1 assemblies enable genome-wide synteny analysis between *Ae. aegypti* and *An. gambiae* A) Conservation of synteny between chromosomes of *Ae. aegypti* and *An. gambiae* as suggested by the AaegL2 assembly. To perform this analysis, whole-genome alignment data was downloaded from VectorBase (Robert S. Harris 2007; Giraldo-Calderon et al. 2015) comprising pairs of orthologous positions in AaegL2 and Agam4. Orthologous pairs associated with a particular arm in *An. gambiae* (indicated at left) were grouped together, and the corresponding positions on AaegL2 are shown using a histogram at 1 Mb resolution. (The y-axes in this panel and throughout the figure correspond to raw counts, from 1 to 100.) Below the histogram tracks, we show the linkage groups reported in AaegL2 (Nene et al. 2007). The unanchored portion of the assembly is shown in grey. B) The synteny analysis from panel A is repeated using improved linkage groups generated via physical mapping (Timoshevskiy et al. 2014), which are indicated below the plot. C) The synteny analysis from panel A is repeated using improved linkage groups generated via genetic linkage mapping (Juneja et al. 2014), which are indicated below the plot. D) Synteny analysis for the AaegL4 assembly. A one-to-one correspondence between the chromosome arms of *Ae. aegypti* and *An. gambiae* is apparent. E) Synteny analysis for the AaegCL1 assembly. To generate this plot, we performed whole-genome alignment of the Aag2 contigs and the AgamP4 genome using the LastZ alignment algorithm with *An. gambiae* as a reference species. After running LastZ the raw alignment blocks were chained and netted according to their location in the AgamP4 genome.
Figure 31:
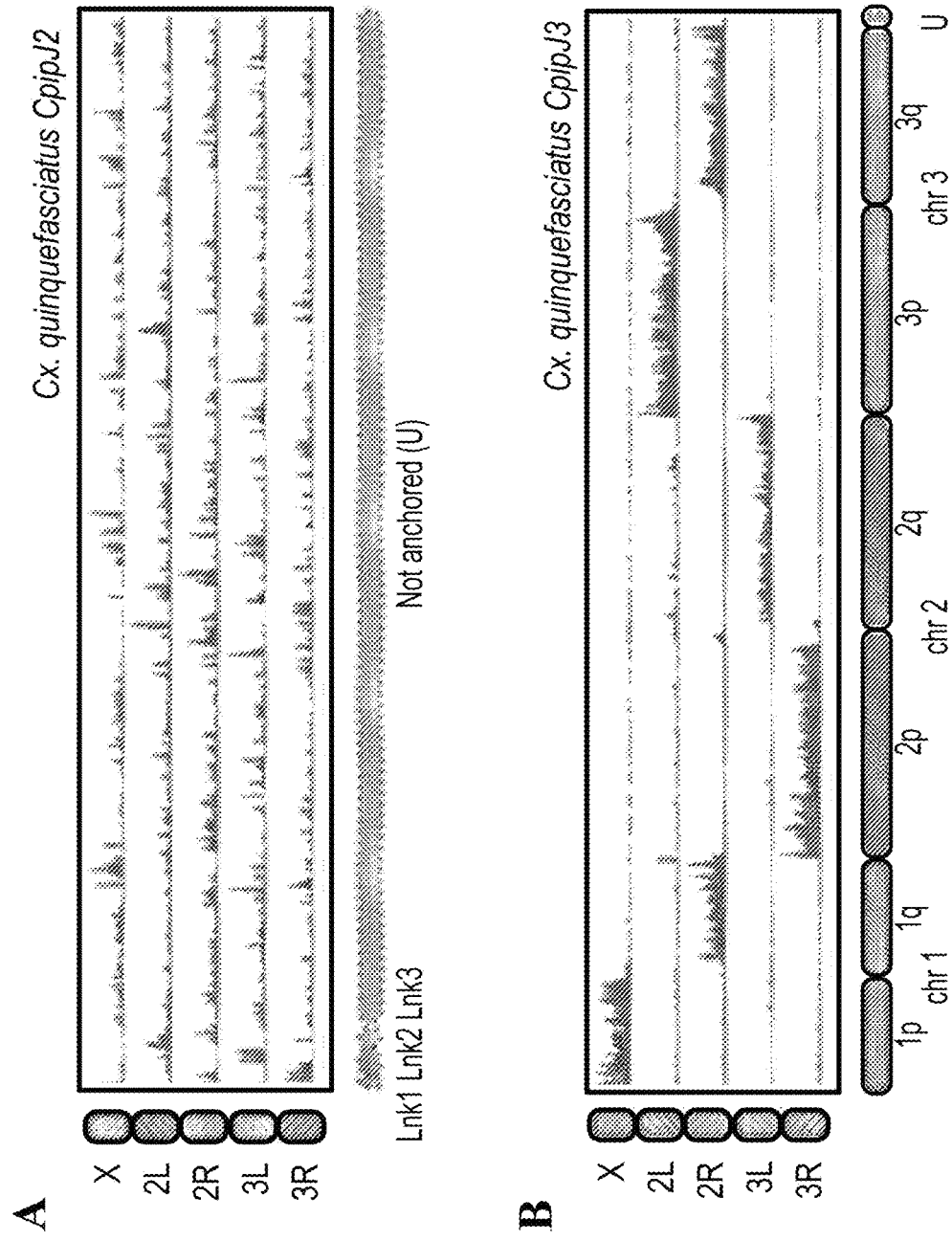
FIG. 31—Shows the CpipJ3 assembly reveals strong conservation of the contents of chromosome arms between *Cx. quinquefasciatus* and *An. gambiae*. A) Conservation of synteny between chromosomes of *Cx. quinquefasciatus* and *An. gambiae* as suggested by the CpipJ2 assembly. B) Conservation of synteny as represented by the CpipJ3 assembly. To perform this analysis, LASTZ_Net whole-genome alignment data from VectorBase was used (Robert S. Harris 2007; Giraldo-Calderon et al. 2015).
Figure 32:
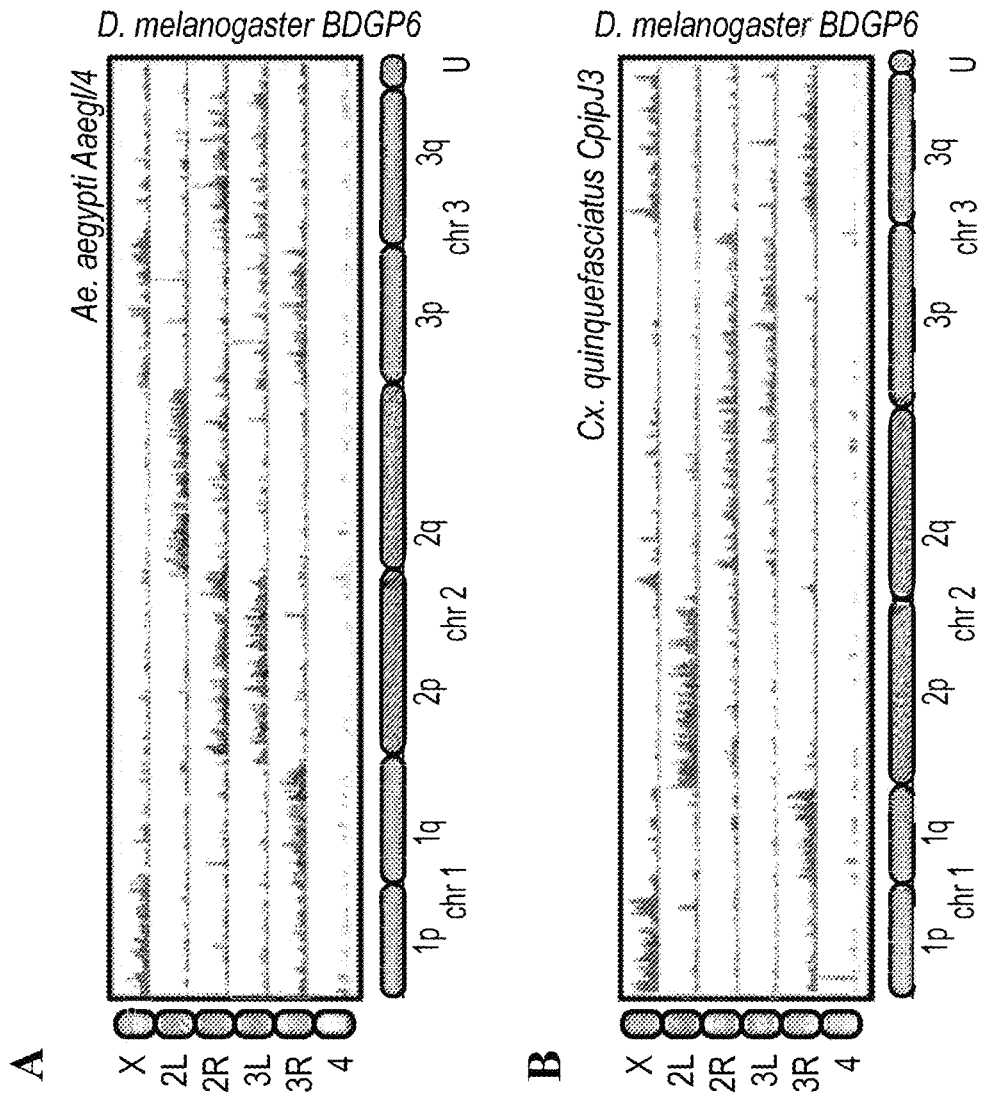
FIG. 32—Shows conservation of synteny across dipterans. Several chromosome arms, such as *Ae. aegypti* 2q (AaegL4), *Cx. quinquefasciatus* 2p and *D. melanogaster* 2L (BDGP6), show strong conservation of content. The whole-genome alignments for this analysis has been downloaded from Ensembl (Yates et al. 2016).
Figure 33:
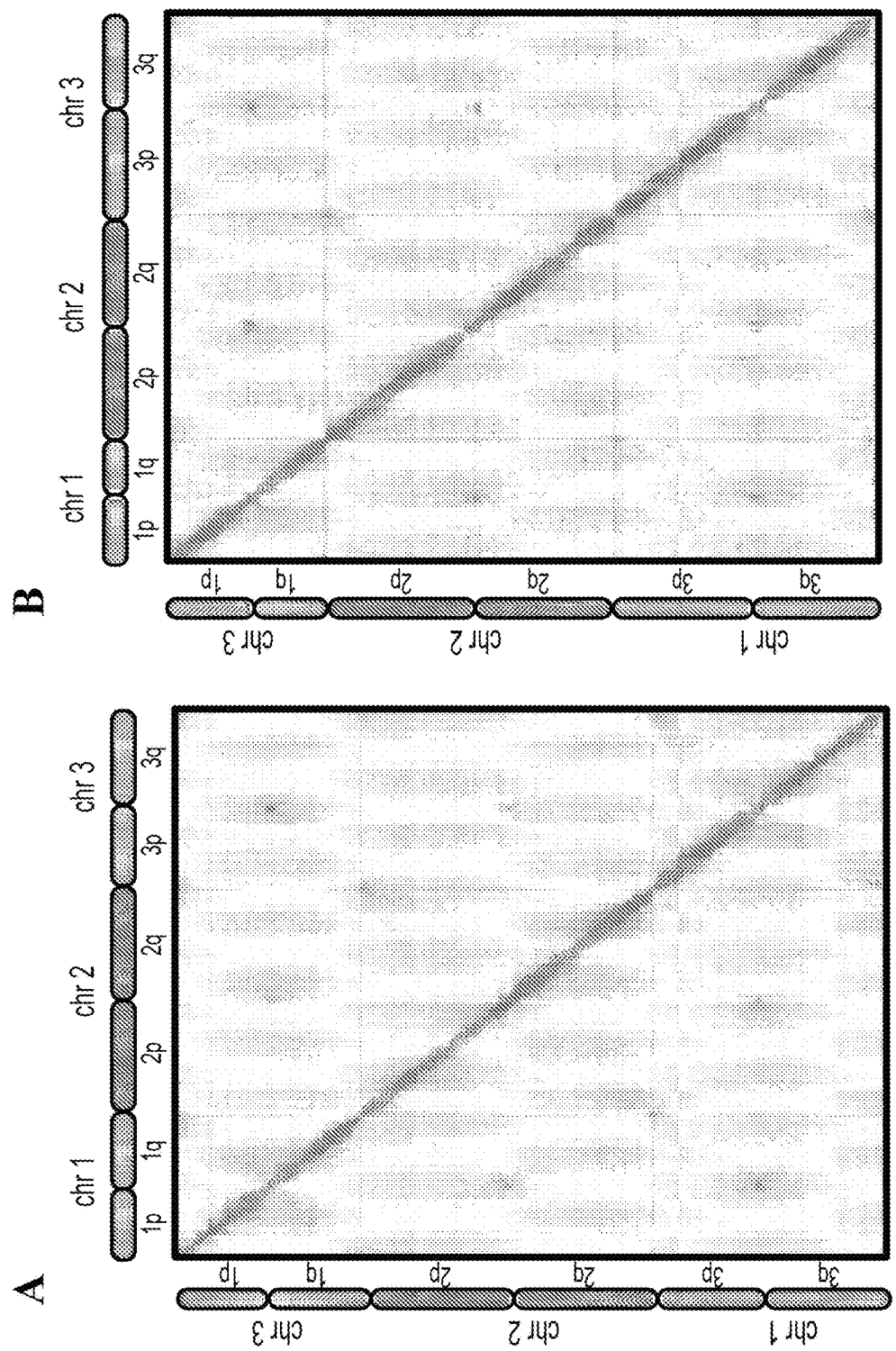
FIG. 33—Shows Hi-C map of the end-to-end assembly AaegL4 (A) and CpipJ3 (B). Bright, off-diagonal peaks indicate the spatial clustering of telomeres and centromeres, an arrangement known as the Rabl configuration. The map of AaegCL1 is similar. The genomes are not to scale.

In one embodiment, the method of de novo genome assembly comprises generating a 3D contact map for a sample to be sequenced. A 3D contact map is a list of DNA-DNA contacts produced by a DNA proximity ligation assay, such as the in situ Hi-C assays described in WO 2016/089920. By partitioning the linear genome into "loci" of fixed sized (e.g. binds of 1 MB or 1 Kb), the 3D contact map can be represented as a "contact matrix" M, where the entry $M_{ij}$ is the number of contacts observed between locus $L_i$ and $L_j$. A "contact" is a read pair that remains after exclusion of reads that do not align to a reference genome, that correspond to un-ligated fragments, or that are duplicates. The contact map can be visualized as a heatmap whose entries are calls "pixels." An "interval" refers to a one-dimensional set of consecutive loci. The contacts between two intervals thus may form a "rectangle" or "square: in the contact matrix. "Matrix resolution" is the locus size used to construct a particular contact matrix and "map resolution" is the smallest locus size such that 80% of loci have at least 1,000 contacts. The map resolution describes the finest scale at which one can reliably discern local features. The 3D contact maps may be used to discern contact domains which are contiguous genomic intervals in which there is an enhanced probability of contact among all loci (which manifest as bright spots off the diagonal of the contact map), as well as the location of centromeres and telomeres. See FIG. 1 and FIG. 27. These features, and the ability to discern distances between loci relative and/or contig orientation relative to said features provides a basis for the de novo sequencing approaches disclosed herein.

In certain example embodiments, the DNA-DNA proximity ligation assay is Hi-C. Hi-C is a sequencing-based approach for determining how a genome is folded by measuring the frequency of contact between pairs of loci (4, 5). Contact frequency depends strongly on the one-dimensional distance, in base pairs, between a pair of loci. For instance, loci separated by 10 kb in the human genome form contacts 8 times more often than those at a distance of 100 kb. In absolute terms, a typical distribution of Hi-C contacts from a given locus is 15% to loci within 10 kb; 15% to loci 10 kb-100 kb away; 18% to loci 100 kb-1 Mb away; 13% to loci 1 Mb-10 Mb away; 16% to loci 10 Mb-100 Mb away; 2% to loci on the same chromosome, but more than 100 Mb away; and 21% to loci on a different chromosome. Hi-C data can provide links across a variety of length scales, spanning even whole chromosomes. However, unlike paired-end reads from clone libraries, any given Hi-C contact spans an unknown length and may connect loci on different chromosomes. This challenge may be mitigated, in part, by the physical coverage achieved by Hi-C datasets. For the maps reported in (4, 5), summing the span of each individual contact reveals that 1× of sequence coverage of the target genome translates, on average, into 23,000× of physical coverage. This suggests that a statistical approach analyzing the pattern of Hi-C contacts as a whole could generate extremely long scaffolds In one embodiment the sequencing method provides de novo genome assembly comprising generating a 3D contact map from sequencing reads derived from DNA proximity ligation assays conducted on a sample, such as the in situ Hi-C assays described herein, wherein the 3D contact maps identify genomic loci that define one or more contact domains. Genomic sequencing contigs are then generated using known methods in the art. The sequencing contigs may be prepared from a new sample to be sequenced or obtained from a database of previously sequenced contigs. In characterizing sets of input scaffolds, it is also useful to define the "effective N50 length" of the input scaffolds. This is simply the N50 of the scaffolds after all misjoins they contain have been corrected. Of course, for a typical published set of scaffolds, the effective N50 is not known, since it may contain misjoins and other scaffolding errors that the authors were unaware of. Naturally, the actual N50 of the scaffold set furnishes an upper bound for the effective N50—but the two are often not equal in practice. The embodiment disclosed herein provide a way to remove misjoins until the underlying scaffold set is largely free of misjoins. If there is a disparity between the actual N50 length of the input scaffolds and their effective N50 length, it will be greatly reduced by this step. After misjoin detection, the resulting input scaffolds are used to create the final ordered-and-oriented chromosome-length scaffolds.

In certain example embodiments, the method comprises a set of iterative steps whose goal is to eliminate misjoins in the input scaffolds. Each step begins with a scaffold pool. Initially, this pool is the set of input scaffolds themselves. The embodiment disclosed herein then order and orient these scaffolds. A misjoin correction module is applied to detect errors in the scaffold pool. The edited scaffold pool is used as an input for the next iteration of the application of the misjoin correction module. The ultimate effect of these iterations is to reliably detect misjoins in the input scaffolds without removing correctly assembled sequence. After the iterations are complete, a scaffolding module is applied to the revised scaffolding inputs, and the output—a single megascaffold which concatenates all chromosomes—is retained for further processing. Further processing may comprise four additional steps; (i) application of a polishing module, which is required for genomes in the Rabl configuration; (ii) application of a chromosome splitting module, which is used to extract the chromosome-length scaffolds from the megascaffold; (iii) a sealing module, which detects false positives in the misjoin correction process and restores the erroneously removed sequences from the original scaffold; and (iv) a merge module, which corrects misassembly errors due to undercollapsed heterozygosity in the input scaffold. Step (ii) may be omitted for genomes that are not in the Rable configuration and step (iv) may be omitted if the original scaffolds lack substantial undercollapsed heterozygosity. In certain example embodiments, the computer-implemented method may be written in the AWK programming language in combination with bash scripting, or other program language that facilitates higher i/o rates. It may be further optimized for speed, for example, by using GNU Parallel shell tool (27), but can also be run without parallelization.

Example System Architectures

FIG. 1 is a block diagram depicting a system for de novo genome assemblies from three-dimensional contact maps of sequencing reads obtained from DNA proximity ligation assays. As depicted in the FIG. 1, the system 100 includes devices 110, 115, and 120 that may be configured to communicate with one another via one or more networks 105.

The sequencing device 110 may be any standard sequencing device capable of creating data files from sequencing reads of a sample. The sequencing device 110 may comprise a sequence database 106 or other storage structure for maintaining such data files.

The genome assembly system 115 may comprise a misjoin correction module 116, a scaffolding module 117, a polish module 118, a split module 119, sealing module 120, and a merge module 121. These modules work together to process input sequencing files to obtain a final genome assembly. Such final genome assemblies may be stored in an assembled genome database 122 or other storage media.

The user device 120 may comprise any user device as described below and may further comprise an application 121 for visualizing and/or manipulating preliminary assembly data to derive a final verified genome assembly. In certain example embodiments, and end user may have to download the user application 121 to obtain full benefit of the methods disclosed herein.

Each network 105 may include a wired or wireless telecommunication means by which network devices (including devices 110, 115, and 120) can exchange data. For example, each network 105 can include a local area network ("LAN"), a wide area network ("WAN"), an intranet, an Internet, a mobile telephone network, or any combination thereof. Throughout the discussion of example embodiments, it should be understood that the terms "data" and "information" are used interchangeably herein to refer to text, images, audio, video, or any other form of information that can exist in a computer-based environment.

Each network device 110, 115, and 120 includes a device having a communication module capable of transmitting and receiving data over the network 105. For example, each network device 110, 115 and 120 can include a server, desktop computer, laptop computer, tablet computer, a television with one or more processors embedded therein and/or coupled thereto, smart phone, handheld computer, personal digital assistant ("PDA"), or any other wired or wireless, processor-driven device. In the example embodiment depicted in FIG. 1, the network devices (including systems 110 and 115).

It will be appreciated that the network connections shown are example and other means of establishing a communications link between the computers and devices can be used. Moreover, those having ordinary skill in the art having the benefit of the present disclosure will appreciate that the sequencing device 110. genome assembly device 115, and user device 120 illustrated in FIG. 1 can have any of several other suitable computer system configurations. For example, a user device 120 embodied as a mobile phone or handheld computer may not include all the components described above.

Example Processes

Figure 2:
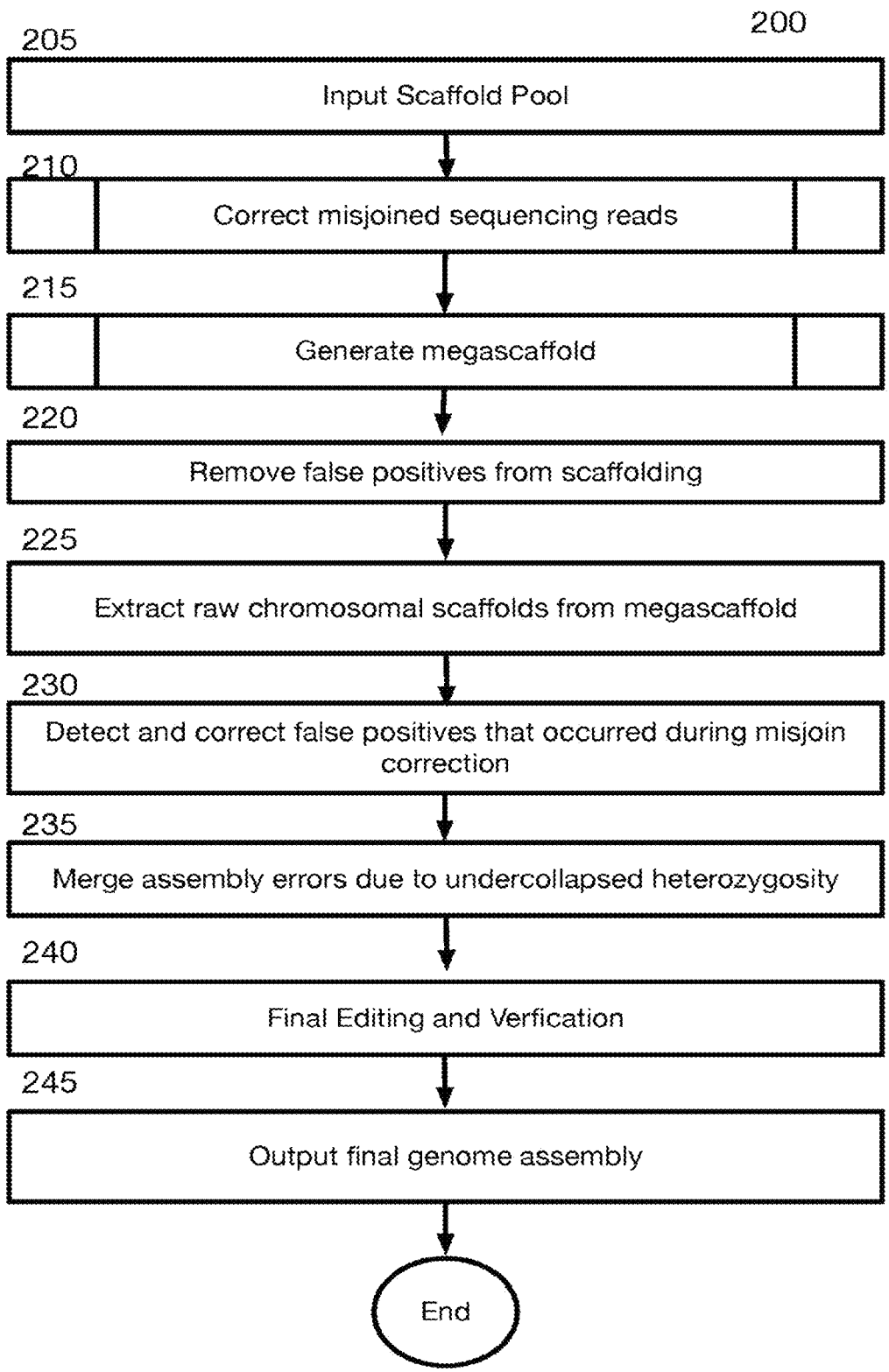
FIG. 2—Shows a block flow diagram depicting a method of generating genome assemblies from contact density data, in accordance with certain example embodiments.
Figure 3:
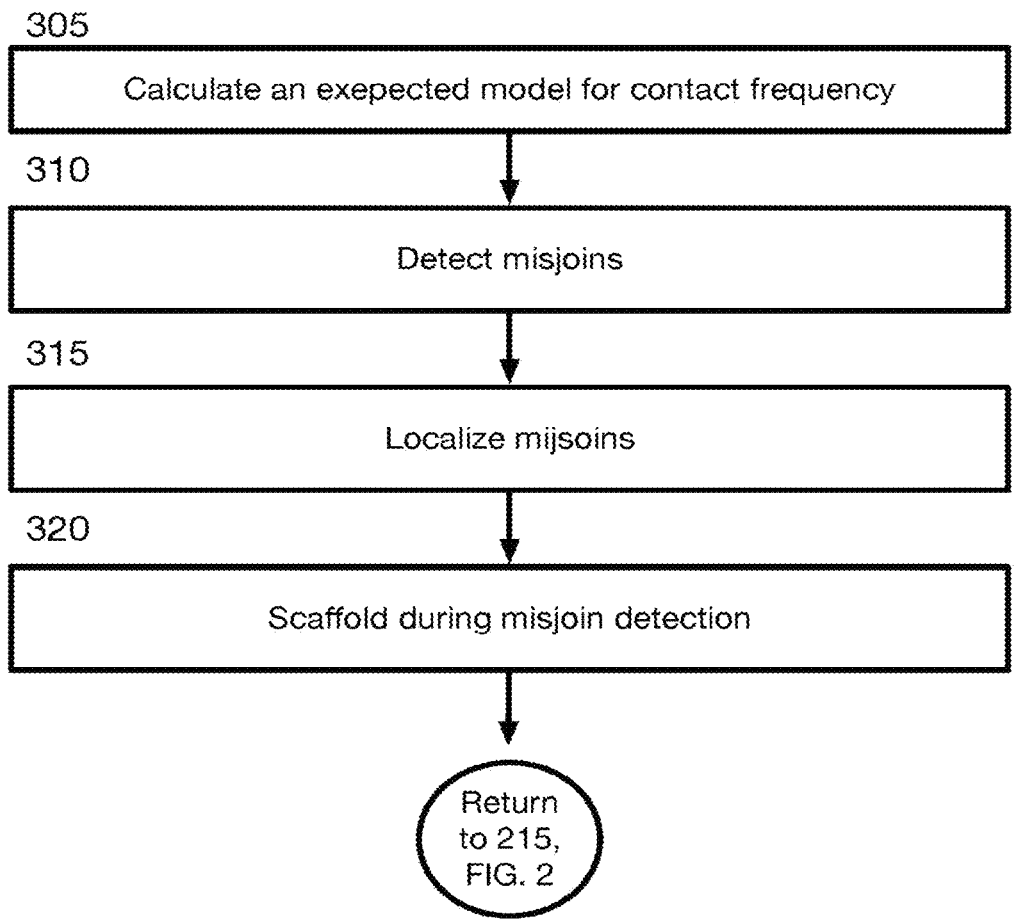
FIG. 3—Shows a block flow diagram depicting a method for detecting misjoins in input scaffolds, in accordance with certain example embodiments.
Figure 4:
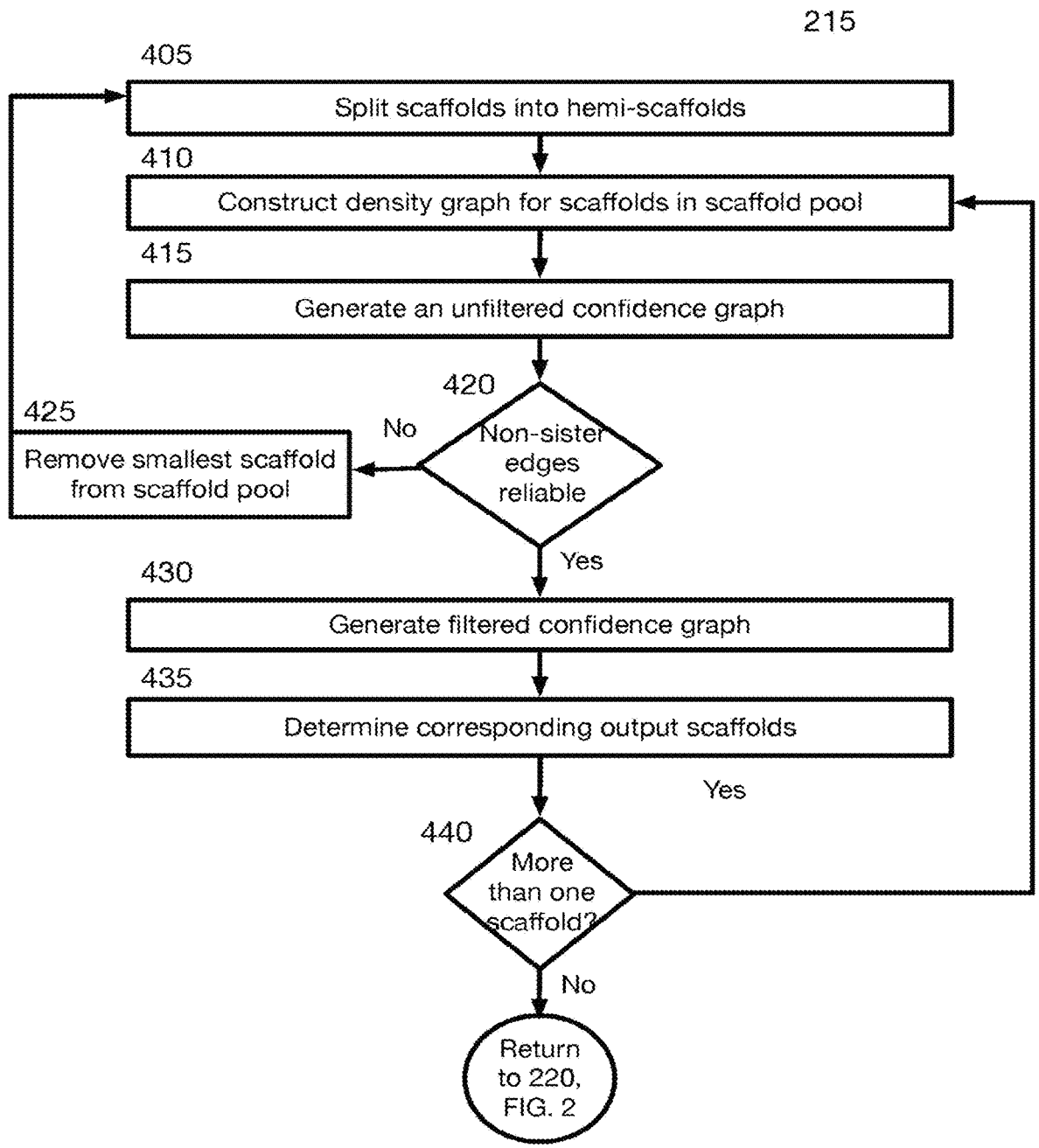
FIG. 4—Shows a block flow diagram depicting a method for generating a concatenated version of all scaffolds (megascaffold), in accordance with certain example embodiments.
Figure 5:
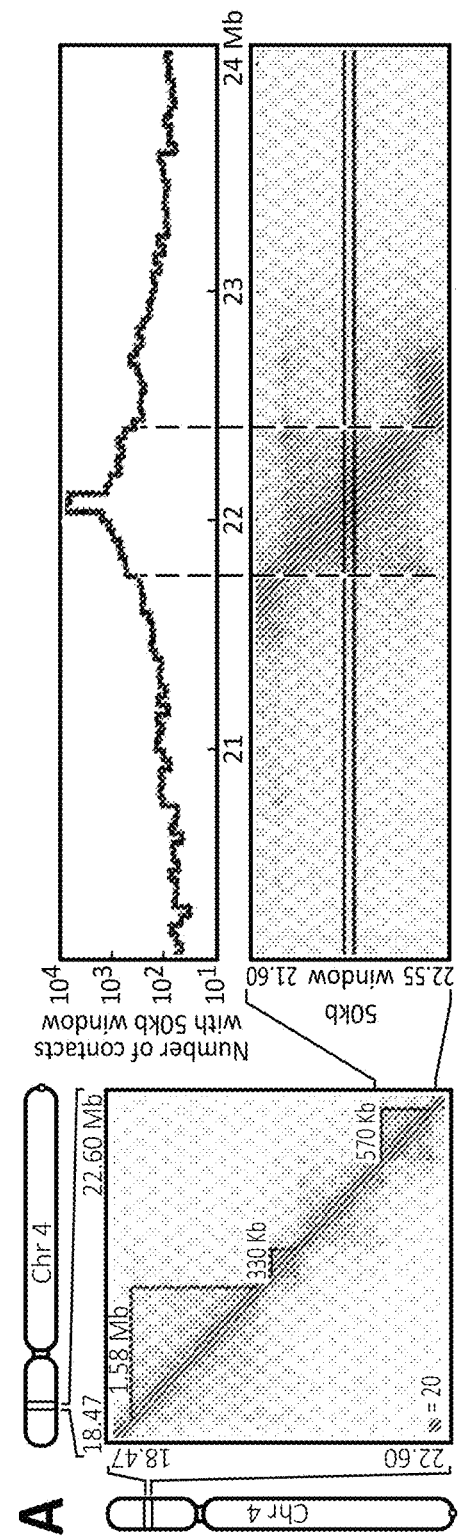
FIG. 5—Shows a representative 3D contact map and the delineation of contact domains within the 3D contact map.
Figure 6:
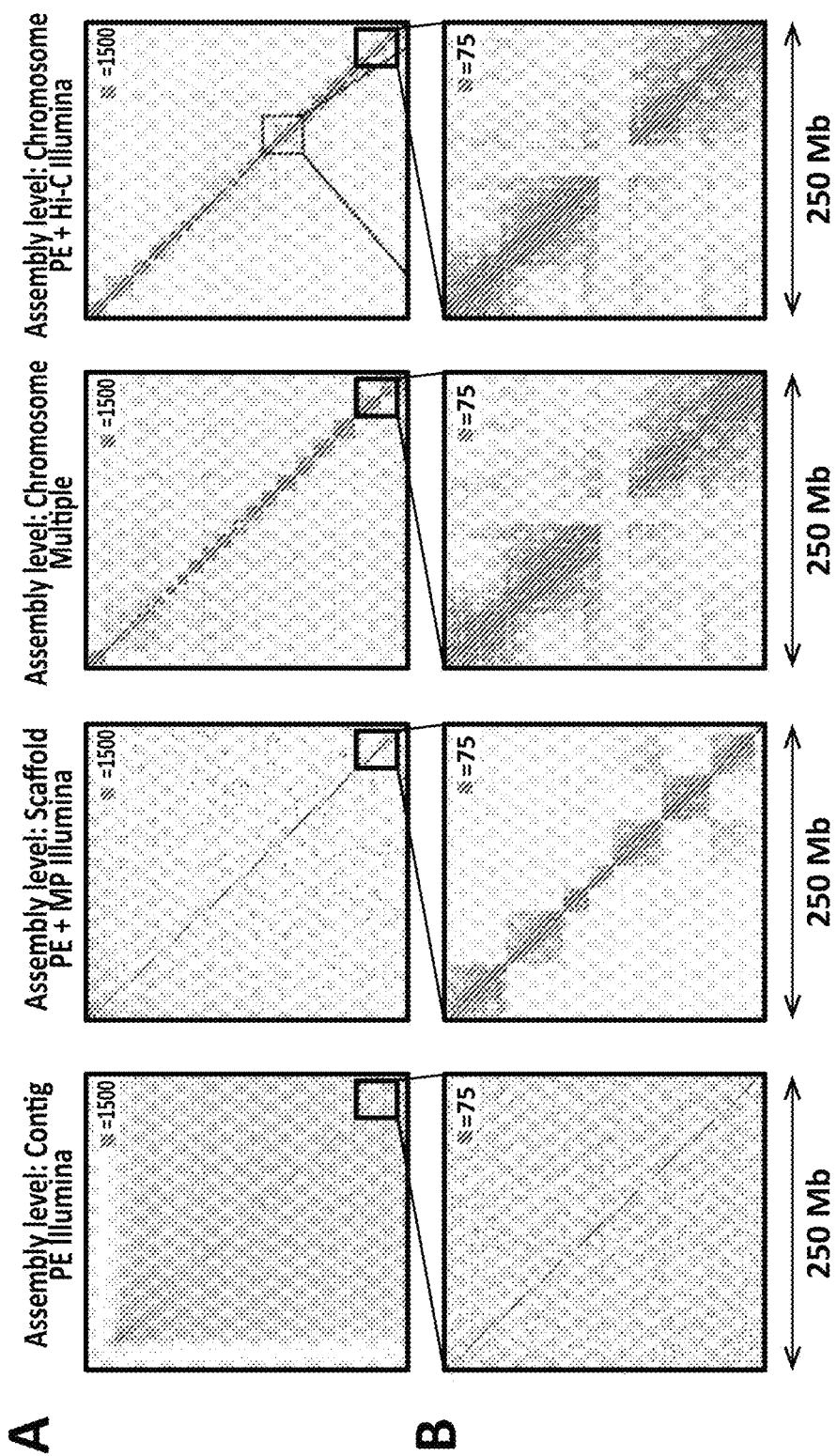
FIG. 6—Shows that a Hi-C data enables end-to-end assembly of entire chromosomes from short contigs. A Hi-C map also provides a simple way to assess the quality of an assembly. A: Human genome assemblies created by different technologies as visualized by in situ Hi-C data. Presented are short read paired-end lllumina {DISCOVAR de novo assembly produced as part of the preliminary dataset}; paired-end+mate pair and Fosmid data {Gnerre et al. 2011}; hg19; and a de novo Hi-C assembly created by applying the methods disclose herein to DISCOVAR contigs. Contigs, correct scaffolds, and chromosomes manifest themselves in Hi-C maps as bright, relatively uniform squares along the diagonal. Off-diagonal squares indicate nearby pieces of the genome that were not correctly scaffolded. The methods disclosed herein analyze these strong off-diagonal signals to order and orient contigs into chromosome-sized scaffolds. In an assembly featuring end-to-end chromosomal scaffolds, the number of squares along the diagonal equals the number of chromosomes; so long as there are no errors, bright blocks are not seen off the diagonal. No miss-assembly errors are seen in generated de novo human assembly. B: Zoomed in portions of the map {250 Mb×250 Mb}. Note that the centromere gap in the Hi-C assembly has been added for ease of visual comparison. Further, Hi-C data make it possible to calculate gap sizes in an automated fashion.
Figure 7:
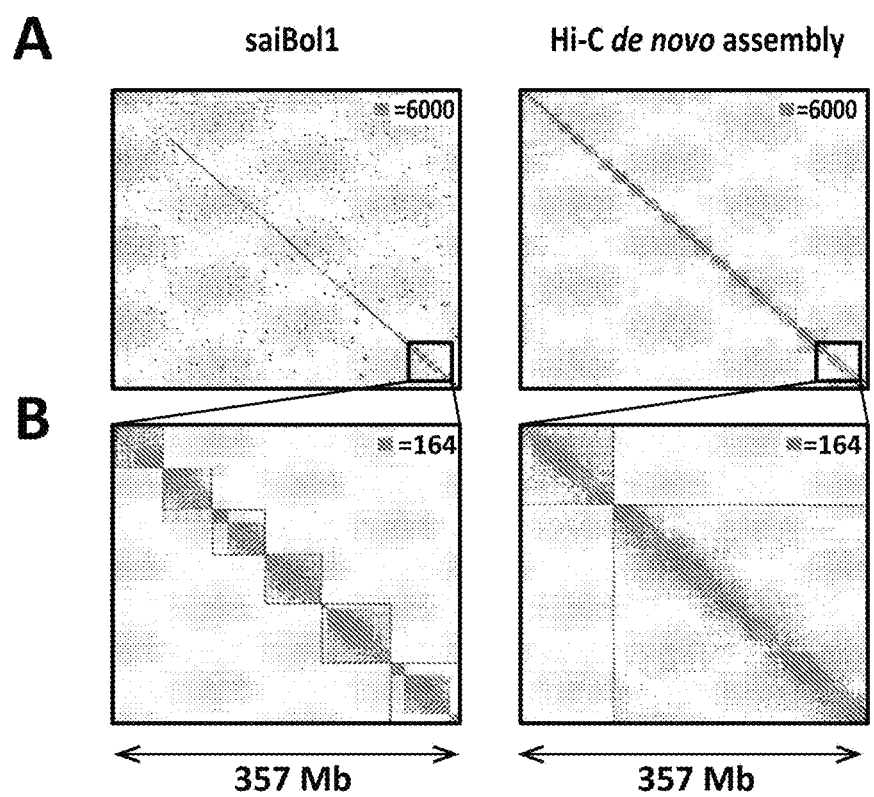
FIG. 7—Shows Hi-C de novo assembly of *Saimiri boliviensis* (squirrel monkey) as compared to saiBol1, the currently available assembly for the species. A: Genome-wide view, with scaffolds in both assemblies sorted by size. The number of blocks in the Hi-C assembly is 22, the number of squirrel monkey chromosomes. This indicates that the Hi-C assembly has successfully generated an end-to-end scaffold for each chromosome. B: Zooming in on the largest scaffolds.
Figure 8:
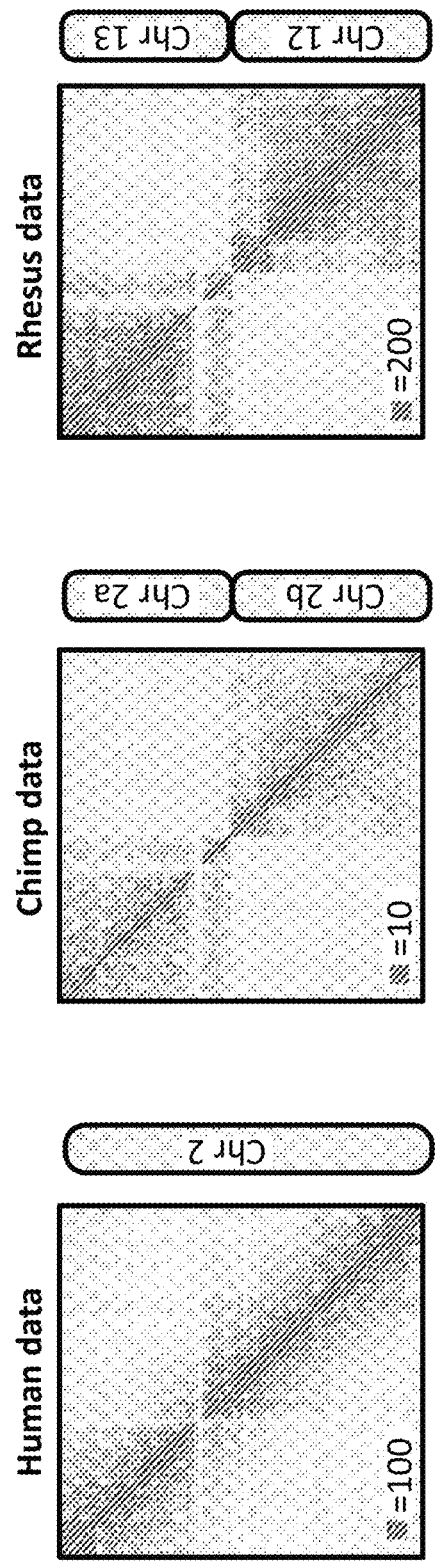
FIG. 8—Shows in one example embodiment, maps of human chromosome 2 generated using methods disclosed herein indicate that chromosome 2 is a result of fusion of two ancestral chromosomes: when chimp or rhesus Hi-C data are aligned to the human genome, the formation of depleted anti-diagonal blocks indicates the breakpoint.
Figure 9:
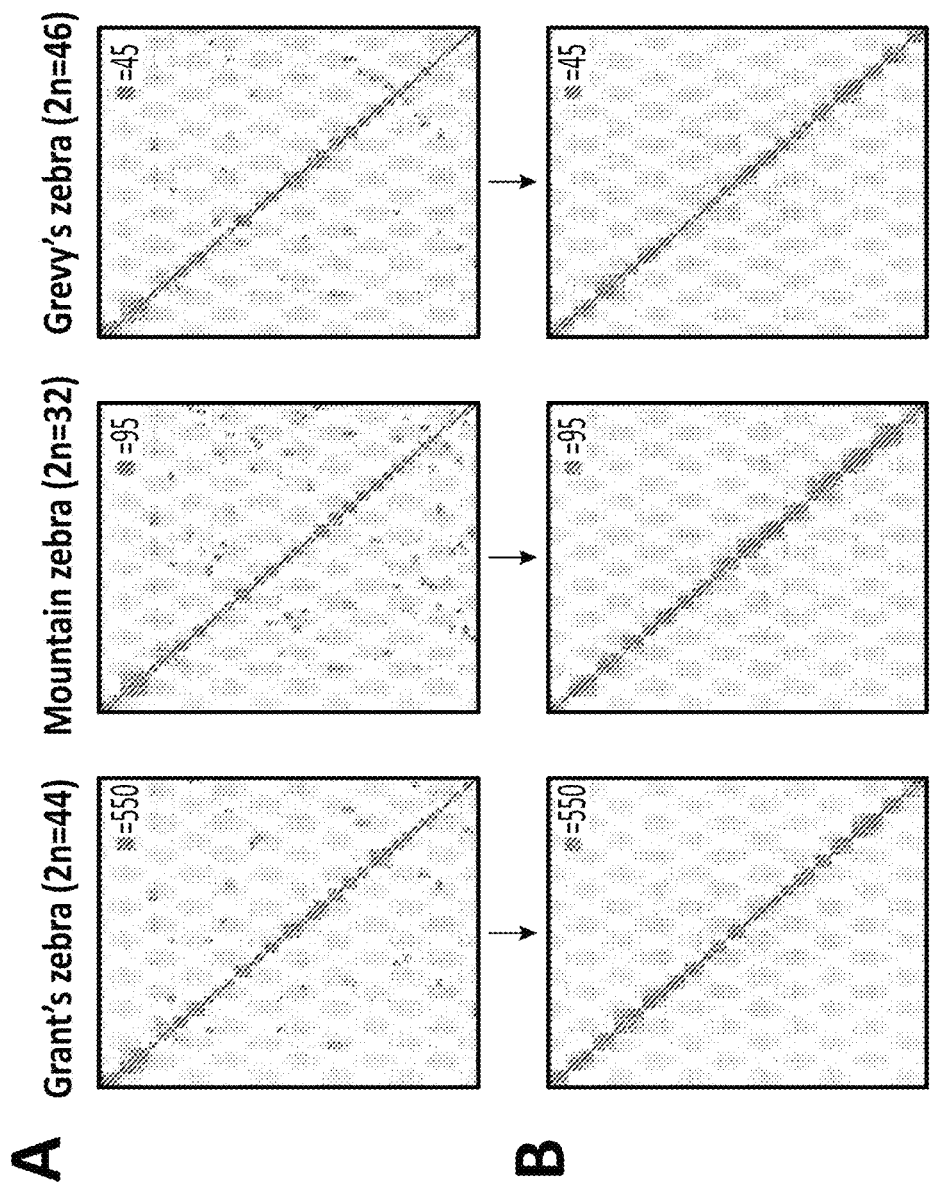
FIG. 9—Shows assisted assembly of three zebra species: Grant's Zebra, Mountain Zebra, and Grevy's Zebra. In panel A, the data for each species are aligned to the horse genome. Each off-diagonal block corresponds to a breakpoint (note that the matrix is symmetric, so a breakpoint yields two corresponding off-diagonal blocks, B: Shows the data aligned to an assembly generated using these data. The choice of chromosome order and orientation is arbitrary. These assemblies allowed exact recapitulation of karyotypic analyses performed using microscopy to determine syntenic blocks between horse and zebra.
Figure 10:
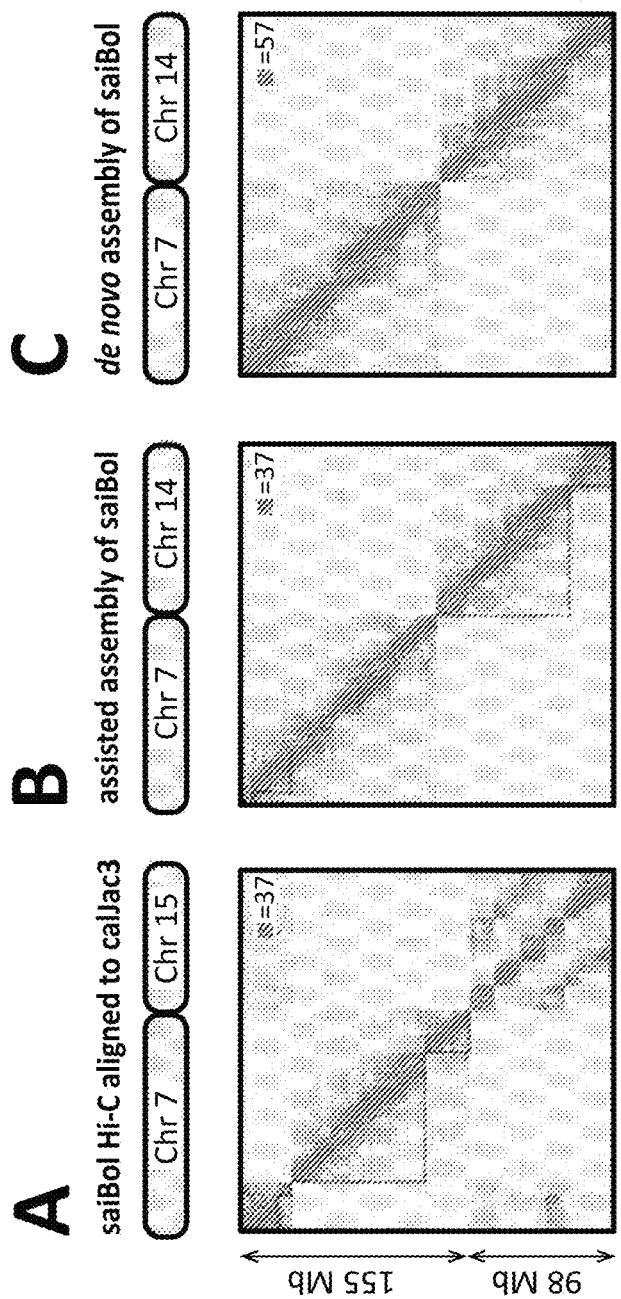
FIG. 10—Shows assisted Hi-C assemblies correspond perfectly to de novo assemblies. A: *S. boliviensis* data aligned to the common marmoset assembly {fragment}. Note the outlined breakpoints in the map suggesting karyotypic differences between the two species. B: Assisted assembly of *S. boliviensis* based on marmoset; syntenic blocks are outlined, illustrating how the algorithm shuffles one genome to determine another. C: De novo assembly of the same pair of chromosomes. *S. boliviensis* chromosomes are numbered according to size, from larger to smaller. B and C are indistinguishable.

The methods illustrated in FIGS. 2-4 are described hereinafter with respect to the components of the example operating environment 100. The example method of FIGS. 2-4 may also be performed with other systems and in other environments.

FIG. 2 is a block flow diagram depicting a method 200 for de novo genome assembly from three-dimensional contact maps of sequencing reads obtained from DNA proximity ligation assays. Method 200 begins at block 205, where the misjoin correction module 116 receives input scaffolds. For the sake of generality, the inputs are referred to as scaffolds. The input may be a scaffold, that is sequence that are permitted to contain gaps, or the input may be contigs which comprise gap-free sequences. Input scaffolds may come from a variety of sources and technologies. In certain example embodiments the scaffolds are generated from Hi-C reads (5). In certain example embodiments, the input scaffold may be formatted as a fasta file. In certain example embodiment the input fasta file may comprise a duplicate-free list of paired alignments of Hi-C reads. In certain example embodiments, the pair-alignments of Hi-C reads may be generated by the Juicer pipeline (22).

In certain example embodiments, an optional preliminary filtration step may be used to remove scaffolds that due to their small size have relatively few Hi-C contacts, making them more difficult to reliably analyze. These are not processed further or included in the subsequent analysis. In certain example embodiments, scaffolds less than 15 kb and/or a N50 length of less than 6.1 kb are removed.

At block 210, the misjoin correction module 116, corrects misjoined sequencing reads in the input scaffolds. In certain example embodiments, the input scaffolds are examined for a signal consistent with a misjoin. Scaffolds with no evidence of a misjoin are labeled as 'consistent.' Scaffolds with evidence of a misjoin are partitioned into segments; each segment is classified as either a 'consistent' scaffold or an 'inconsistent' scaffold on the basis of the signal. Inconsistent scaffolds are not processed further. This portioning makes it possible to remove errors while retaining the portions of a scaffold that are correctly assembled for subsequent steps. Note that the terms above specifically refer to the results of the last round of misjoin correction, not the intermediate rounds. Block 210 is described in further detail hereinafter with reference to FIG. 3.

Methods 210 begins at block 305, where the misjoin correction module 116 initializes a scaffold pool using the set of input scaffolds received from block 205.

At block 310 the misjoin correction 116 module determines if there is at least one scaffold in the scaffold pool. If yes, the method proceeds to block 315. If there is not at least one scaffold in the scaffold pool, the method returns to block 215 of FIG. 2.

At block 315, the misjoin correction module 116 calculates an expected mode for contact frequency. When using DNA-DNA proximity reads, the method detects misjoins by relying on the fact that sequences that have been erroneously concatenated in a scaffold form fewer contacts with one another than correctly joined sequences. This is because correctly joined sequences lie adjacent to one another in 1D, and are therefore proximate to one another in 3D, facilitating the formation of DNA-DNA contacts. Because they do not actually lie in close proximity in the one-dimensional sequence of the chromosome, misjoined sequences usually do not exhibit similar 3D proximity or similar contact frequency.

To detect this depletion in contact frequency, one must compare the observed contact frequency between adjacent genomic loci with an expected model that describes the contact frequency typically observed for correctly joined sequences. Given a genome assembly with chromosome-length scaffolds, calculating the expected frequency of contact for a typical pair of sequences at a particular distance during a given experiment is straightforward. (4).

However, the results of such contact probability calculations are influenced by disparate factors, ranging from the organism of interest, the cell population interrogated, the details of the experimental approach, the particular computational methods used to analyze the data, and seemingly random inter-experimental variability. For this reason, expected models derived from a particular experiment in a particular cell population in a particular organism cannot be reliably applied to all experiments in all cell populations in all species. Thus, in the absence of a genome assembly with chromosome-length scaffolds, it is unclear how to determine the relationship between contact probability and distance even if Hi-C data is available.

A second challenge is that the contact probability between a pair of loci varies greatly, with frequent "jackpot" effects where the number of contacts is markedly enhanced with respect to the background model. This variability makes raw contact probability a very noisy indicator of the presence of a misjoin.

To overcome these challenges, the methods disclosed herein may estimate a contact probability, as a function of genomic distance, using data from a Hi-C experiment without utilizing a high quality genome. Instead, the embodiments disclosed herein only assumes the availability of a collection of scaffolds that may be short and contain numerous errors. Specifically, it is shown that, even in this scenario, it is possible to calculate a lower bound for the expected number of contacts between a pair of loci at a given distance. The estimation scheme relies on the fact that the frequency of contact between a pair of loci tends to decrease as the 1D distance between the loci increases. For this reason, pixels closer to the diagonal of a Hi-C matrix (which reflect contact frequency between loci that are nearby in 1D) tend to have higher contact counts than pixels further away from the diagonal.

Figure 37:
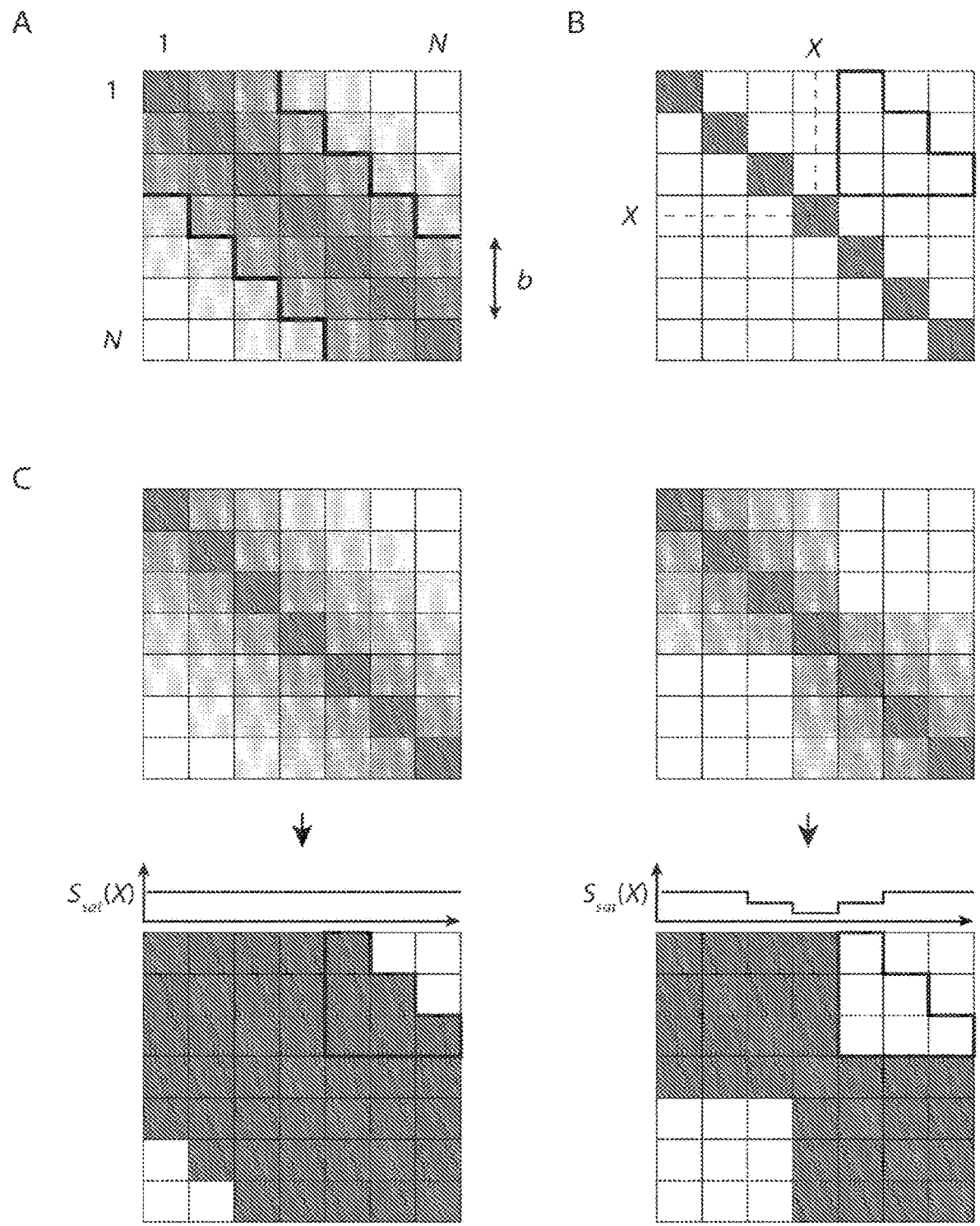
FIG. 37—Shows misassembly detection and algorithm. (A) Calculating the number of bins in between the diagonals from $c_{1+b,1}$ to $c_{N,N-b}$ and from $c_{1,1+b}$ to $c_{N-b,N}$. (B) Triangular shape used to calculate the scores $S(X)$ and $S_{sat}(X, r)$ along the assembly. (C) Schematic representation of matrix saturation and the distribution of the score $S_{sat}(X, r)$, along the genome. Bright red signifies the highest scoring bin in a given matrix.

Consider a N×N Hi-C contact matrix M generated using a known, correct reference genome (FIG. 37). To do so, the genome has been partitioned into N loci of fixed length that is matrix resolution r (measured in base pairs). Each pixel $M_{ij}$ corresponds to all contacts between a pair of loci (in this case, the $i^{th}$ locus and the $j^{th}$ locus). N is simply the genome length divided by the matrix resolution, r. Note that, in such a setting, it is often convenient to measure 1D distance in terms of loci (which are all of fixed size r), which correspond to rows and columns of the matrix, rather than in terms of base pairs.

In such a matrix, the set of pixels that derive from pairs of loci that are within b loci of one another may be considered, i.e. the pixels $M_{ij}$ such that (i−b≤j≤i+b). A principal goal is to estimate the function Q(b), which is the minimum value of all these pixels: Q(b)=min $M_{ij}$, i−b≤j≤i+b. This function provides a lower bound for the values $M_{ij}$ for pixels within b of the diagonal. Q(b) is useful in identifying misjoins, for the following reason: if the Hi-C data is aligned against an incorrect reference genome, containing numerous misjoins, the presence of a value lower than Q(b) within b pixels of the diagonal would indicate the presence of a misjoin at that position with complete certainty.

Before addressing the estimation of Q(b) in the general case, it is worth considering an idealized example. In FIG. 37 (A) an idealized Hi-C matrix M' is shown where contact probability decreases monotonically as the distance between a pair of loci increases, and the shape of this decay does not vary across the genome.

Notably, in such a matrix, the fraction of pixels $M_{ij}$ that derive from pairs of loci that are within b loci of one another (i−b≤j≤i+b) can be calculated by simply summing the lengths of the principal diagonal and 2×b non-principal diagonals, and dividing by the size of the matrix as a whole (N^2). This yields:

$$F(b)=N+b*(2N-b-1)N^2$$

Thus, if a pixel is selected from the matrix M at random, the probability that the pixel lies within b loci of the diagonal is exactly F.

Similarly, it is possible to determine the probability that a random pixel in the matrix contains a value larger than any arbitrary threshold C, denoted F'(C), by simply counting the number of pixels that contain more than C contacts and again dividing by the size of the matrix (N^2).

It is therefore possible to define a function C(b) so that F'(C(b))=F(b). In other words, C(b) is the number of contacts such that the fraction of pixels in M that is larger than C(b) is the same as the fraction of pixels in M that are within b of the diagonal. Furthermore, in an idealized Hi-C matrix such as the one shown in FIG. 37 (A), the pixels that lie within b of the diagonal will be exactly the pixels whose contact count is larger than C(b).

It follows from the above that—for an idealized, perfectly monotonic Hi-C matrix—Q(b) and C(b) are exactly the same function.

In practice, this is relevant because, like the contact probability scaling, Q Q(b) can be challenging to reliably estimate without an accurate genome assembly including chromosome length scaffolds. By contrast, F(b) can be calculated analytically using the formula above, without any experimental data at all.

Moreover, F F'(C) can be estimated for a given Hi-C experiment even assuming that a genome assembly with chromosome-length scaffolds is not available. In fact, F F'(C) can be accurately estimated using almost any reference genome assembly, so long as the effective scaffold N50 is much larger than the matrix resolution r.

A simple way to see why is that one can generate a proxy for the actual reference genome by concatenating all of the available scaffolds in an arbitrary order. In this proxy genome, the relative order and orientation of loci of size r will be entirely wrong. Nevertheless, most individual loci in the proxy genome will have a counterpart, containing the same sequence and having exactly the same size, in the true (albeit unknown) genome. For this reason, the vast majority of pairs of loci in the proxy genome will correspond to a pair of loci in the true (albeit unknown) genome. Thus, a Hi-C matrix generated with the proxy genome can be thought of as a permutation of the pixels of the Hi-C matrix that would be generated with the true genome. Consequently, the distribution of pixel values F'(C) is unaffected by the use of a scrambled proxy genome. (Note that in practice F'(C) can also be calculated from a raw scaffold set, without concatenation.)

Given estimates for F'(C) and F(b), estimating C(b) is straightforward. Thus, it is possible to estimate C(b) even with a relatively poor, and error-prone, input genome. Although C(b) is not identical to Q(b) for a real Hi-C matrix, it nevertheless provides a serviceable estimate for Q (b). For this reason, C(b) is useful in detecting misjoins.

At block 310, the misjoin calculation module 116 detects misjoins using the expected model derived at block 305. In certain example embodiment, misjoins are detected as follows. Consider a fragment of the Hi-C map shown in FIG. 37(B). One possible misjoin score would be to place a triangular motif along the diagonal, summing the values of the pixels it contains to create a score associated with the particular genomic position:

$$S(X)=\Sigma_{i=X-d}^{X-1}\Sigma_{j=X+1}^{i+d-1}c_{ij}$$

This score reflects the average contact frequency between a particular index locus being examined (X), and all other loci within d of the index locus. If the value of the misjoin score S is anomalously low, it suggests that the corresponding index locus spans a misjoin. Unfortunately, there is not simple and reliable way to calculate an expected value for this particular score. Thus, it is impossible to known whether the score is indeed anomalously low. Moreover, this score is extremely sensitive to "jackpot" effects, when a pixel with an anomalously high value (such as a loop or an alignment error) falls within the triangular motif.

By contrast, consider a slightly modified misjoin score. The score is calculated exactly as before, but with one change. Before calculating this score, we will apply a threshold C* to the Hi-C heatmap, such that, whenever the value of a pixel is larger than C*, the method will change that value to exactly match C*. Furthermore, the ability to calculate C(b) may be exploited as a proxy genome in order to select C* to be much less than C(d), such that nearly all pixels in the triangle motif shown will have a value equal to C* in the saturated matrix—except in the case of a misjoin. When combined with an ability to calculate C(b) for a low quality genome, this saturation step makes it simple to calculate an expected value for the misjoin score. Now the following for the saturated score $S_{sat}(X)$ and the expected value can be obtained (see FIG. 37(C))

$$S_{sat}(X)=\Sigma_{i=X-d}^{X-1}\rho_{j=X+1}^{i+d+1}\min(c_{ij}, C^*);$$

$$S_{sat}^{ex}=\Sigma_{i=X-d}^{X-1}\Sigma_{j=X+1}^{i+d+1}C^*=d^*(d+1)^*C^*/2.$$

On this basis, a locus is annotated as a putative misjoin whenever the misjoin score for that locus satisfies $S_{sat}(X)<k^*S_{sat}^{ex}$, where k is an arbitrary stringency parameter such that 0≤k<1. The availability of a reliable expected model greatly improves the sensitivity and specificity of such an approach. The approach is also much less susceptible to errors due to "jackpot" effects, since the impact of a single pixel is greatly dampened by the saturation step.

Note that, so long as C*<C(d), there is considerable latitude in selecting C*. In practice, since the function C(b), can only be estimated, rather than exactly calculated, it is useful to use C(d) as an upper bound for C*, but to choose values that are smaller, such as C(2*d). In the assemblies performed here, C* is set to equal the 95th percentile of all nonzero pixels in the contact matrix.

At block 315, the misjoin correction module 116 localizes the detected misjoins. In certain example embodiment misassembly detection is performed using two different values of the matrix resolution r. First, misassemblies are annotated at coarse resolution (r=25 kb), to eliminate noise. In areas flagged by the coarse resolution detection, the exact position of the misassembly is localized by repeating the procedure of block 310 at a higher matrix resolution (r=1 kb). This approach achieves high positional accuracy in misjoin identification.

The misjoin detection step is not performed directly on individual input scaffolds. Both misjoin detection and C(b) estimate are more accurate the longer the effective N50 of the input scaffolds. Moreover, misjoin detection is significantly less sensitive if the effective N50 is less than d×r. For this reason, the effective N50 of the scaffold set is maximized by running the scaffolding module 117 described further below on the input scaffolds prior to misjoin detection. The input scaffolds are embedded in the resulting output scaffold, and thus misjoins detected in this output scaffold can be associated with misjoins in the input scaffolds.

At block 320, the misjoin correction module 116, classifies the detected misjoins based on whether the misjoin lies inside one of the input scaffolds—implying that there is an error in the input scaffold, which needs to be corrected—or whether the misjoin lies at the junction between the two scaffolds, suggesting that the misjoin is a consequence of an error in the input sequence located at a different position.

Figure 38:
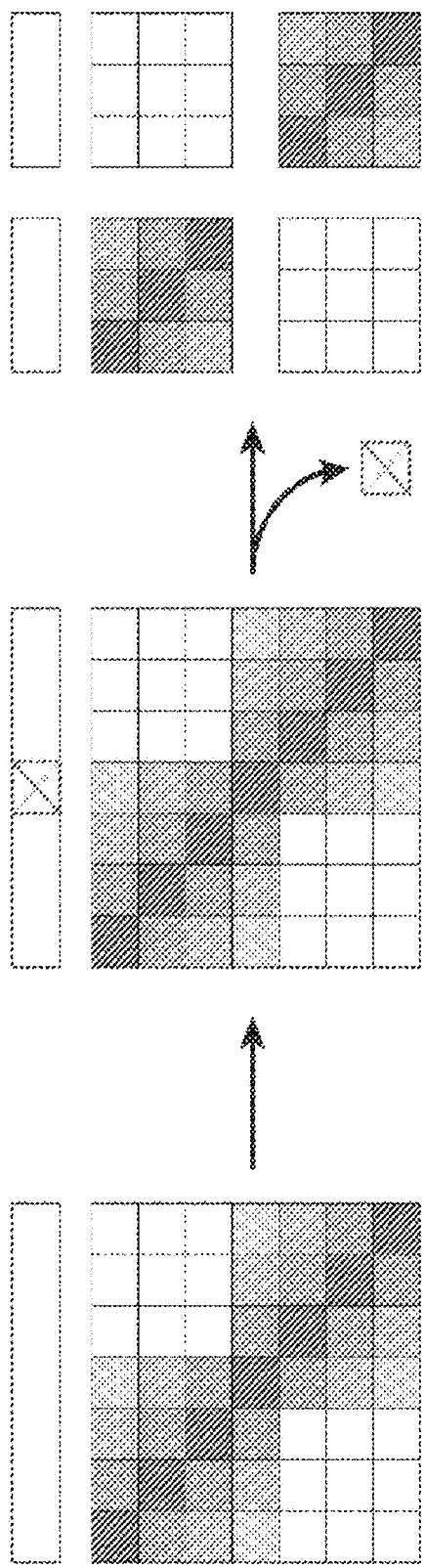
FIG. 38—Shows misassembly correction. Once a problematic region is identified that lies outside an input scaffold (a bin marked with an X), the region gets excised resulting in two internally consistent fragments of the original input scaffold. The third fragment that spans a misassembled region is labeled as inconsistent. Inconsistent fragments do not participate in the next round of scaffolding.

If a misjoin lies inside a scaffold, the scaffold is edited by excising sequence intervals flagged by the misjoin detection module 116 (see FIG. 38). The excised fragment is labeled as an additional, 'inconsistent' scaffold and excluded from subsequent assembly iterations, since its continued presence during the scaffolding process could lead to further misjoins. If the misjoin is sufficiently far from both ends of the scaffold, this results in splitting the affected scaffold into two scaffolds at the site of the misjoin (in addition to the formation of an inconsistent scaffold). Note that multiple misjoins can be identified in a single scaffold during a single round of misjoin detection, which could lead to repeatedly splitting one scaffold into multiple smaller scaffolds.

The Method 210 can be described using the following pseudocode:

---
Misassembly correction:
---
1) Calculate C(b) for the contact matrix at a coarse resolution $r_1$
2) Computer the saturated score functions $S_{sat}(X, r_1)$ at the course resolution
3) Calculate C(b) for the contact matrix at fine resolution $r_2$
4) Compute the saturated score function $S_{sat}(X, r_1) < k * S_{sat}^{ex}$
5) For each misjoined locus identified:
   a) Localize the misjoin at resolution $r_2$ by finding the minimum of $S_{sat}(X, r_2)$ in the locus
   b) Compare the localized misjoins with scaffold boundaries to distinguish scaffolds containing misjoins from misjoins that lie between scaffolds
   c) Correct the input scaffolds by excising misjoins inside scaffolds and labeling the excised fragment as inconsistent; in addition, if the misjoin is far from the ends of the scaffold, divide the input scaffold into two scaffolds by splitting at the misjoin site
---

Figure 39:
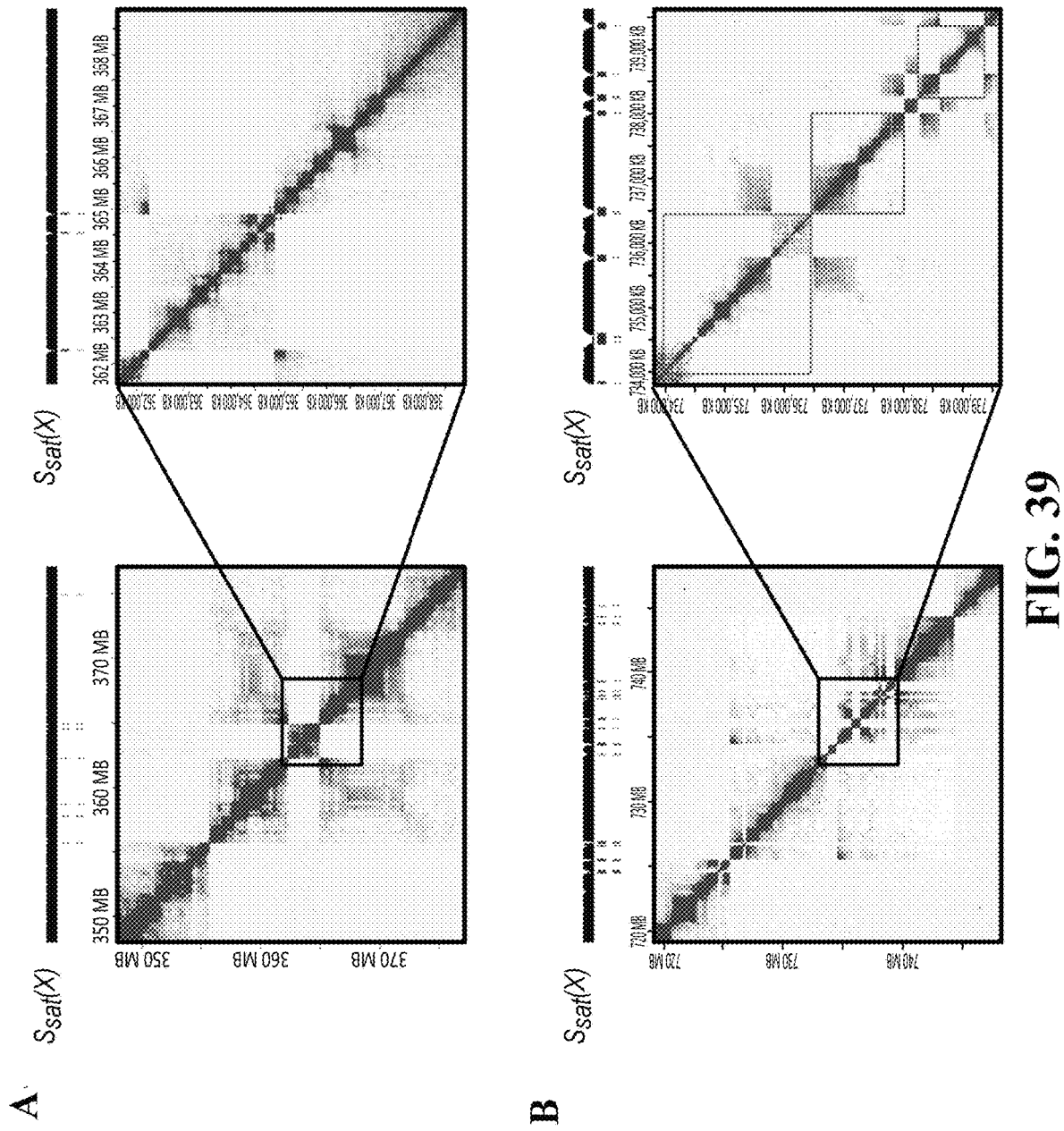
FIG. 39—Shows misassembly detection algorithm performance on Hs1 (A) and AaegL2 (B) input. Left panel shows a fragment of the Hi-C map for the assembly obtained by scaffolding the original input scaffolds, without any editing. The tracks on top of the map show the distribution of S!"# X, r!)) along the assembly (blue) as well as coarse (top green track) and fine (bottom green track) positioning of misassembled sequences as identified by the misassembly detector. Right panel shows a zoom-in on a fragment of the map with input scaffold boundaries superimposed to assist in classifying the detected misassemblies. Intrascaffold misassemblies constitute a list of edits to be applied to the original scaffold set; misassemblies that overlap with scaffold boundaries are ignored. There is one intrascaffold misassembly in Hs1 and 5 intrascaffold misassemblies in AaegL2 in the corresponding fields of view.

Overall, the misjoin detection method 210 is characterized by low false positive error rates and accurate localization. It is especially sensitive to large misassemblies that give rise to large-scale errors in the genome. Several examples of automatic misassembly detection are given in FIG. 39.

Returning to FIG. 2 at block 215, where the scaffolding module 117 generates a megascaffold. Block 215 is described in greater detail with reference to FIG. 4

To transform a set of input scaffolds into chromosome-length scaffolds, three problems must be solved. "Anchoring" assigns each scaffold to a chromosome, thus partitioning the set of scaffolds into multiple subsets. "Ordering" assigns a relative position to each scaffold on each chromosome with respect to the other scaffolds assigned to the same chromosome. "Orienting" determines which of the two ends of each scaffold is adjacent to the preceding scaffold in the ordering, and which end is adjacent to the next scaffold in the ordering. (This step is equivalent to assigning each scaffold to one of the two complementary strands that comprise a chromosome.) Our algorithm for constructing chromosome-length scaffolds begins with a set of input scaffolds, and simultaneously anchors, orders, and orients them.

Method 215 may be iterative; the same steps are performed over and over, often thousands of times. In each step, subsets of the input scaffolds are ordered and oriented with respect to one another to create a new, longer set of scaffolds, which are then used as inputs for the next step. For the remainder of this section, we will use the term "input scaffolds" to refer to the scaffolds which are the inputs to each step; when needed, will the term "initial input scaffolds" will be used to refer to the scaffolds which are the inputs to the iterative algorithm as a whole.

Method 215 begins at block 405, where the scaffold module 117 initializes the scaffold pool with a set of input scaffolds. The scaffold module 117 splits each input scaffold into two "hemi-scaffolds" by bisecting the scaffold sequence at the midpoint. The pair of semi-scaffolds that derive from a single hemi-scaffold are dubbed "sister hemi-scaffolds."

Figure 40:
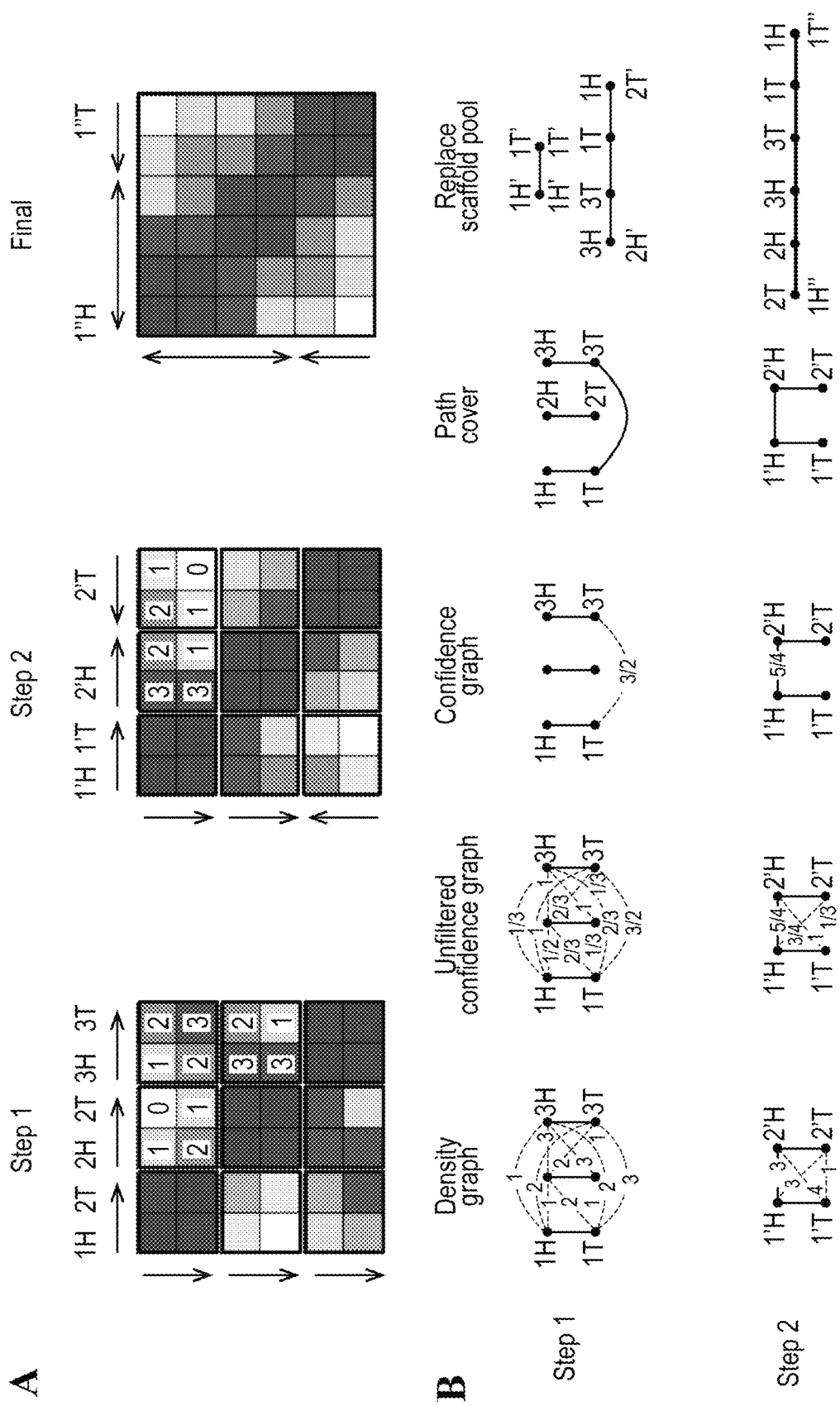
FIG. 40—Shows an example of applying an iterative scaffolding algorithm to a mock Hi-C dataset. The input scaffold pool consists of three scaffolds: 1, 2 and 3. The scaffolds are split into hemi-scaffolds. (To be able to distinguish between the hemi-scaffolds one is annotated as H for head and T for tail. The choice in each case is arbitrary.) The number of pairwise Hi-C contacts observed between all loci in all scaffolds is given as a Hi-C contact map. The assembly finishes in two steps. We show the intermediate results for both steps: density graph, unfiltered confidence graph, confidence graph, path cover and redefinition of scaffold pool. Note that to reduce cluttering the weights on the density graph are given without normalization. For the same reason the weights of sister edges are not shown in the density and confidence graphs; instead the sister edges are marked with black color.

At block 410, the scaffolding module 117 constructs a density graph for the scaffolds in the scaffold pool. For the density graph S, each hemi-scaffold is represented as a single vertex. The edges to the density graph are appended as follows. See FIG. 40.

First, edges between all pairs of vertices are appended that do not correspond to sister hemi-scaffolds. Theses edges are referred to as "non-sister" edges. The weight of each non-sister edge corresponds to the density of the DNA-DNA contacts between the corresponding hemi-scaffolds. To calculate this density (i.e. edge-weight), the count number of contacts where one read is incident on one of the hemi-scaffolds, and the other read is incident on the other hemi-scaffold may be used. The resulting value is then divided by the product of the sequence length of the two hemi-scaffolds to arrive at the density. Not that, all else being equal, having an edge of greater weight between two hemi-scaffolds indicates that the two hemi-scaffolds tend to be more proximate in 3D, and thus are more likely to be nearby along the one-dimensional chromosome sequence as well. The edges may then be appended between all pairs of vertices that correspond to sister hemi-scaffolds. All of these edges are assigned a weight of 2*MAXS, where MAXS is the maximum weight of all of the non-sister edges. This is done in order to encode the fact that sister hemi-scaffolds are adjacent to one another according to the input scaffold set, and that this evidence is—during each scaffolding iteration—regarded as more reliable than any evidence derived from DNA-DNA contacts. Of course, method 210 describes strategies for correcting scaffolds using DNA-DNA contact data. The results of these strategies influence the input scaffold set for any given step of the method 215. However, within the individual iterations, the accuracy of the input scaffold set is regarded as a constraint that takes precedence of the DNA-DNA contact data.

Prior approaches for scaffolding using DNA-DNA contact data relied directly on measures of contact density. This approach is error-prone. For instance, high-coverage scaffolds, scaffolds containing loci engaged in strong long-range interactions, scaffolds containing repeat sequences, etc. might all display frequent contacts with scaffolds that are far away from them along the 1D chromosome sequence. Conversely, input scaffolds from low-coverage regions of the genome might exhibit a relatively low contact density, even with scaffold that are adjacent to them in 1D.

In order to reliably determine the relative positioning and orientation of scaffolds given these potential pitfalls, the embodiments disclosed herein utilize a process for identifying adjacent scaffolds that is not directly based on absolute read density. A pair of input scaffolds are considered "adjacent" if they are on the same chromosome, and no other input scaffold has a true genomic position that lies on that same chromosome in between them.

To accomplish this, at block 415, the scaffolding module 117 uses the density graph to define an unfiltered confidence graph C'. The vertices of the unfiltered confidence graph again correspond to the hemi-scaffolds. The edges of the unfiltered confidence graph are defined as follows. See FIG. 40. If A and B are not sister homologs, then an edge is appended between them whose weight is the ratio of the weight of the edge connecting them in the density graph (sAB), and the weight of the second-largest non-sister edge incident on either A or B in the density graph. Note that cAB>1 if an only if there is no hemi-scaffold whose contact density with either A or B exceeds the contact density between A and B. Informally, this means that, based on the contact density data, A is the best partner for B, and B is also the best partner for A. Edges whose weight is greater than 1 are considered "reliable." Edges whose weight is 1 or smaller are called "unreliable."

Next, edges are appended between all pairs of vertices that correspond to sister hemi-scaffolds. All of these edges are assigned a weight of 2*MAXC, where MAXC is the maximum weight of all of the non-sister edges in the unfiltered confidence graph. This is done in order to encode the fact that sister hemi-scaffolds are adjacent to one another according to the input scaffold set, and that this evidence is—during each scaffolding iteration—regarded as more reliable than any evidence derived from Hi-C.

At block 420, the scaffolding module 117 determines if the confidence graph does not contain edges linking hemi-scaffolds from distinct scaffolds in the pool ("non-sister edges"). If non-sister edges are present, the method proceeds to block 430. If non-sister edges are not present, the method proceeds to block 435.

If all non-sister edges are unreliable, then the iteration has failed in the sense that no reliable adjacency information could be extract from the contact density data. Therefore, if all the non-sister edges are unreliable, at block 425, the scaffolding module 117 removes the smallest scaffold in the scaffold pool, and the method 215 reiterates through steps 410-420 again. In certain example embodiments, step 405 is also repeated. Note that removing the smallest input scaffold and repeating the step might still not yield a reliable edge, in which case another scaffold is removed, and so on. Eventually, either a reliable edge will be found or there will only be one scaffold left (at which point the method halts and outputs the remaining scaffold).

Assuming there is a reliable non-sister edge in the unfiltered confidence graph, at block 420, the scaffolding module 117 filters the unfiltered confidence graph by removing all edges whose weight is less than or equal to 1. The resulting graph is called the confidence graph. Note that every vertex is adjacent to one sister edge in the confidence graph, and to at most 1 non-sister edge. Thus, all vertices in the confidence graph have either degree 1 or degree 2. Hence, the confidence graph is a collection of disjoint paths and cycles. Vertices that are adjacent in the confidence graph are very likely to correspond to hemi-scaffolds that are adjacent in 1D. Therefore, each path in the confidence graph corresponds to a high-confidence scaffold. Furthermore, each path in the confidence graph whose length is greater than 2 corresponds to a new scaffold comprised of multiple input scaffolds whose relative order and orientation have been determined using DNA-DNA proximity ligation assays.

Cycles in the confidence graph contain multiple possible paths (i.e. new scaffolds) spanning all the vertices (hemi-scaffolds) in the cycle. Here the key is to identify the maximal path contained in the cycle, which corresponds to the new scaffold in which the highest confidence is available given the contact density data. The can be accomplished by removing the edge in each cycle whose weight is the smallest. Because of how the confidence graph is constructed, this edge will always be a non-sister edge. IN graph theoretic terms, this procedure can be thought of as a way to construct the maximal—in terms of total edge weight—vertex-disjoint path cover of the confidence graph.

A complementary way of formulating this procedure (which is mathematically guaranteed to produce exactly the same output) is to greedily select the highest weight edges from the confidence graph, ensuring that no vertex in the graph will be incident on two or more edges. (This constraint is equivalent to the rule that, after selecting non-sister edge AB, we must remove all other non-sister edges incident on either A or B.) Following this procedure, a maximum weight vertex-disjoint path cover is eventually obtained. Notably, for the special case of confidence graphs, this complementary formulation is exactly equivalent to Kruskal's algorithm for constructing a maximal spanning forest (29). Because a confidence graph consists of disjoint paths and cycles, its maximal spanning forest is always a vertex-disjoint path cover.

Since vertices that are adjacent in the confidence graph are very likely to correspond to hemi-scaffolds that are adjacent in 1D, and since each path in the confidence graph corresponds to a high-confidence scaffold, the maximum weight vertex-disjoint path cover in the confidence graph corresponds to a new set of scaffolds that is optimal with respect to the input scaffolds and the contact density data. Thus, at block 435, the scaffolding module 117 defines one or more output scaffolds based on the confidence graph.

Once the output scaffolds are obtained, the iteration ends. Thus, at block 440, the scaffolding module 117 determines if more than one output scaffold in the scaffold pool. If there is more than one scaffold in the scaffold pool, steps 405-440 are repeated. The output scaffolds from the previous iteration can be used as input scaffold for the new iteration and the density and confidence graphs are constructed for the new inputs. Note that reconstructing the graph from scratch allows more contact density data spanning larger scales to be incorporated into the analysis. In certain example embodiments, an alternative to recalculating the density graph is to use a more permissive threshold for including edges in the confidence graph i.e. require cab>k, wherein k<1. This would allow more scaffolding information to be extracted at each step, and thus fewer steps would be required to complete the scaffolding procedure.

To summarize the above process may be executed the following example pseudocode:

| Scaffolding |
|---|
| Initialize the scaffold pool using a set of input scaffolds |
| While there is more than one scaffold in the scaffold pool: |
| a)    Construct the density graph for the scaffolds in the scaffold pool |
| b)    Transform the density graph into a confidence graph |
| c)    If the confidence graph does not contain edges linking hemi-scaffolds form distinct scaffolds in the pool ("non-sister edges"): |
|      i.      remove the smallest scaffold from the scaffold pool |
| d)    Else: |
|      i.      Find maximum weight of vertex-disjoint path cover of the confidence graph |
|      ii.      Determine the corresponding output scaffolds |
|      iii.      Replace the scaffold pool with the output scaffolds |

If the scaffolding module 117 determines there is only scaffold left, then the method returns to block 215 of FIG. 2

Figure 34:
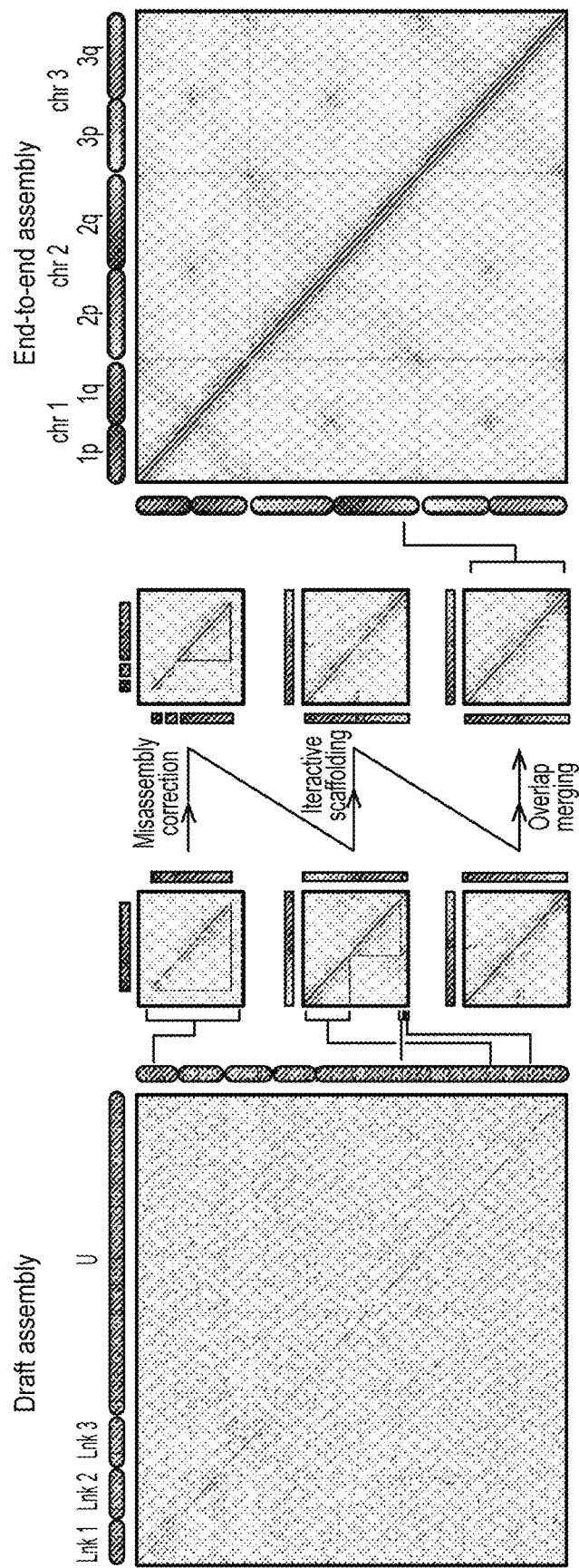
FIG. 34—Shows a draft assembly used to generate a chromosome-length scaffold using Hi-C vis misjoin correction, scaffolding, and merging of overlapping scaffolds. These three steps are illustrated with a scaffold from the AaegL2 assembly ('supercontig 1.12'). The scaffold is examined for misjoins and split into segments, each of which exhibits a continuous Hi-C signal. The segments are treated independently in an example iterative scaffolding step. One is placed on chromosome 1, and the rest on 2q. Segments exhibiting a similar 3D signal are examined for overlapping sequences and merged.
Figure 35:
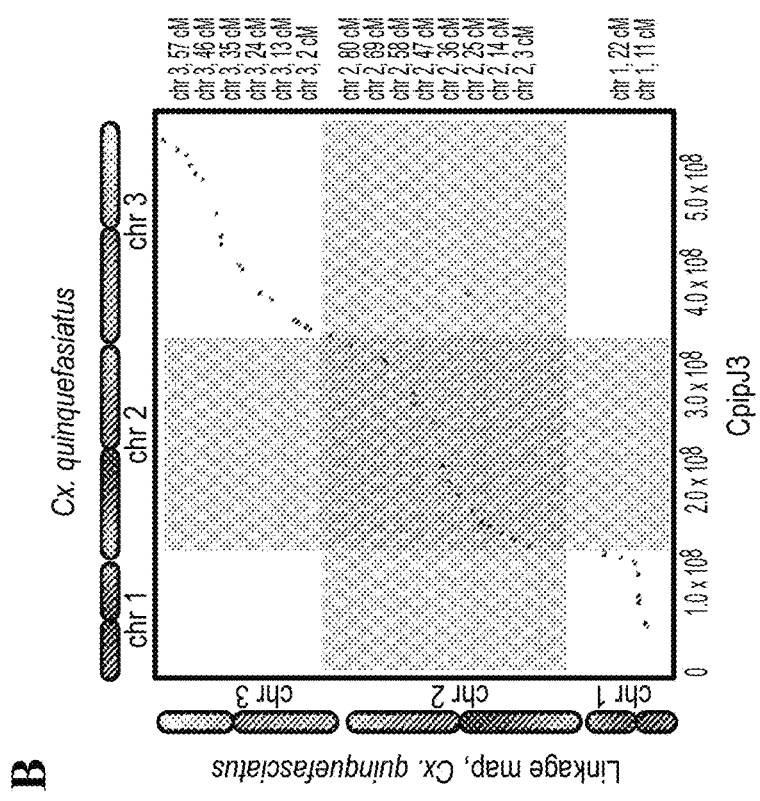
FIG. 35—Shows a comparison of AaegL4 and CpipJ3 with genetic maps. (A) compares AaegL4 with a genetic map of *Ae. aegypti* (19). The assembly agreed with the genetic map on 1822 of the 1826 markers. The exceptions are due to misjoins in AaegL2 that were not corrected in AaegL4. (B) Similarly, CpipJ3 is in agreement with a genetic map of *Cx. quinquefasciatus* (21).
Figure 35:
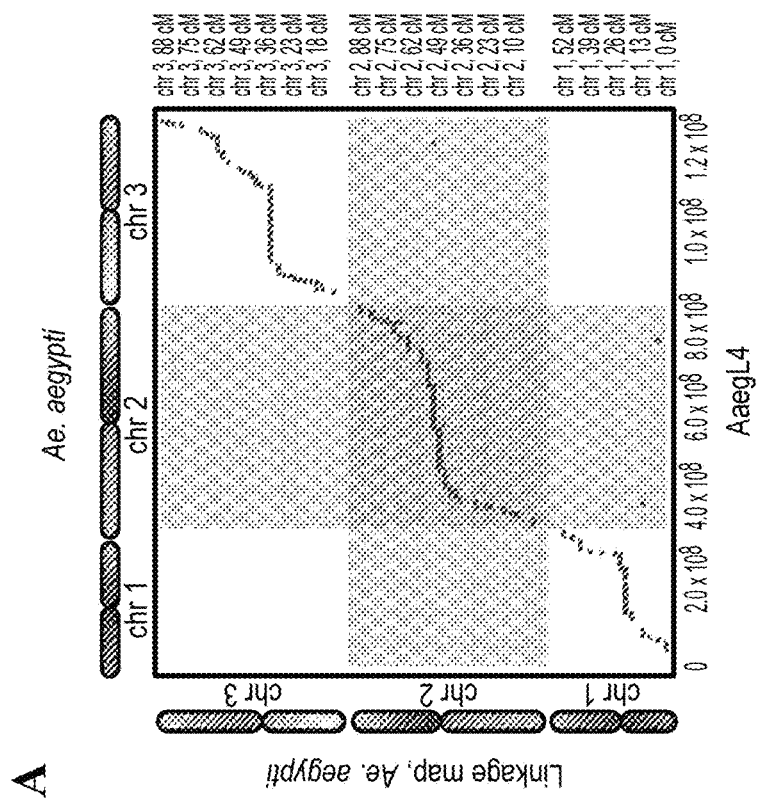
Figure 36:
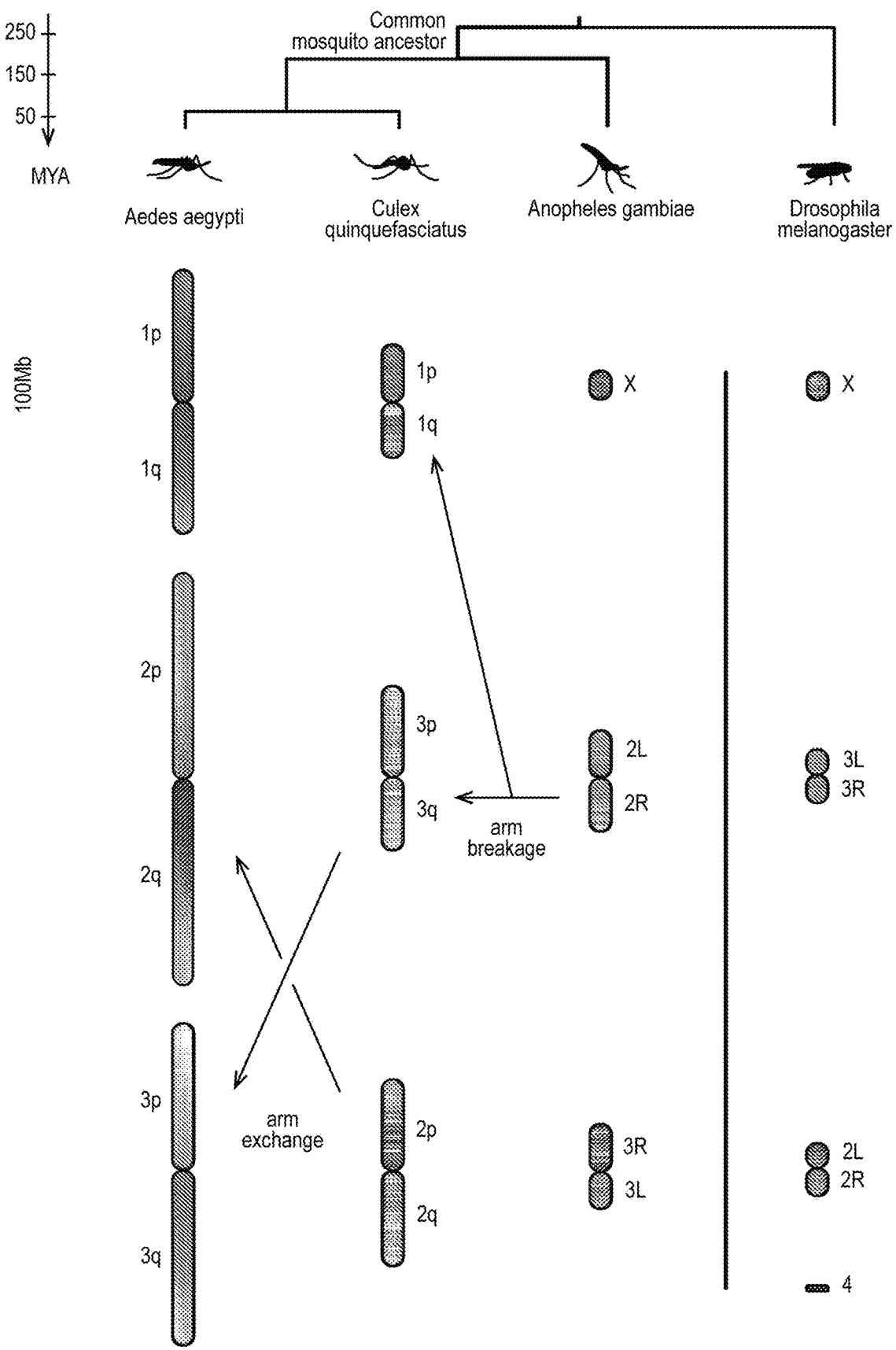
FIG. 36—Shows the content of chromosome arms is strongly conserved across mosquitoes. Here, each 100 kb locus in *Ae. aegypti* is assigned a color. For the other species, each 100 kb locus is assigned a combination of the colors of the corresponding DNA sequences in *Ae. aegypti*, weighted by length.
Figure 49:
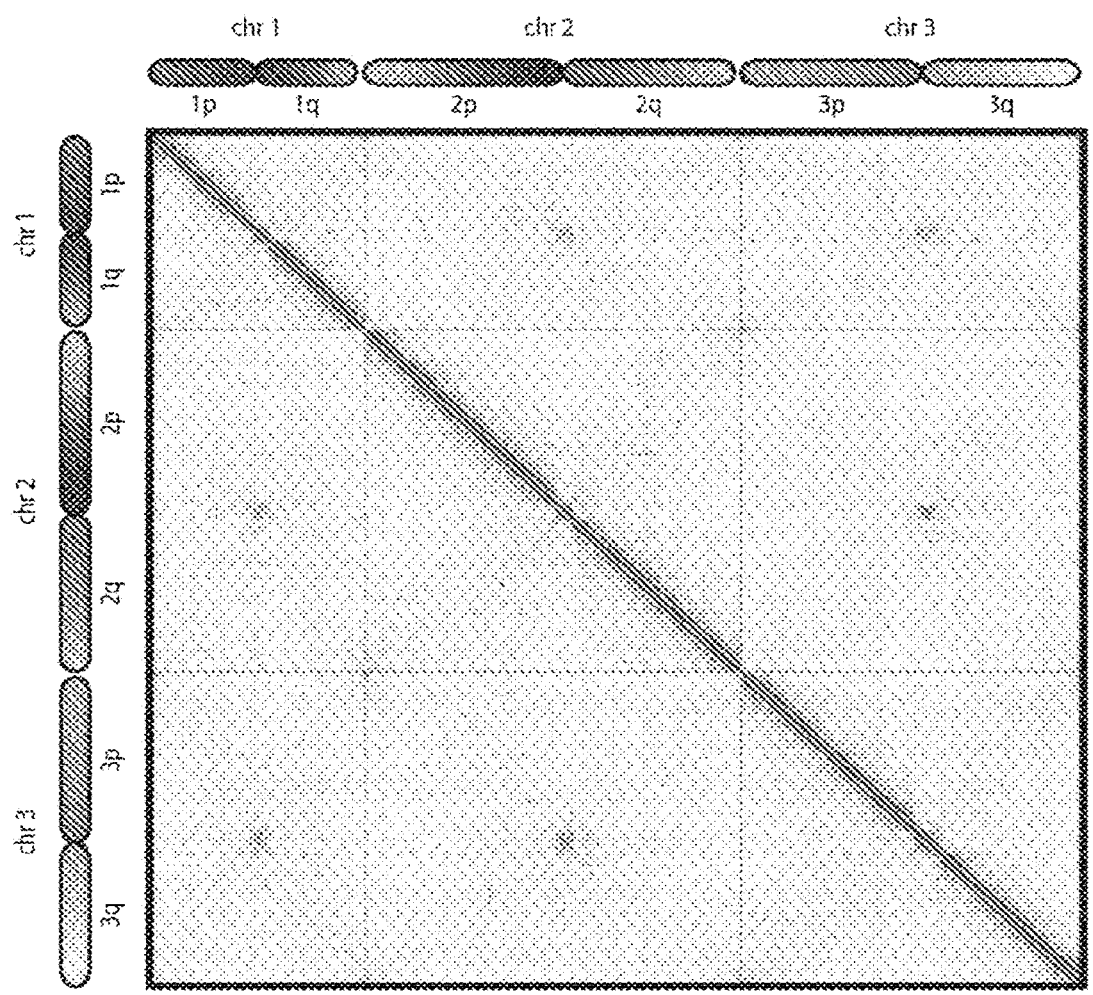
FIG. 49—Shows the 3D map of the *Cx. quinquefasciatus* genome. Both *Ae. aegypti* and *Cx. quinquefasciatus* genomes exhibit bright, off-diagonal peaks, which indicate the spatial clustering of telomeres and centromeres. These peaks facilitate the annotation of centromeric sequences for each chromosome (41).
Figure 50:
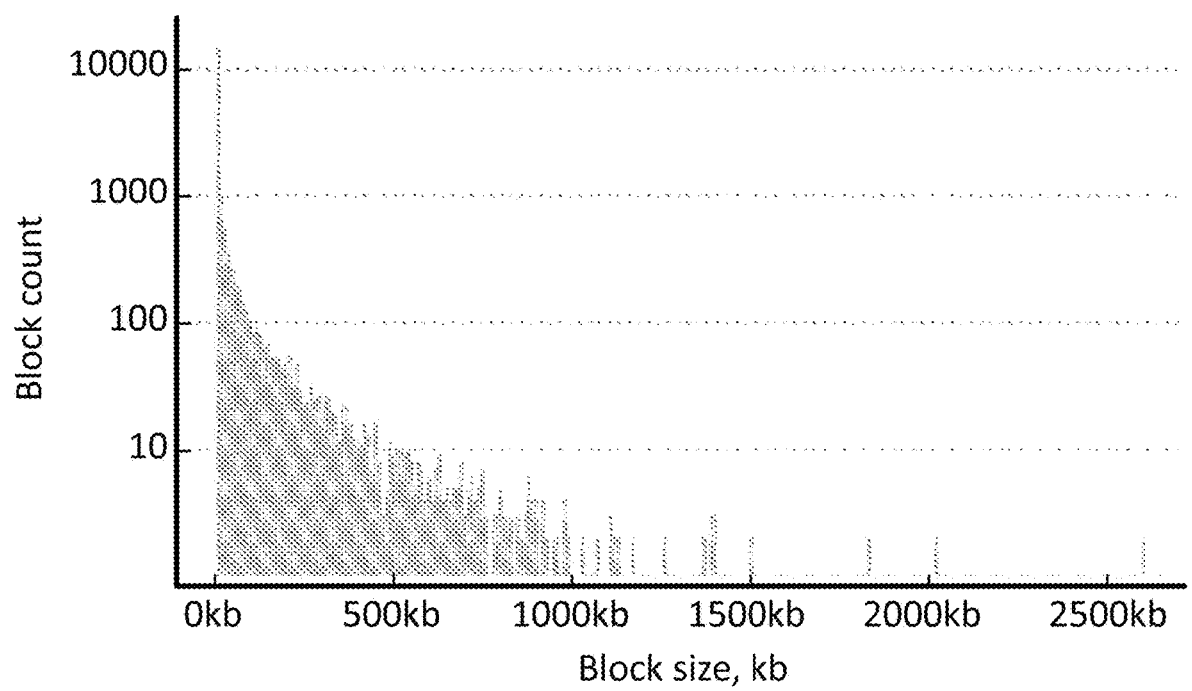
FIG. 50—Shows size distribution for synteny blocks between *Ae. aegypti* and *An. gambiae*. The block sizes are measured with respect to the *Ae. aegypti* genome. The blocks are defined as chains of conserved sequence markers that are both consecutive and collinear in both genomes. The chain ends when two consecutive markers disagree with the rest of the chain; however, one marker in the wrong order and/or the wrong orientation does not break the chain.
Figure 51:
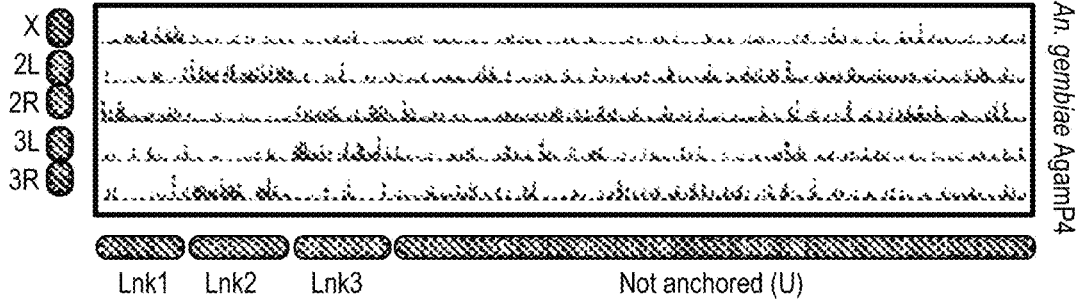
FIG. 51—Shows the AaegL4 genome assembly enables genome-wide analysis of conservation of synteny between *Ae. aegypti* and *An. gambiae*. (A) Density of conserved alignments between chromosomes of *Ae. aegypti* and *An. gambiae* as suggested by the AaegL2 assembly. Below the histogram tracks we show the linkage groups reported in AaegL2 (18). (B) The synteny analysis from panel A is repeated using improved linkage groups generated via physical mapping (36), which are indicated below the plot. (C) The synteny analysis from panel A is repeated using improved linkage groups generated via genetic linkage mapping (19), which are indicated below the plot. (D) Synteny analysis for the AaegL4 assembly. A one-to-one correspondence between the chromosome arms of *Ae. aegypti* and *An. gambiae* is apparent. Chromograms along the x- and y-axes indicate which portions of AaegL4 correspond to which positions in the other genomes and genome assemblies.
Figure 51:
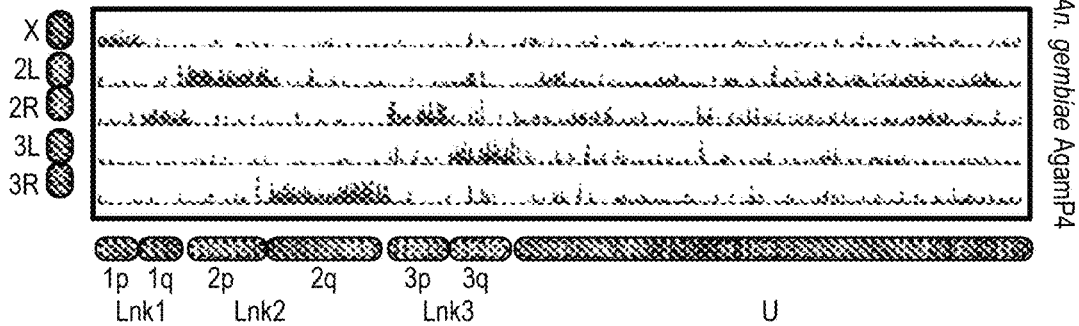
Figure 51:
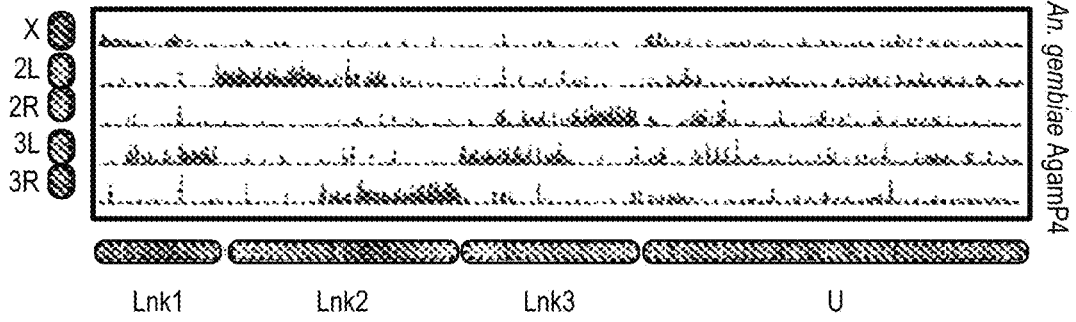
Figure 51:
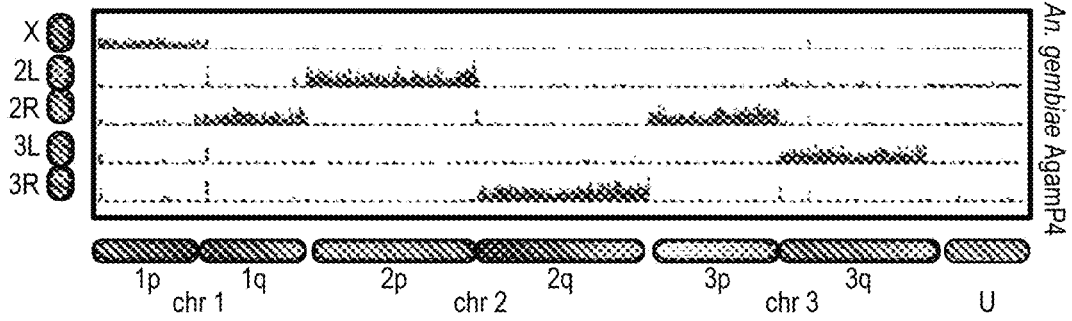
Figure 52:
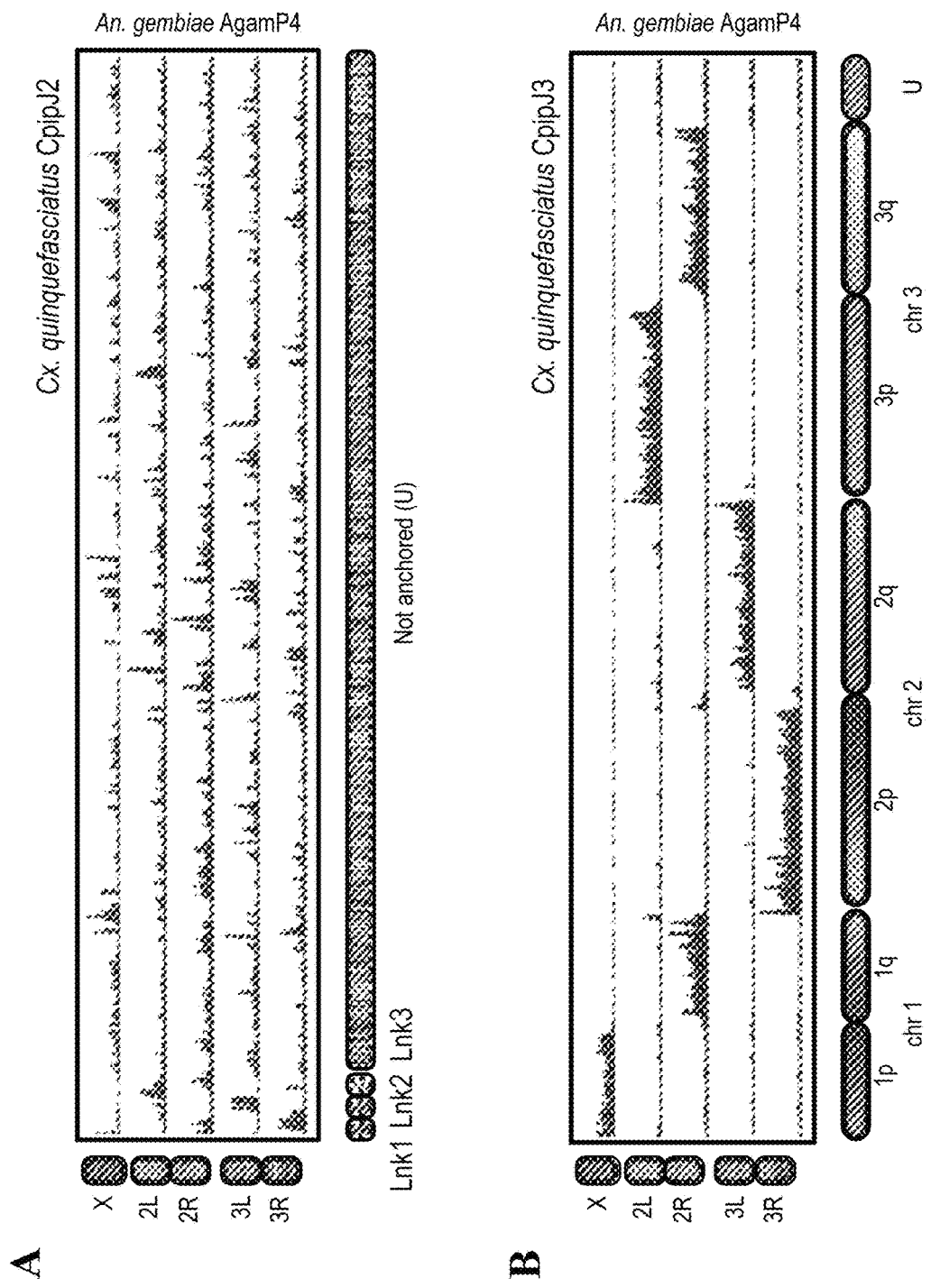
FIG. 52—Shows the CpipJ3 mapping reveals strong conservation of the contents of chromosome arms between *Cx. quinquefasciatus* and *An. gambiae*. A) Conservation of synteny between chromosomes of *Cx. quinquefasciatus* and *An. gambiae* as suggested by the CpipJ2 assembly. B) Conservation of synteny as represented by the CpipJ3 assembly. Chromograms along the x- and y-axes indicate which portions of CpipJ3 correspond to which positions in the other genomes and genome assemblies.
Figure 53:
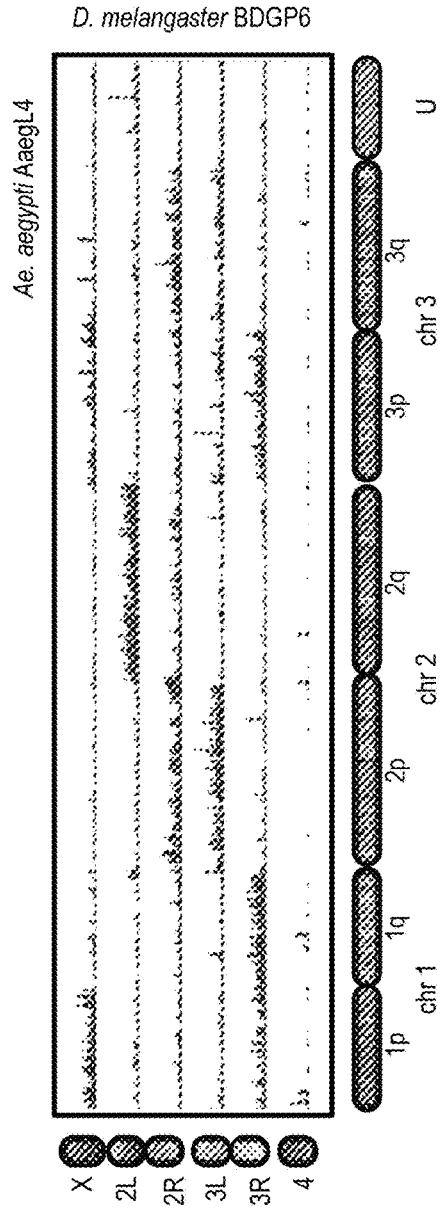
FIG. 53—Shows conservation of synteny across dipterans. Several chromosome arms, such as *D. melanogaster* 2L, *Ae. aegypti* 2q, and *Cx. quinquefasciatus* 2p, show strong conservation of content. Chromograms along the x- and y-axes indicate which portions of BDGP6 correspond to which positions in the other genomes and genome assemblies.
Figure 53:
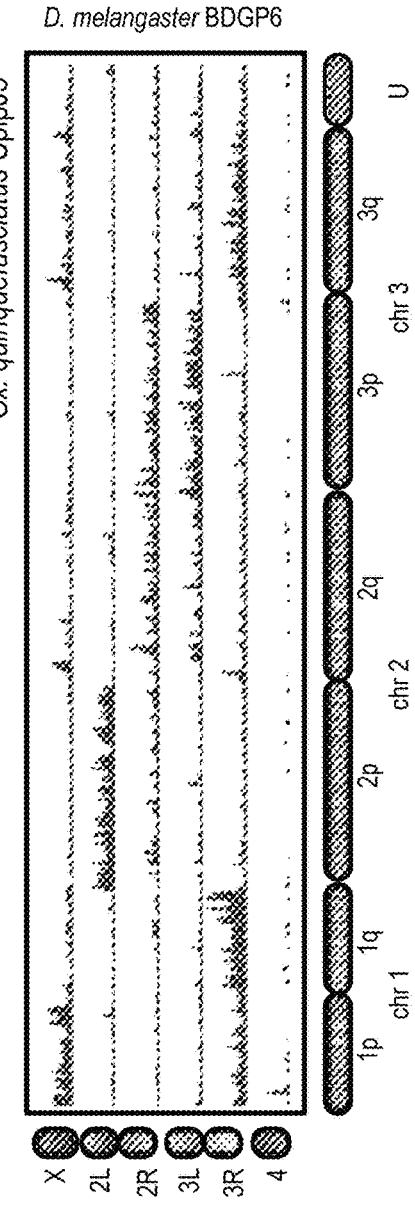
Figure 54:
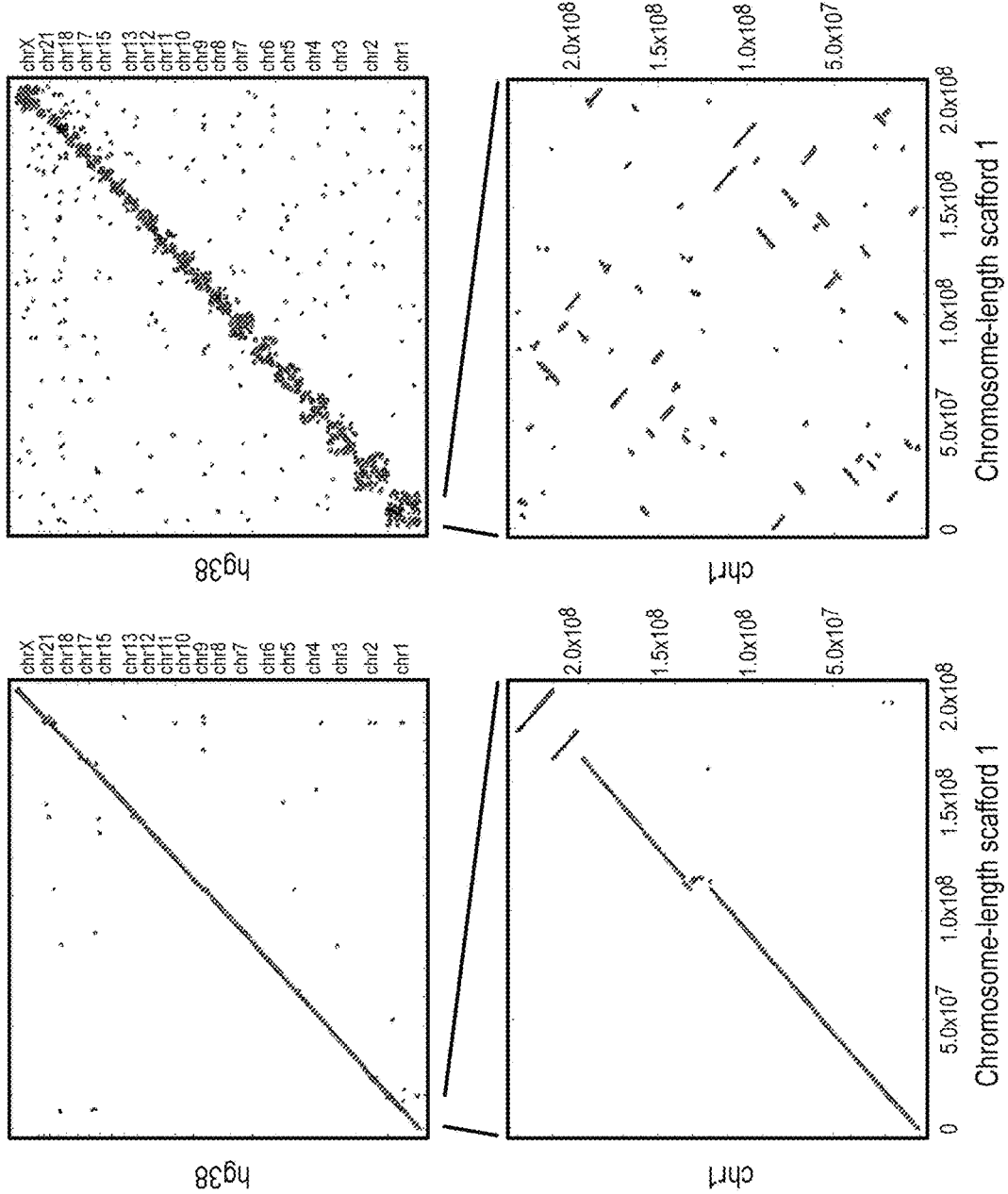
FIG. 54—Shows comparison of scaffolding algorithms presented in (10) and the current paper. Misassembly detection has been disabled in our pipeline to focus the comparison specifically on scaffolding abilities. The algorithms have been given the same data as input: set of DISCOVAR de novo scaffolds from 60× PE250 Illumina short reads and 6.7× of Hi-C data. In both cases only scaffolds longer than 20 kb have been used. Although clustering is clearly visible in the LACHESIS output individual chromosome-length scaffolds were not correctly reconstructed.
Figure 55:
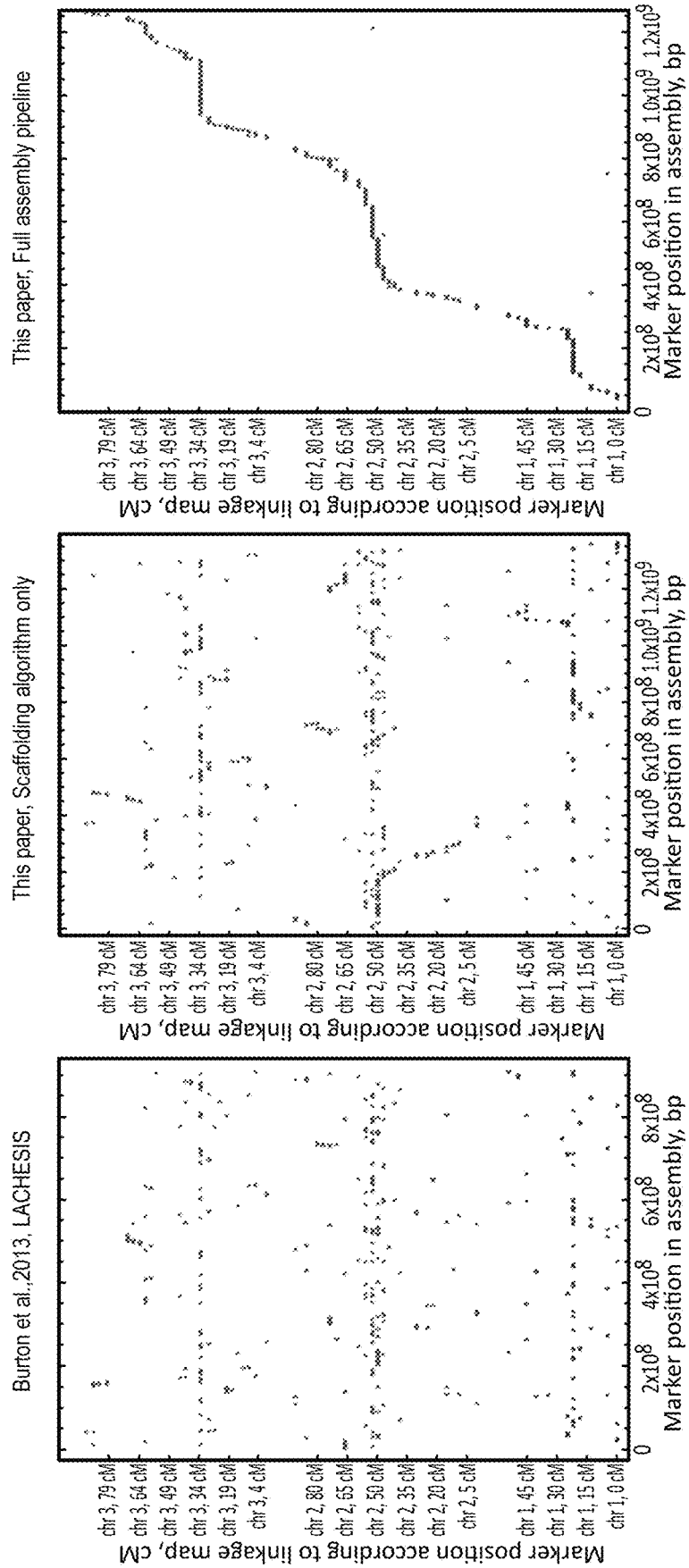
FIG. 55—Shows comparison of the results of running LACHESIS (10), our scaffolding algorithm (without misjoin correction), and our full pipeline (including misjoin correction) on AaegL2 with the existing linkage map (19).

Note that the embodiments disclosed herein do not rely on a preliminary contact density clustering step to identify chromosomes. Compare to (10). This is particularly useful for species like mosquito, where loci that lie far apart on the same chromosome may not exhibit enhanced contact frequency relative to loci on different chromosomes. See FIG. 34 and FIG. 49.

Returning to FIG. 2, the method 200 proceeds to block 220, where the polishing module 118, removes false positives. The polishing step is an optional step designed to address challenges associated with unusual 3D features that arise from organisms exhibiting strong telomere and centromere clustering. This can create false positive during scaffolding, since extremely strong off-diagonal 3D signals associated with telomere and centromere clustering can sometimes be strong enough to rival the contact frequencies observed for loci that are adjacent in 1D.

Figure 41:
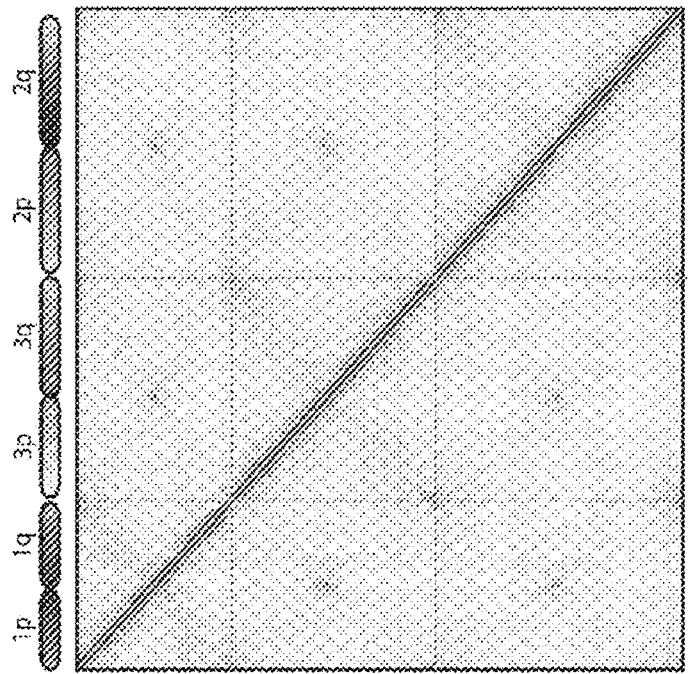
FIG. 41—Shows polishing the assembly during the construction of AaegL4 genome. Clustering of telomeres and centromeres can create false positives during scaffolding, since extremely strong off-diagonal 3D signals associated with telomere and centromere clustering can sometimes be strong enough to rival the contact frequencies observed for loci that are adjacent in 1D. Such errors are corrected by low-resolution misassembly detection and reassembly of the resulting multimegabase fragments.
Figure 41:
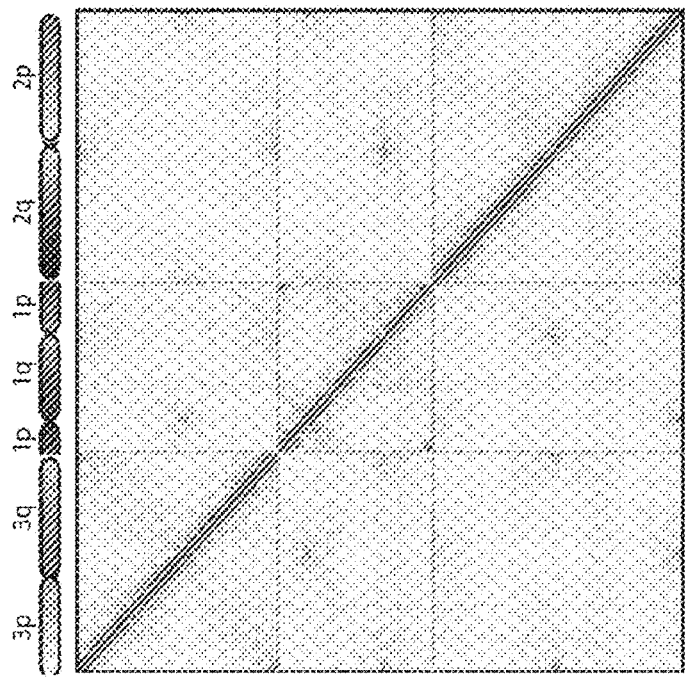

FIG. 41 shows a Hi-C contact map built with respect to the Ae. aegypti genome assembly before and after the polishing step. The map suggests that chromosome 3 is very accurately assembled, but chromosomes 1 and 2 contain a type of error that is characteristic of assembly in genomes that exhibit strong telomere-to-telomere clustering. In this error, the enhanced proximity between the two telomeres is mistaken for 1D proximity. As a result, the raw chromosomal scaffolds corresponding to chromosomes 1 and 2 exhibit a cyclic permutation with respect to the true chromosome.

As an example, if the sequence of the true chromosome was ABCDEFG, where locus A and G are telomeres, then the erroneous sequence might be DEFGABC. We call this sort of error a "cycle break." Note that, when a cycle break occurs, an off-diagonal peak linking the two putative ends of the chromosome (in the example, D and C) is still seen in the Hi-C map. However, this signal is actually due to the true 1D proximity between the two ends of the putative chromosome, rather than at true 3D signal. Conversely, the on-diagonal signal between A and G, which appears to reflect 1D proximity, is in fact due to the telomere clustering. (Similar errors may arise due to strong interaction between telomeres of two different chromosomes. They are addressed in the same way. See FIG. 41, chromosomes 2 and 3.)

The polishing module 118 can correct such errors by a single additional round of misjoin correction, performed at extremely low resolution (r~1 Mb). The low-resolution misassembly detection identifies reliable "superscaffolds", each of which is many megabases in length. These superscaffolds are then ordered and oriented using a version of the scaffolder that exploits the large size of the superscaffolds to more reliably distinguish 1D and 3D signal by utilizing Hi-C contacts incident only on the superscaffold ends, rather than on the whole superscaffold.

At block 225, the split module 119, extracts raw chromosomal scaffolds from the megascaffold (i.e. concatenation of all chromosomes) output generated by block 215. For genomes that do not exhibit pronounced telomere clustering in the Hi-C map (such as human), the megascaffold is split into chromosomes by running a variant of the misassembly detector to identify the chromosome boundaries. This algorithm relies on the fact that the contact frequency between scaffolds that are adjacent on the megascaffold but which lie on different chromosomes is relatively low, since they are not actually in 1D proximity. Thus, the boundaries between chromosomes generate a signal that is similar to a typical misjoin. Moreover, this effect is enhanced by the tendency of loci on the same chromosome to exhibit elevated contact frequency.

If the spatial clustering of telomeres is evident in the contact density data, the phenomenon can be exploited in the effort to partition the genomes into chromosomes. In particular, the first scaffold in the megascaffold must come from the end of a chromosome, and therefore derives from a telomere. Identifying positions in the contact frequency data (such as a Hi-C matrix) that have an enriched number of contacts with the megascaffold edge thus enables the detection of chromosome boundaries.

At block 230, the sealing module 120 detects and corrects false positive that occurred during the misjoin correction. During this step, sequences that were erroneously excised during misjoin correction may be re-introduced. In particular, if the two parts of a corrected scaffold remain adjacent to one another in the raw chromosomal scaffold, it suggests that the original scaffold was correct, since the independent contact patters from both parts are consistent with the original scaffold. in this case, the misjoin that led to the correction is judged to be a false positive and the intervening sequence is restored.

At block 235, the merge module 121 merges assembly errors due to undercollapsed heterozygosity. A frequent error modality found in draft haploid genome assemblies is undercollapsed heterozygosity. This is when there exists a subset of the scaffolds such that each scaffold accurately corresponds to a single locus in the genome, but these loci overlap one another. Consequently, there are individual loci in the genome that are covered multiple times by different scaffolds. This error is typically caused by the presence of multiple haplotypes in the input sample material, which are sufficiently different from one another that the contig and scaffold generation algorithms do not recognize them as emerging from a single locus. This class of error is frequent in AaegL2; the step can be omitted when assembling genomes of organisms with low heterozygosity such as Hs1.

Undercollapsed heterozygosity error leads to highly fragmented draft assemblies with a larger-than-expected total size (30, 31). This, in turn, causes numerous problems in downstream analyses such as erroneous gene copy number estimates, fragmented gene models etc. The challenge remains significant even when special effort is taken to reduce the levels of heterozygosity in genomic data by inbreeding as has been done with the draft AaegL2 assembly (18). It is therefore important to ensure that the final genome reported by our assembler minimizes the number of assembly errors due to undercollapsed heterozygosity.

To specifically address this class of misassembly error, the goal of merging module 121 is to merge these overlapping scaffolds into a single scaffold accurately incorporating the sequence from the individual scaffolds. The result of this is a merged haploid reference scaffold.

One assumption of the merging module 121 is that, when multiple scaffolds correspond to multiple haplotypes, these scaffolds will exhibit extremely similar contact patterns, genome-wide. (Note that although some interesting examples of homolog-specific folding have been documented (5, 32), the relative input from the differential signal is very small as compared to that coming from the 'diagonal', i.e. from 3D interaction associated with proximity in 1D, so the assumption seems to hold true for the vast majority of candidate loci.) Because they exhibit similar long-range contact patterns, the scaffolding module 117 tends to assign such scaffolds to nearby positions in the genome. Thus, the merge module 121 seeks to identify pairs of resolved scaffolds that (i) lie near one another in the raw chromosomal scaffolds, and (ii) exhibit long stretches of extremely high sequence identity.

Figure 42:
FIG. 42—Shows the location of the overlap relative to input scaffold boundaries is taken into account in determining whether the scaffolds can be correctly merged FIG. 43—Shows dotplots showing alignment of Hs2-HiC chromosome-length scaffolds vs hg38 chromosome-length scaffolds. The hg38 reference (NCBI accession number GCA_000001405.23) is shown on the X axis. The Y axis shows the 23 largest scaffolds of the Hs2-HiC assembly; they have been ordered and oriented to match the chromosomes as defined in hg38 in order to facilitate comparison. (For the same reason, all gaps are removed in both assemblies.) Each dot represents the position of an individual resolved scaffold aligned to hg38. The color of the dots reflects the orientation of individual alignments with respect to hg38 (red indicates a match, whereas blue indicates disagreement). The track on top illustrates the scaffold N50 of the draft DISCOVAR de novo assembly Hs1 as a function of position (calculated in windows of 1 Mb for individual chromosomes and 10 Mb for the whole-genome graph). Alignment was performed using BWA (34). The dotplots illustrate excellent correspondence between hg38 and Hs2-HiC, with the exception of a few low-complexity regions of the human genome.
Figure 43:
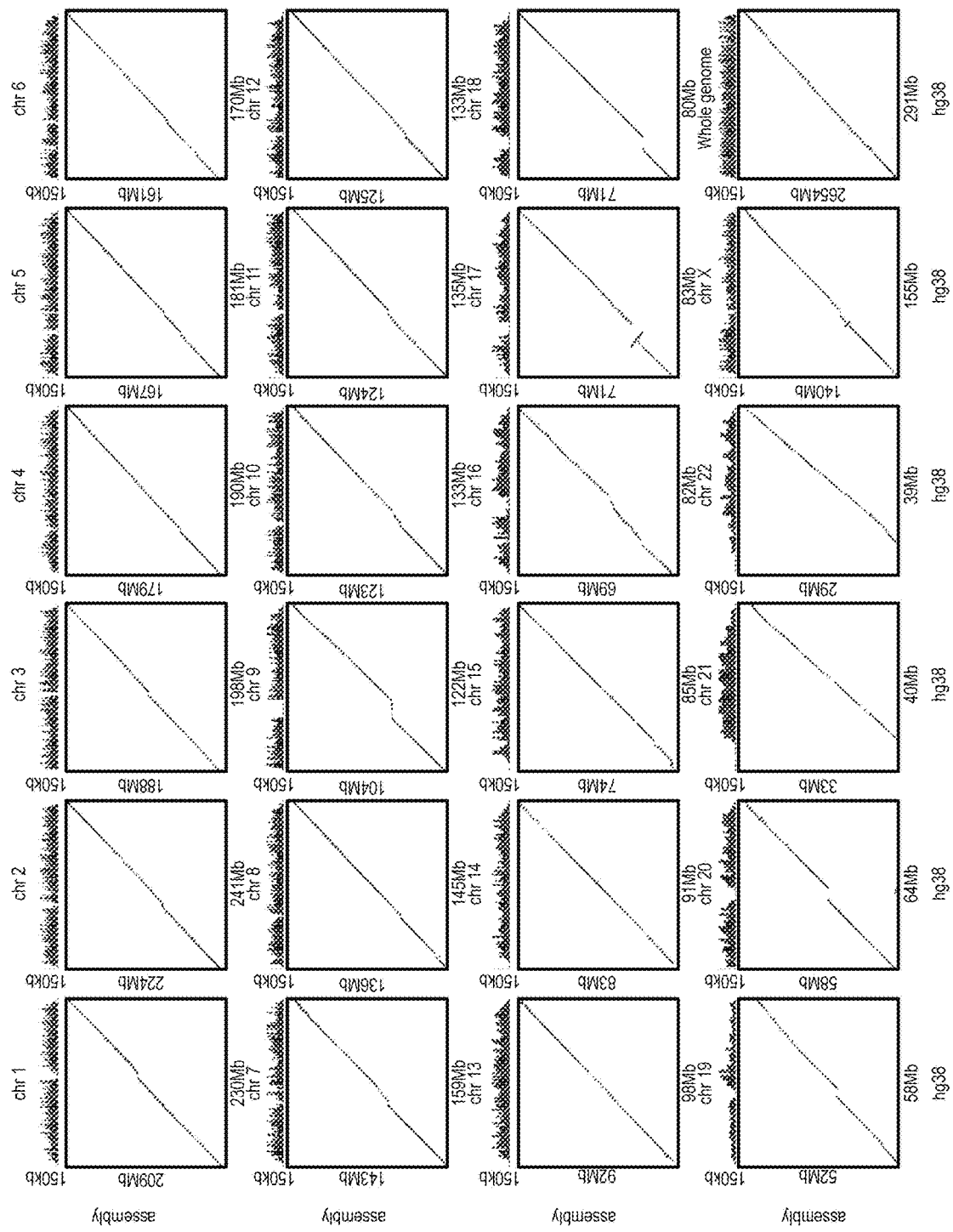
Figure 44:
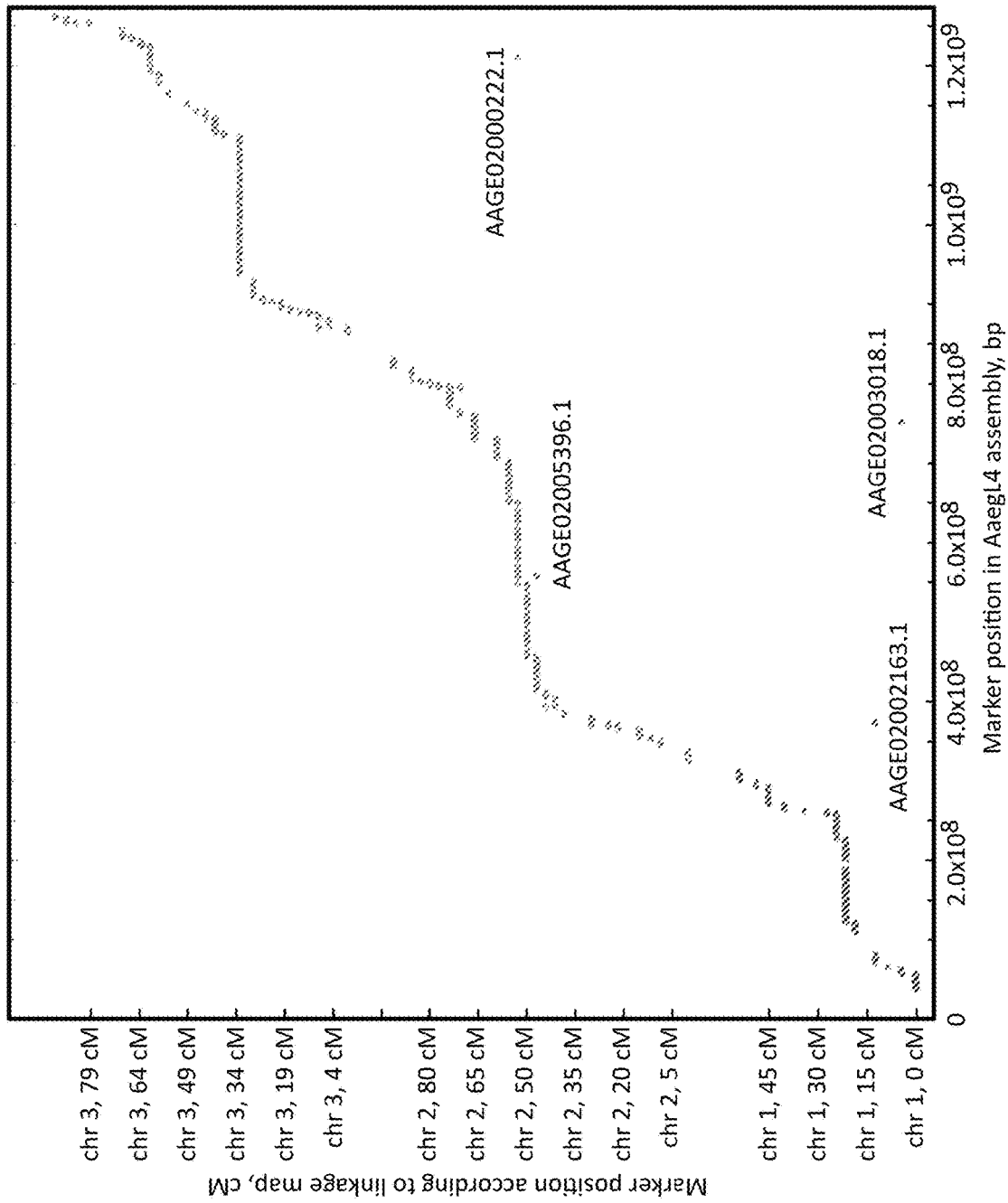
FIG. 44—Shows the correlation between the position of a scaffold on a genetic linkage map in centimorgans (cM) and its position in the AaegL4 assembly. Out of 1826 markers, only four are inconsistent. These inconsistencies are due to errors in the draft assembly (AaegL2) that were not flagged by our approach FIG. 45—Shows misassembly detection using Hi-C: comparison with evidence from linkage mapping. Shown are contact maps for the first four AaegL2 scaffolds that were identified as misassembled in a genetic linkage mapping study (19). The boundaries of consistent fragments as identified via automatic misassembly detector are overlaid over the contact maps (green squares). The upper track shows the location of breakpoints as well as the position of the resulting scaffold fragments (indicated using color) along the *Ae. aegypti* chromosomes according to the linkage map (19). White bars indicate a lack of markers on the fragment, making more precise identification of breakage position on the basis of the genetic map impossible. The lower track illustrates the location of breakpoints as well as the position of the resulting scaffold fragments (indicated using color) according to current study. The overall coloring scheme used is shown; however, note that the individual color gradients along each scaffold fragment were enhanced in order to heighten the contrast between nearby positions on the same chromosome. All 63 scaffolds that were identified as misassembled in (19) through linkage mapping were independently flagged as misassembled based on their Hi-C signal.
Figure 45:
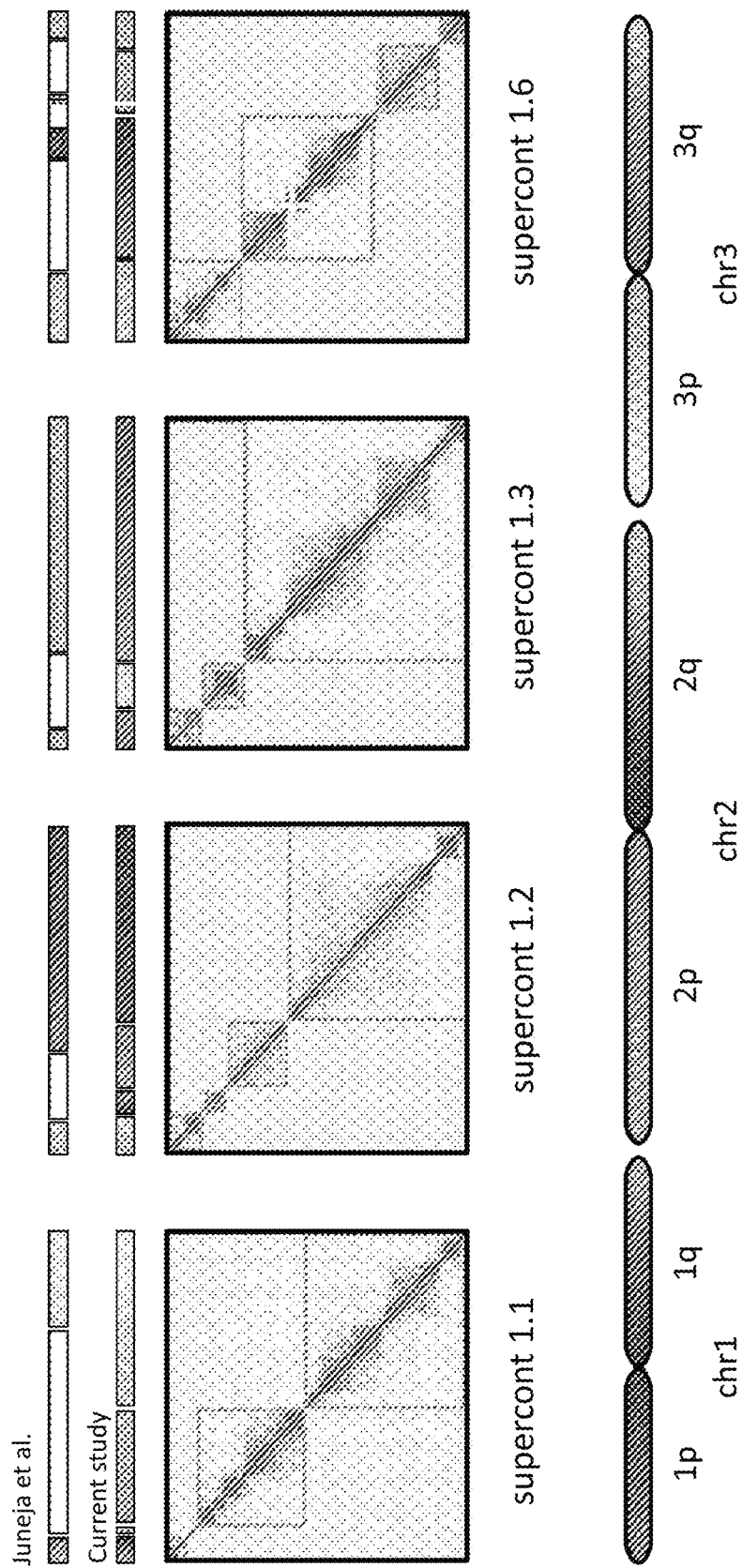
Figure 46:
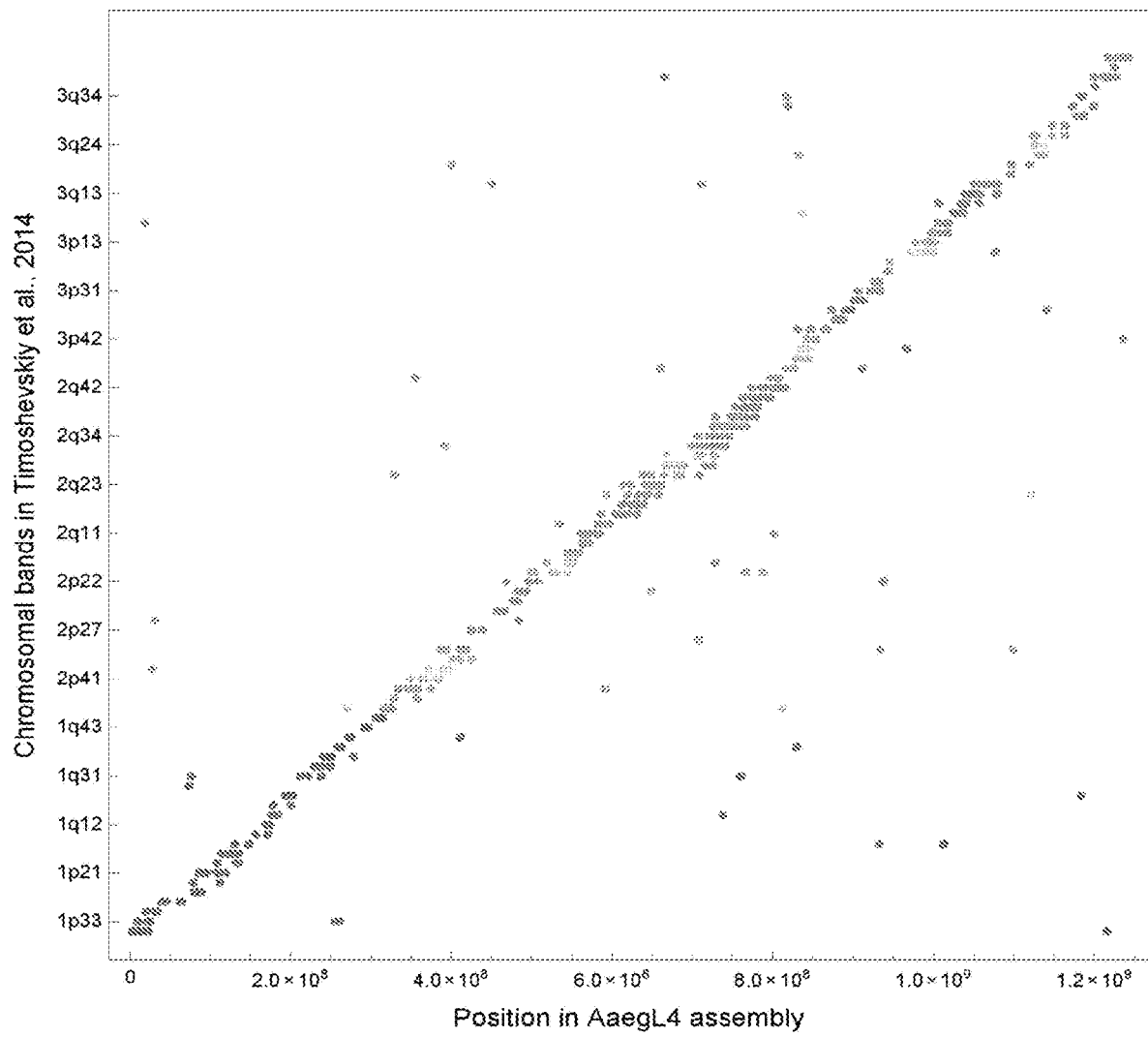
FIG. 46—Shows the correlation between chromosomal band assignment by physical mapping (36) and position in the AaegL4 genome.
Figure 47:
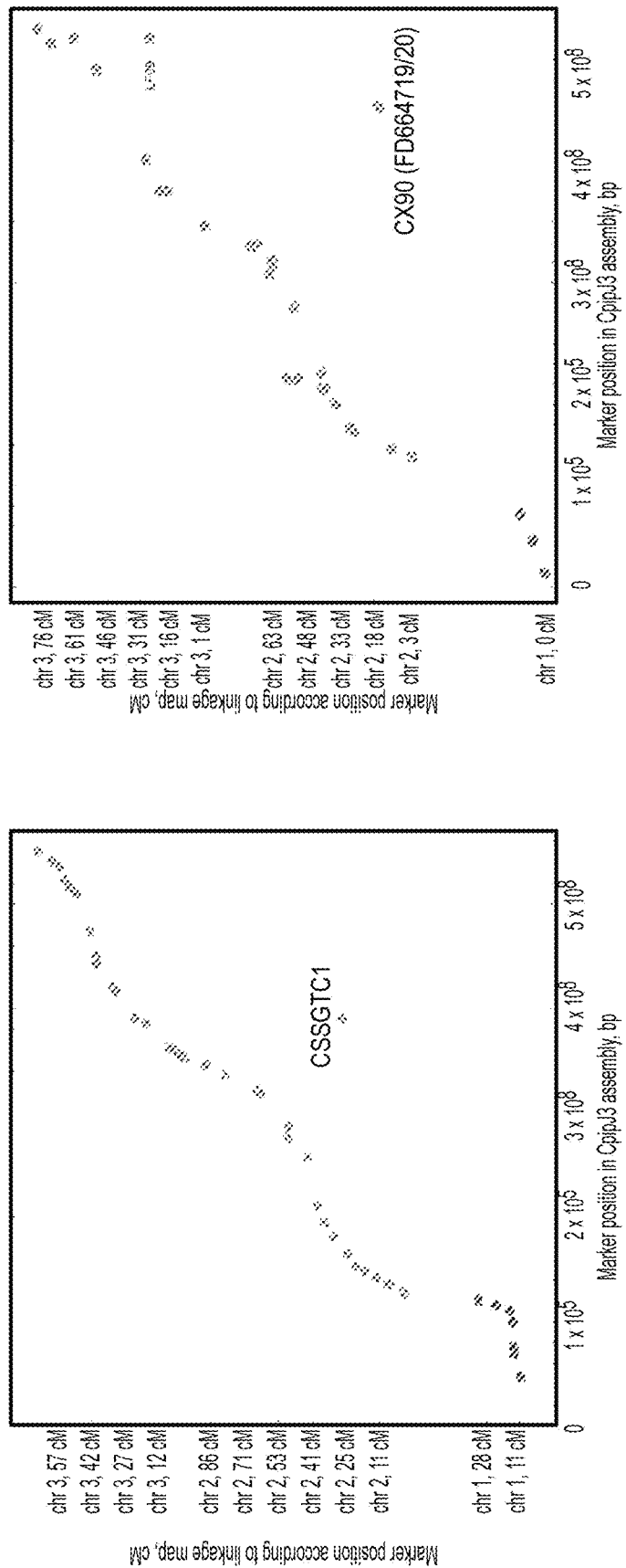
FIG. 47—Shows the correlation between the position of a marker on a genetic linkage map in centimorgans (cM) and its position in the CpipJ3 assembly. (A) Map of microsatellite loci (21); (B) Map of restriction fragment length polymorphism (RFLP) markers (20).
Figure 48:
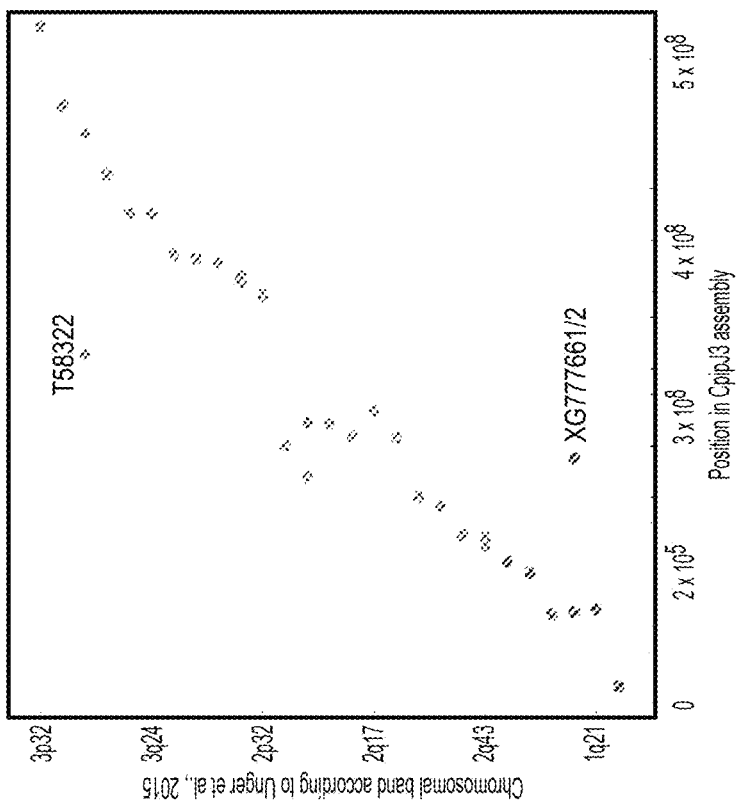
FIG. 48—Shows correlation between chromosomal band assignment by physical mapping and position in CpipJ3 genome. (A) Physical mapping of polytene *Cx. quinquefasciatus* chromosomes (37); (B) Mitotic chromosome-based physical mapping (38)
Figure 48:
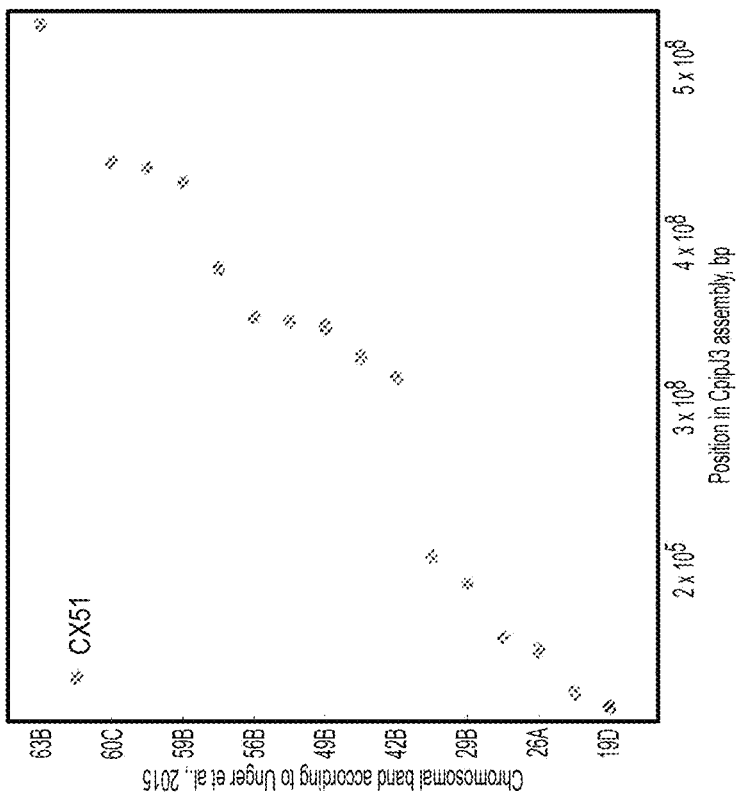

Briefly, undercollapsed loci is searched by running a sliding window of fixed width along the raw chromosomal scaffolds. LASTZ is then used to do pairwise alignment of all pairs of resolved scaffolds that fall in the sliding window (28). The total score of all collinear alignment blocks (stanzas), normalized by the length of the overlap, is used as a primary filtering criterion to distinguish between alternative haplotypes and false positive sequence similarity. The location of the overlap relative to input scaffold boundaries is also taken into account in determining whether the scaffolds can be correctly merged (see FIG. 42).

Next a graph is constructed whose nodes are resolved scaffolds, and where edges reflect significant sequence overlap between resolved scaffolds that are proximate on the raw chromosomal scaffold. The resulting graph contains a series of connected components. Cycles in the graph are analyzed in order to filter out components with overlaps on conflicting strands.

Finally, a tiling path is constructed through the scaffolds of each individual connected component, recursively aligning scaffolds to an already collapsed portion of the group, finding the highest scoring alignment block and switching from one haploid sequence to the other at the endpoints of the alignment.

Ideally the resolved scaffolds in each connected component are consecutive on the raw chromosomal scaffold, and with relative orientations that match those suggested by the pairwise alignments. In practice, however, this is not always the case. This can be due to differences in haplotype representation between the genomic data used to produce the draft assembly and that of the Hi-C experiment. For example, sequences belonging to different clusters may be intertwined. Similarly, the orientation of contigs/scaffolds within the cluster as suggested by pairwise alignment may not match those suggested by the scaffolding step. In such cases the relative position and orientation of the connected components with respect to the rest of the assembly is decided by majority vote with each input scaffold's contribution weighed by its length. Alternatively, assembly can be rerun using the merged components as input.

Note that although it is possible to add additional constraints when appropriate, such as the exact number of haplotypes present in the data, we do not rely on such knowledge in general, or in any of the assemblies we performed in this paper. This allows us to work with polymorphic assemblies, such as when multiple individuals were used to produce the draft assembly. In particular it allows us to handle cases where the degree of polymorphism is unknown.

At block 240, the visualization module 122 takes the assembly and generates a graphical user interface that allows a user to visualize the assembly and manipulate the heatmap to correct for any remaining errors that may have been introduced. Further, this step may be used in place of multiple iterations such as those described at block 215. The visualization module 122 (also referred to herein as "Assembly Tools" and GUI elements thereof are described in further detail in the Examples section below. While block 240 may provide an interactive GUI to enable user interaction and modification of the assembly, the module may also be further adapted with machine vision algorithms that further automate all or certain aspects of this step.

At block 245, the merge module 121 outputs the final genome assembly. In certain example embodiments, the genome assembly may be output as a fasta file.
Additional Applications The genome assembly methods described above may also be used for additional applications as discussed in further detail below.

In one embodiment, the sequencing method provides de novo genome assembly by combining reads from a test sample DNA-DNA proximity ligation dataset, such as a Hi-C dataset described herein, with reads from a reference sample DNA-DNA proximity ligation dataset. The DNA-DNA proximity ligation reads of the test and reference sample are aligned to generate a combined contact map. The test and reference samples may be from a same species or from two closely related species (e.g. zebra and horse). Chromosomal breakpoints and fusions between the first and second sample are determined from the contact map. For example, breakpoints manifest as strong off-diagonal bocks and fusions manifest as depleted off-diagonal blocks. The test sample reads are then realigned according to the identified breakpoints and fusions. This alignment may contain one or more nucleotide variants. Thus, SNP or variant calling methods known in the art may be used to complete the genome assembly. For example, if multiple reads from the test sample aligning to the realigned contact map differ in sequence from the reference sample at one or more specific loci, then the nucleotide sequence from the test sample will be incorporated into the final genome assembly of the test sample. In addition, allowing for de novo gene assemblies, the method may also be used to identify karyotypic differences between two samples. For example, the method may be used to determine karyotypic differences between a clinical sample and a reference sample, where the reference sample may represent the chromosomal arrangement of a healthy or diseased tissue depending on the intended use.

Figure 11:
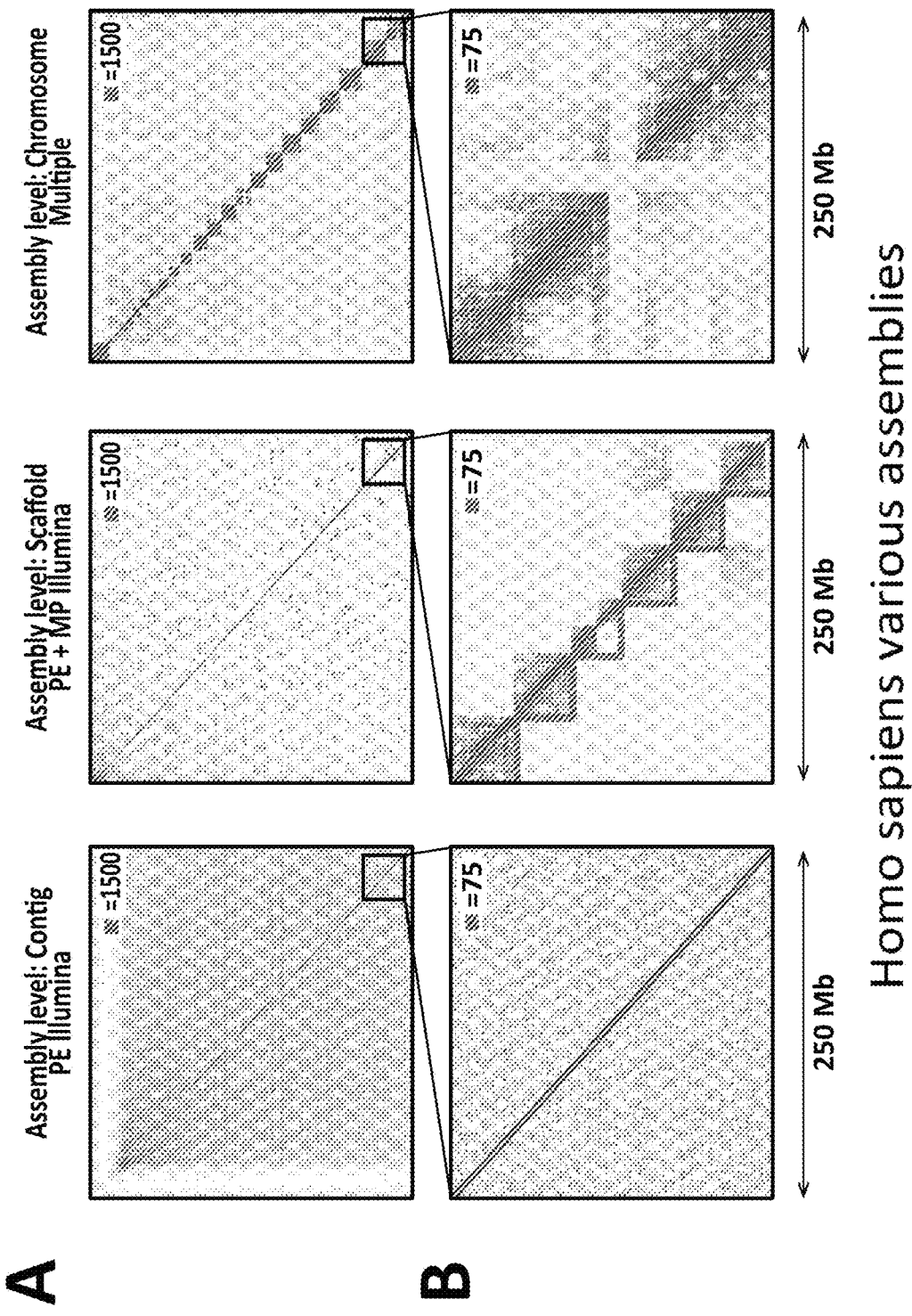
FIG. 11—Shows a set of 3D contact maps demonstrating the ability to assess the quality of genome assemblies at the contig, scaffold, and chromosome level. Both contiguity and accuracy (the rate of contigs and scaffold misjoins as well as misassignment to chromosomes) are well-reflected by the 3D contact pattern.
Figure 12:
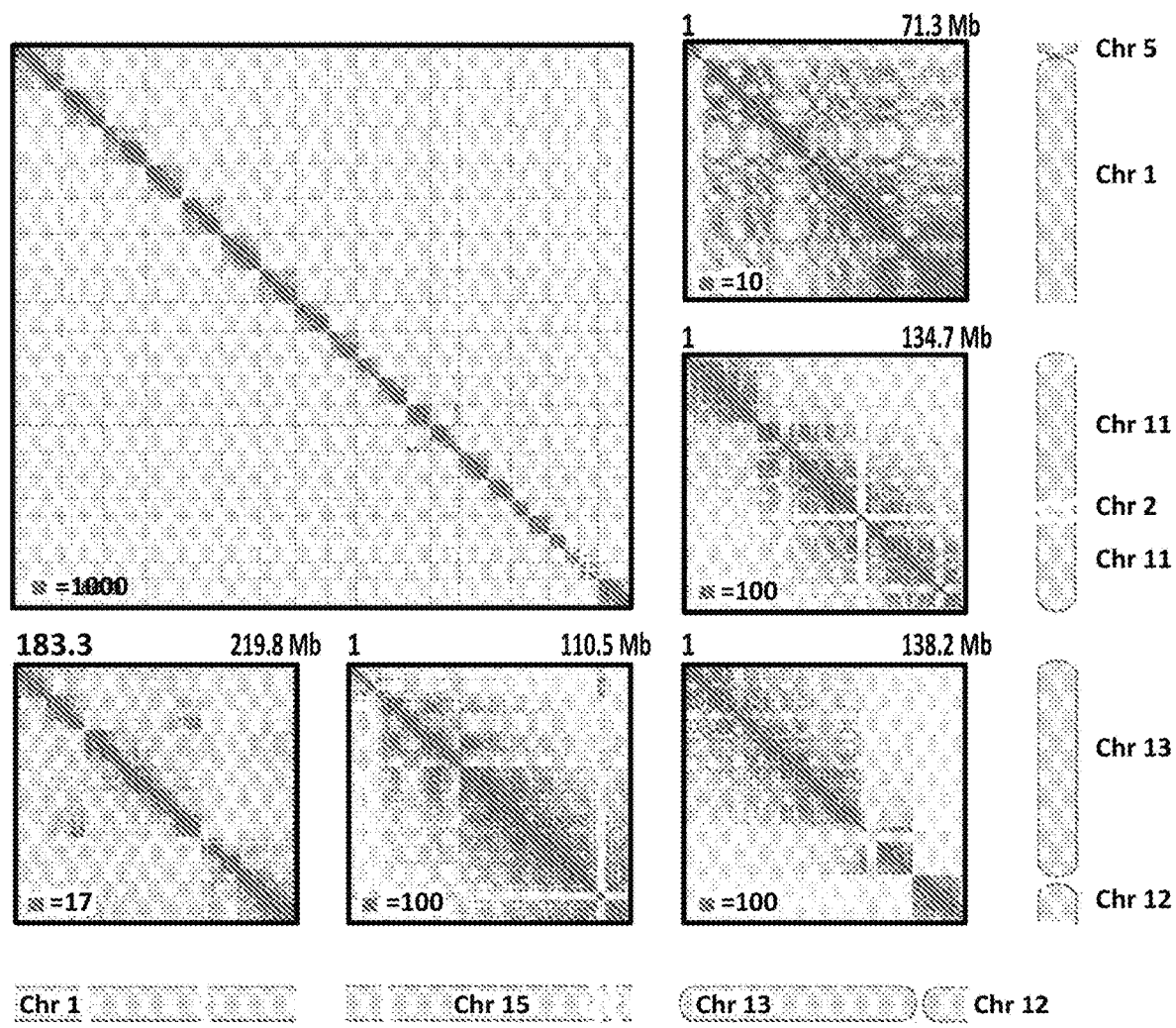
FIG. 12—Shows a set of 3D contact maps demonstrating the ability to use such maps to identify errors in chromosome-scale assemblies.
Figure 13:
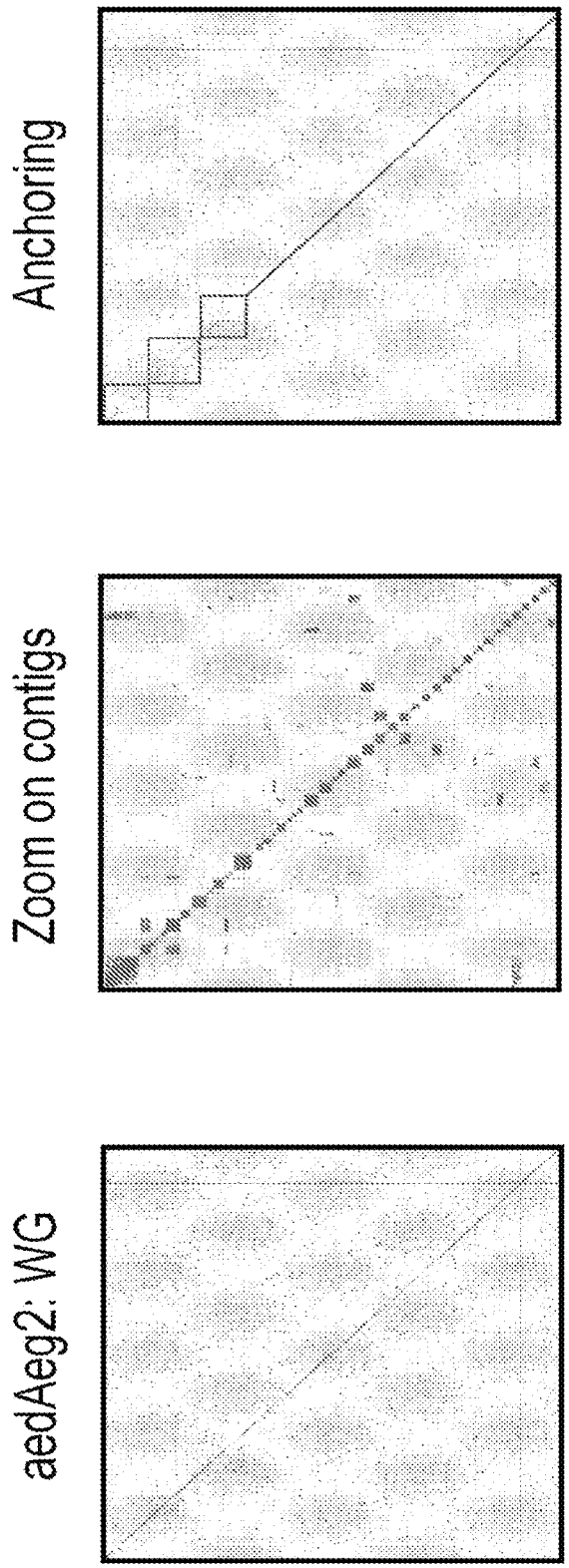
FIG. 13—Shows a set of 3D contact maps demonstrating the ability to identify errors in draft assemblies.
Figure 14:
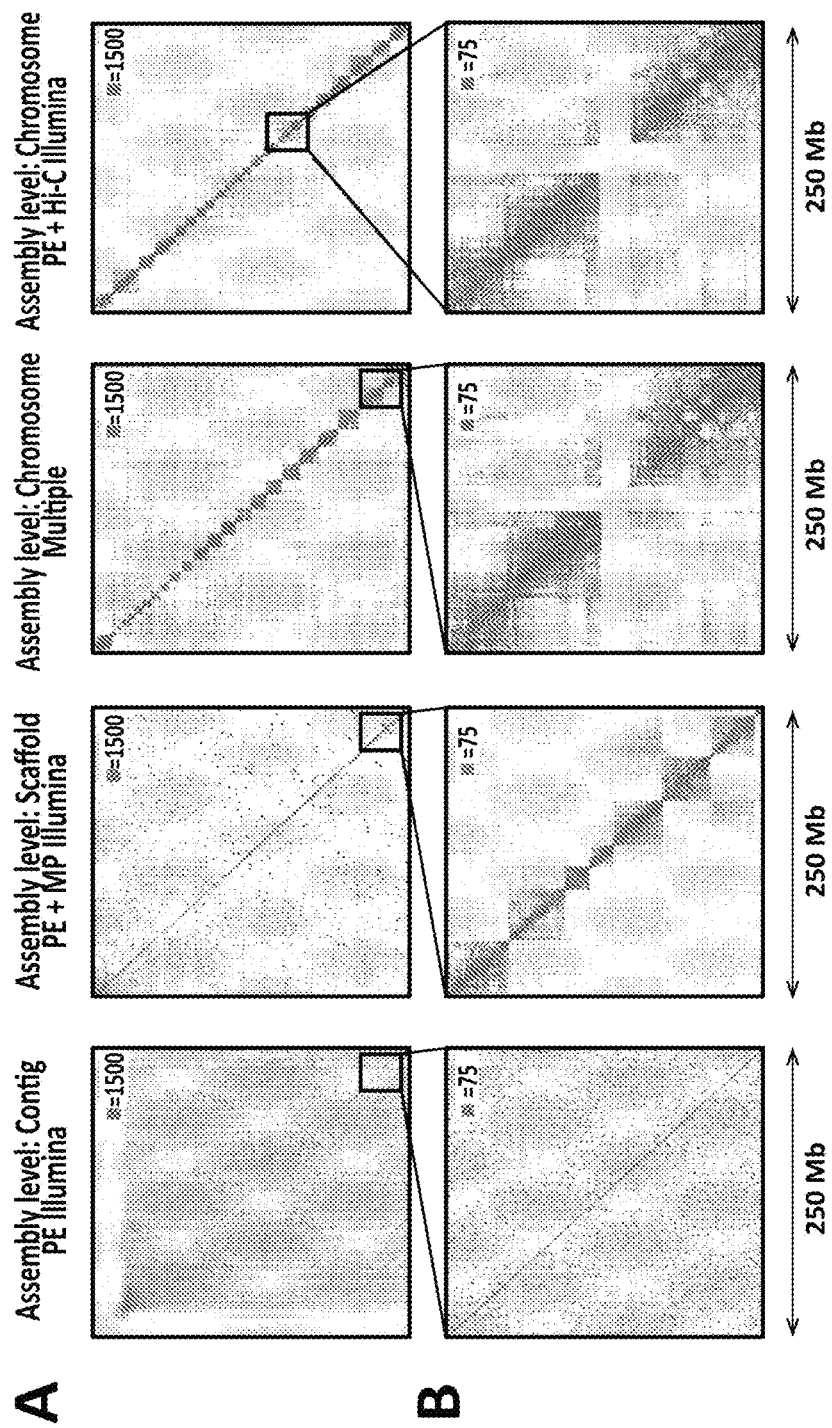
FIG. 14—Shows a set of 3D contact maps demonstrating the ability to use such maps for end-to-end assembly of large genomes from short sequencing reads.
Figure 15:
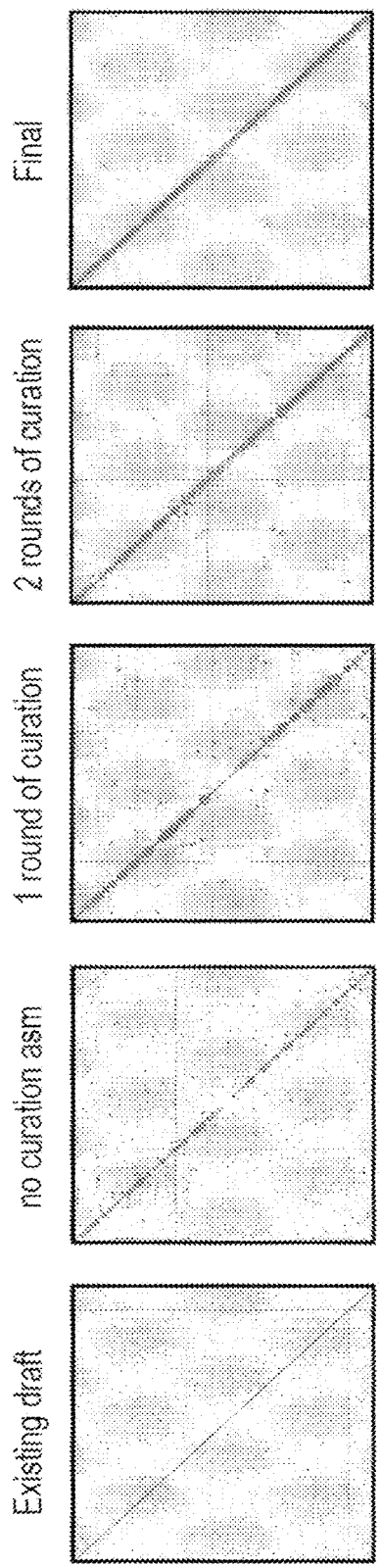
FIG. 15—Shows a set of 3D contact maps and use of such maps in editing and reassembling draft genomes.

The methods disclosed herein may be used to not only assemble genomes but to assess the quality of genome assemblies at the contig, scaffold and chromosome levels for both contiguity and accuracy, i.e. the rate of contigs and scaffold misjoins as well as misassignment to chromosomes) are well-reflected in the 3D contact pattern. See FIGS. 11-13.

The methods herein may be used to generate high-quality end-to-end (whole chromosomes) assembly of large genomes, including de novo assembly from short-read data as well as the ability to edit and reassemble published assemblies. See FIGS. 10 and 11, 12, and 15.

Figure 16:
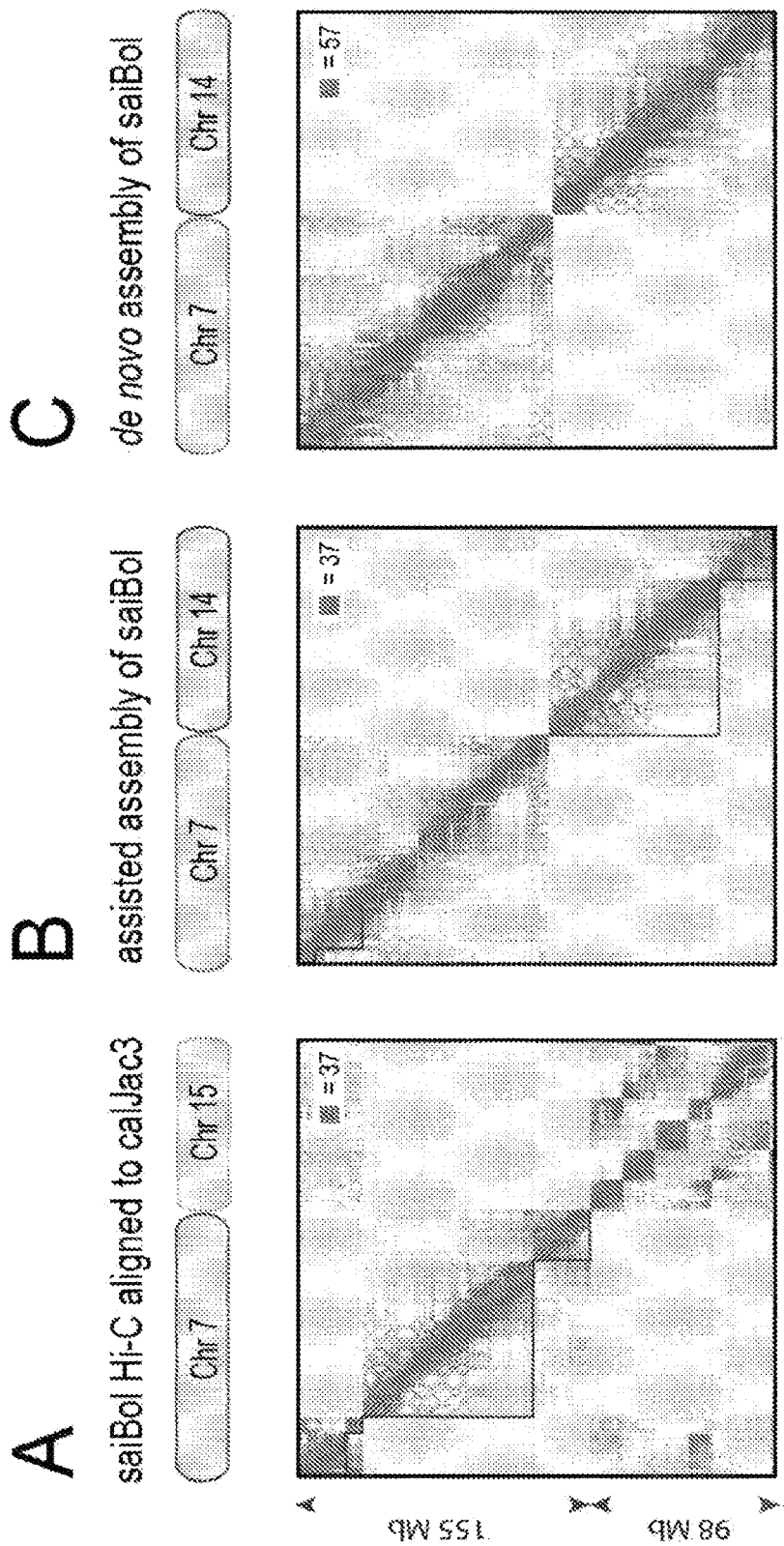
FIG. 16—Shows a set of 3D contact maps showing assisted assembly of the squirrel monkey genome from the common marmoset genome and comparison to a de novo assembly of the same species.
Figure 17:
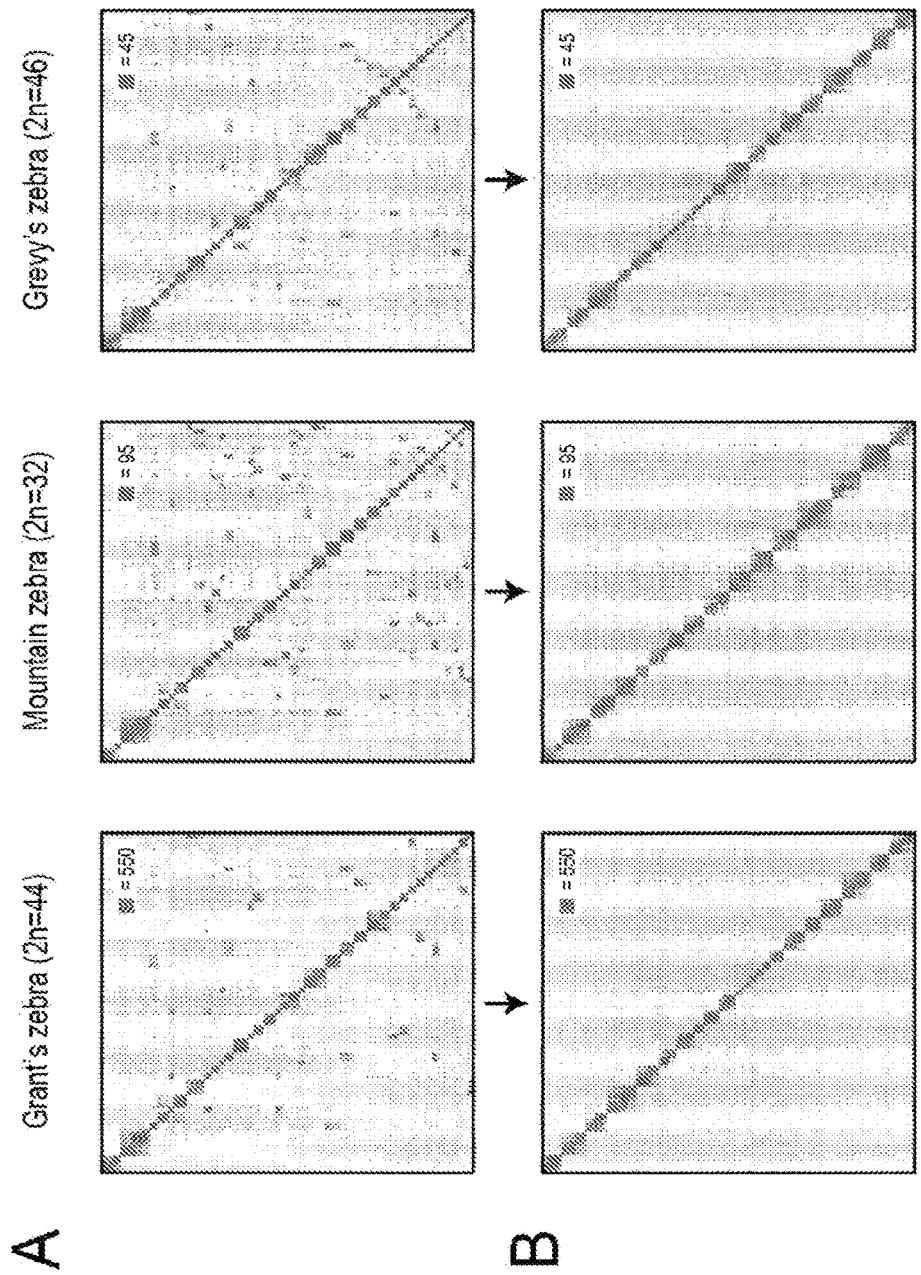
FIG. 17—Shows a set of 3D contacts maps showing reference-assisted assembly of 3 zebra genomes from a horse genome.

The methods disclosed herein may also be used to create reference-assisted assembly using a genome assembly of a closely related organism or a group of organisms. This is done by identifying synteny blocks between the species and reassembling them into a new genome using the proximity ligation data. See Example 2 and FIGS. 16 and 17.

Figure 18:
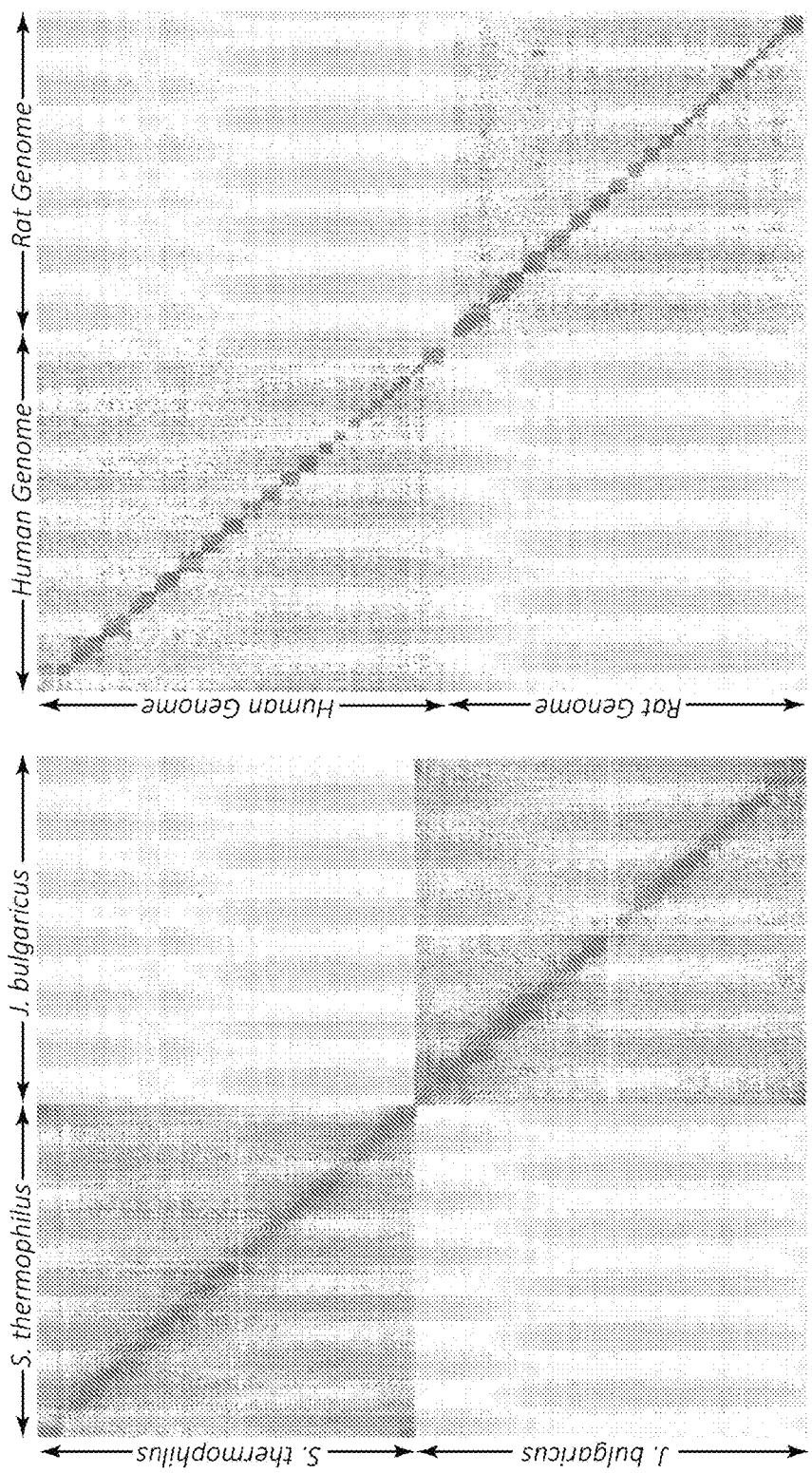
FIG. 18—Shows a set of meta 3D contact map of a 2-component prokaryotic and eukaryotic communities determined at the same time.
Figure 19:
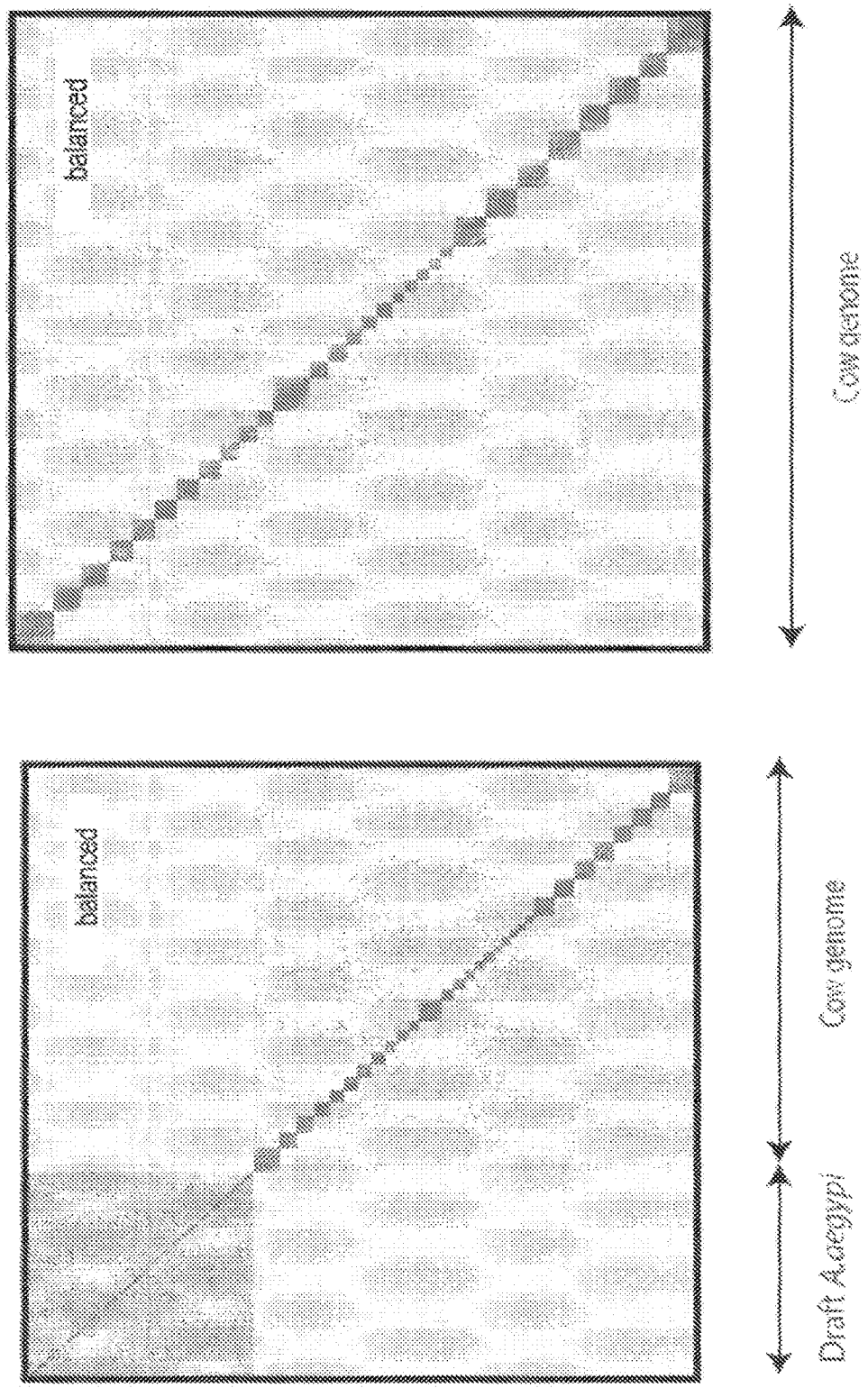
FIG. 19—Shows a meta 3D contact map of mosquito and cow genomes derived from a mosquito fed cow blood prior to sequencing and a cow genome assembly from genomic material isolated from cow milk.

The methods disclosed herein may also be used to assemble/identify genomes in a metagenomic context. The applications include, but are not limited to, sequencing prokaryotic, eukaryotic and mixed communities from the same samples. For example, the methods may be used, among other metagenomic applications, to sequence the metagenome with the host genome, disease vectors and pathogens, and disease vectors and host etc. See FIGS. 18 and 19.

Figure 20:
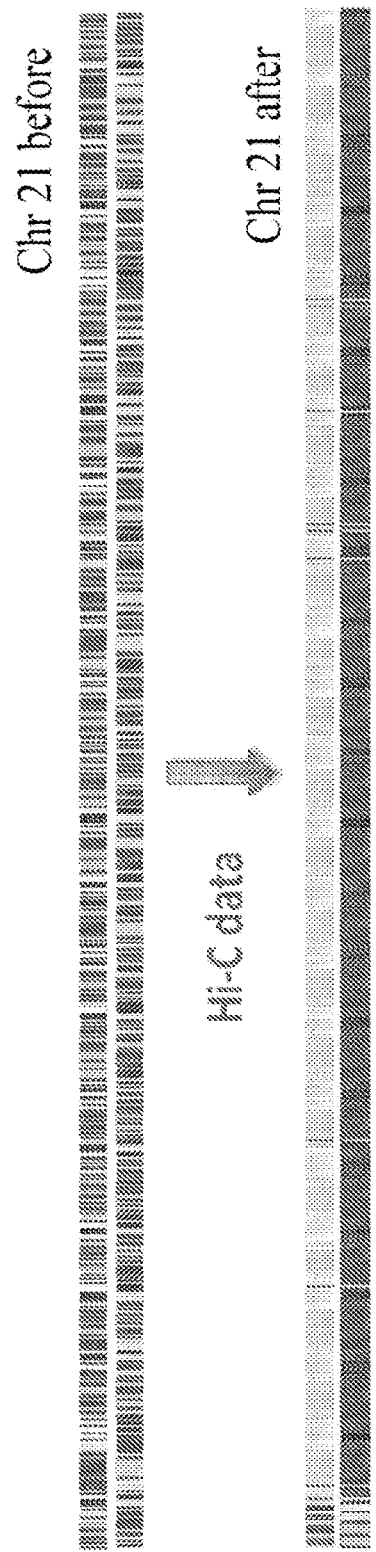
FIG. 20—Shows a 3D contact map to de novo phase human chromosome 21.
Figure 21:
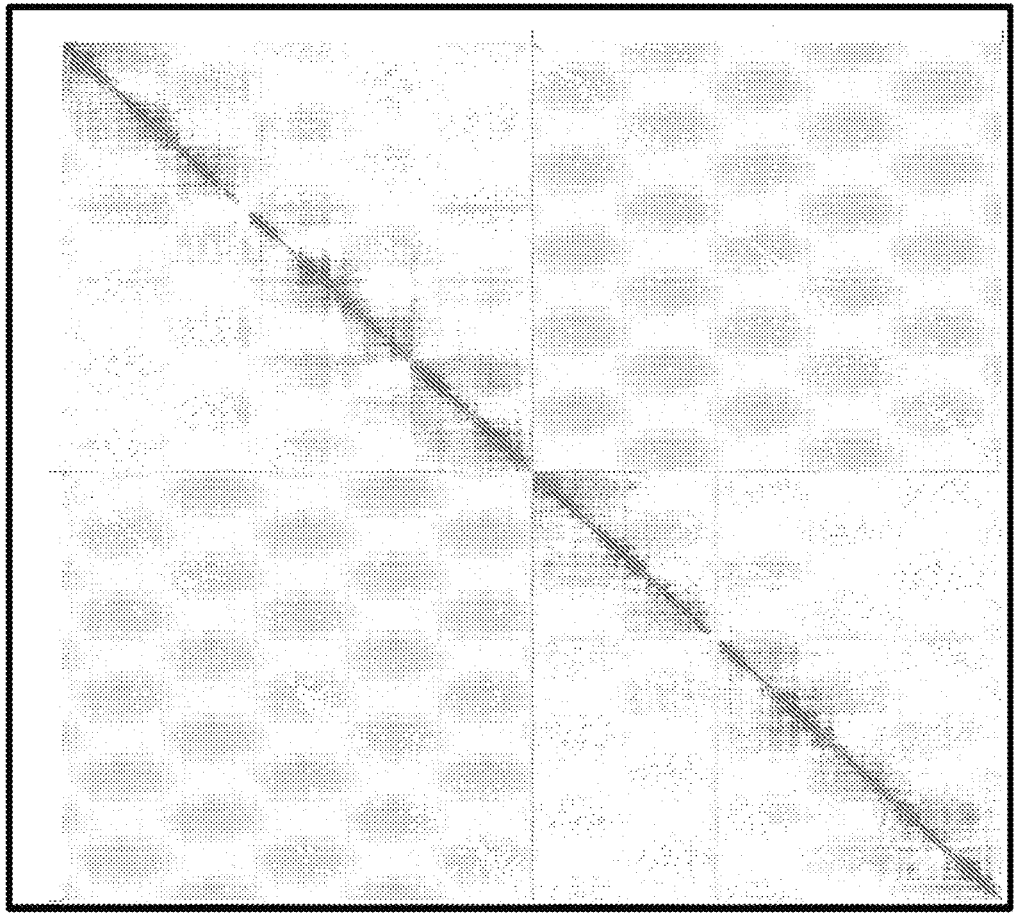
FIG. 21—Shows a 3D contact map and use in phasing and quality assessment of the human chromosome X.

The methods disclosed herein may also be used to assist in phasing of the human genome. Phasing can be performed de novo and using population data. The 3D contact maps can be used to assess the accuracy of phasing results. See FIGS. 20 and 21.

Figure 22:
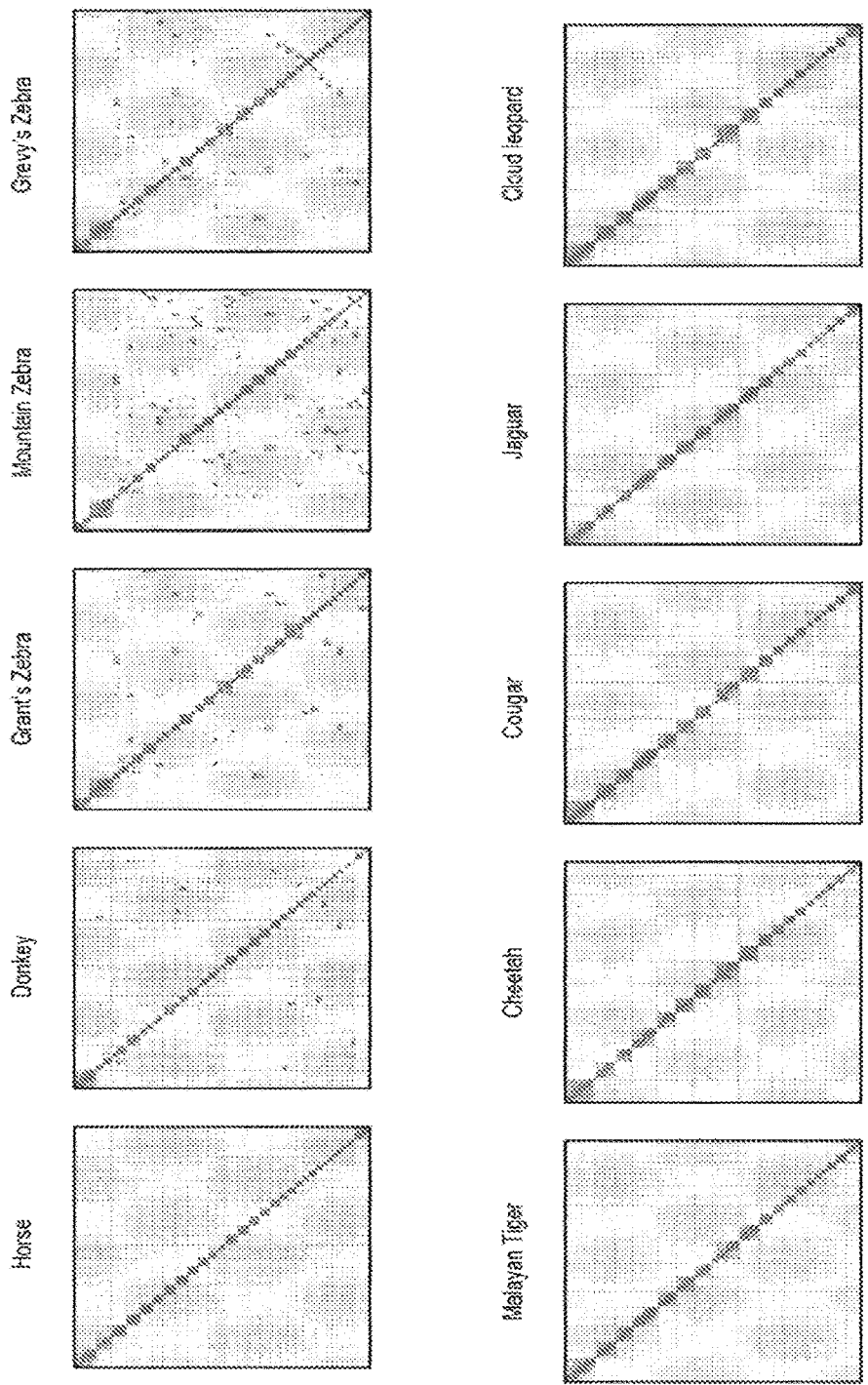
FIG. 22—Shows a set of 3D contact maps and use of such maps for visualizing karyotype evolution.
Figure 23:
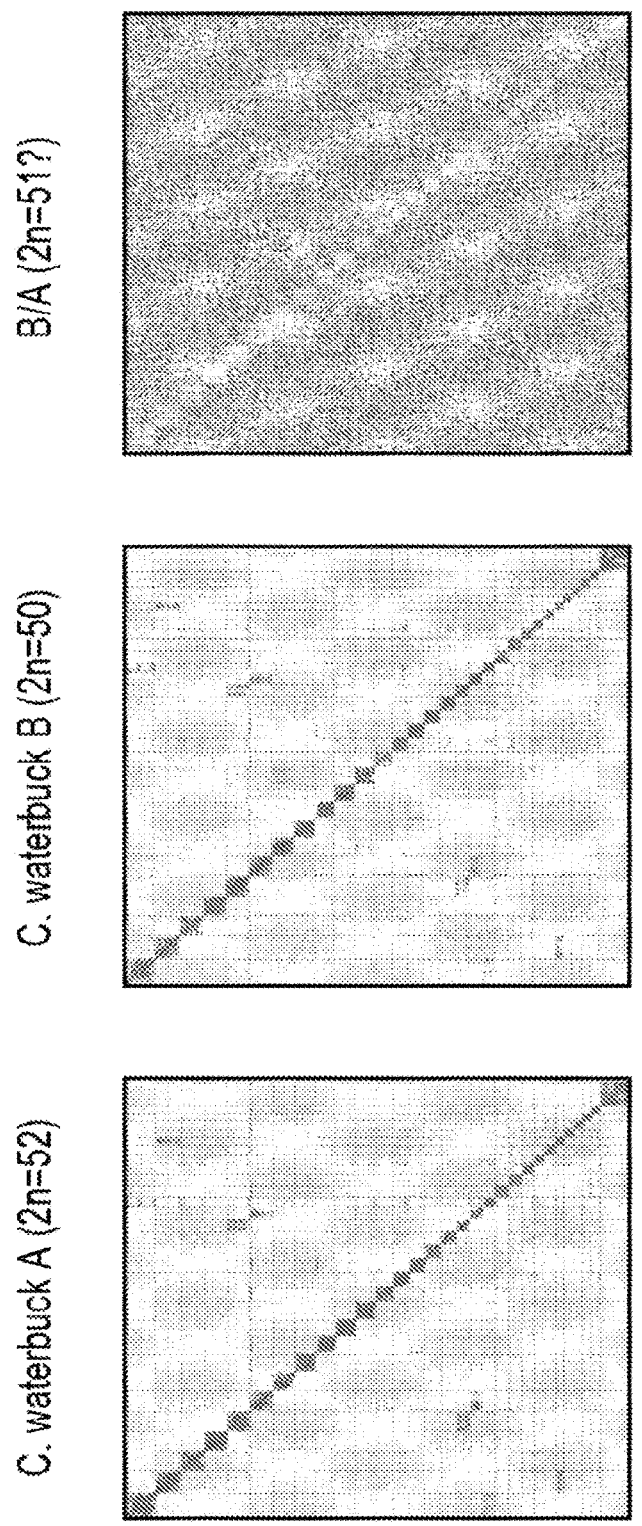
FIG. 23—Shows a set of 3D contact maps and use of such maps for identification of centric fusion polymorphism in a species.
Figure 24:
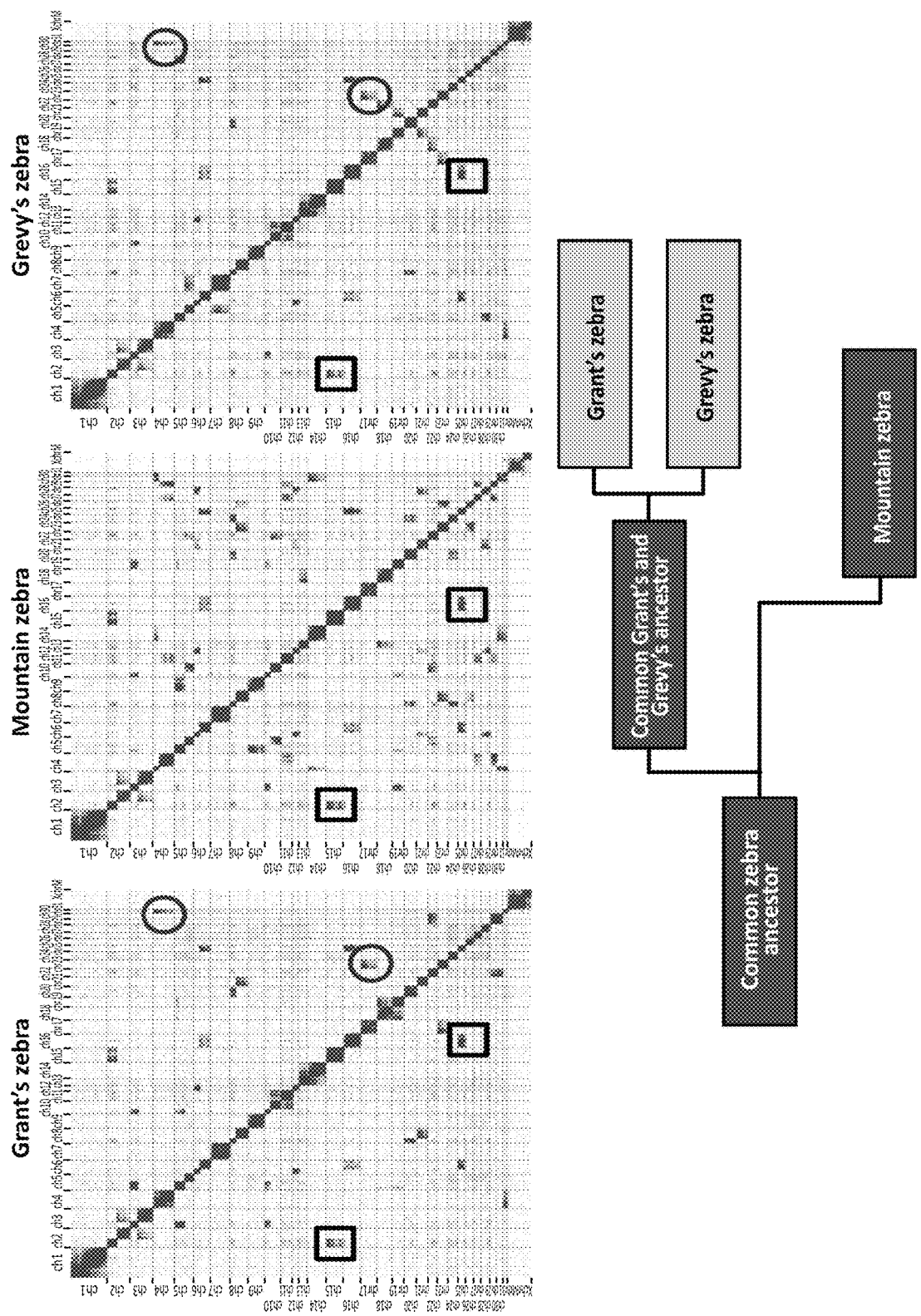
FIG. 24—Shows a set of 3D contact maps and use of such maps to build a phylogenetic tree with karyotype-level 3D contact map data.

The methods disclosed herein may also be used to analyze karyotype evolution in given group of species as well as to detect karyotype polymorphisms, even at low-coverage. The karyotype data can be used to identify phylogenetic relationships, either by itself or with sequence level data. See FIGS. 22-24.

Figure 25:
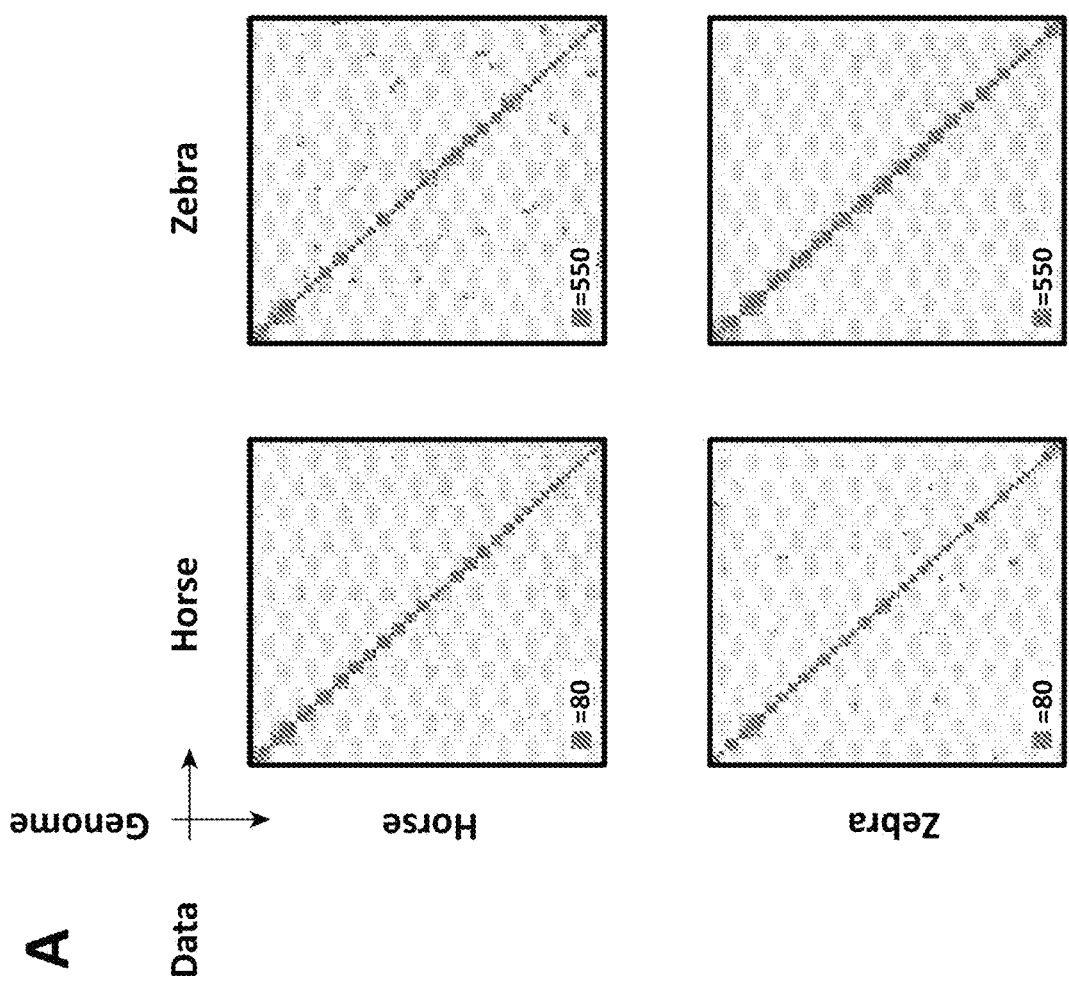
FIG. 25—Shows a set of 3D contact maps and use of such maps to alleviate need for inter-species chromosome painting.

The methods disclosed herein may also be used to substitute for inter-species chromosome painting, including at low coverage. See FIG. 25.

Figure 26:
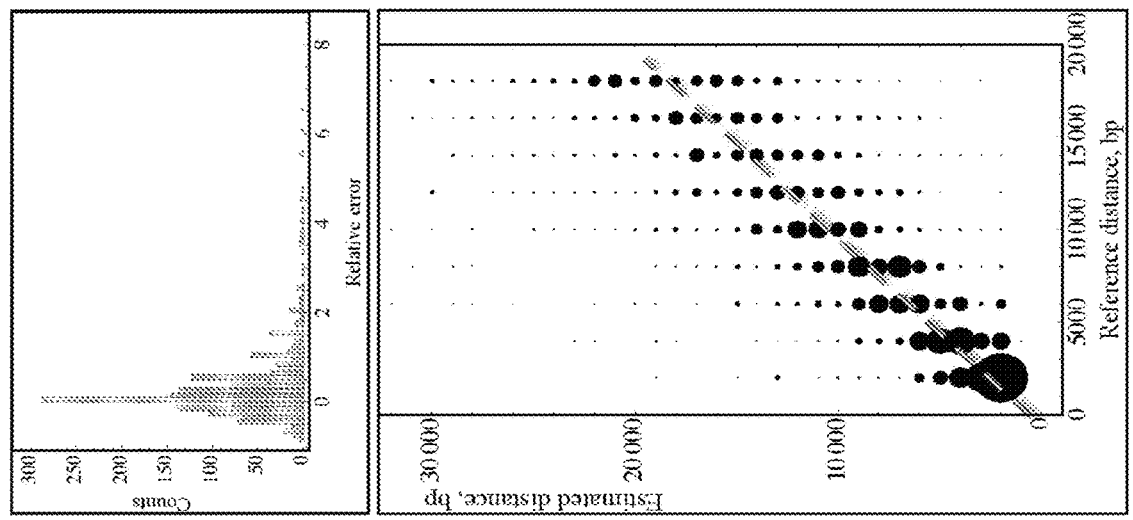
FIG. 26—Shows a set of graphs demonstrating how 3D contact data can be used to estimate gaps between a pair of genomic loci.
Figure 26:
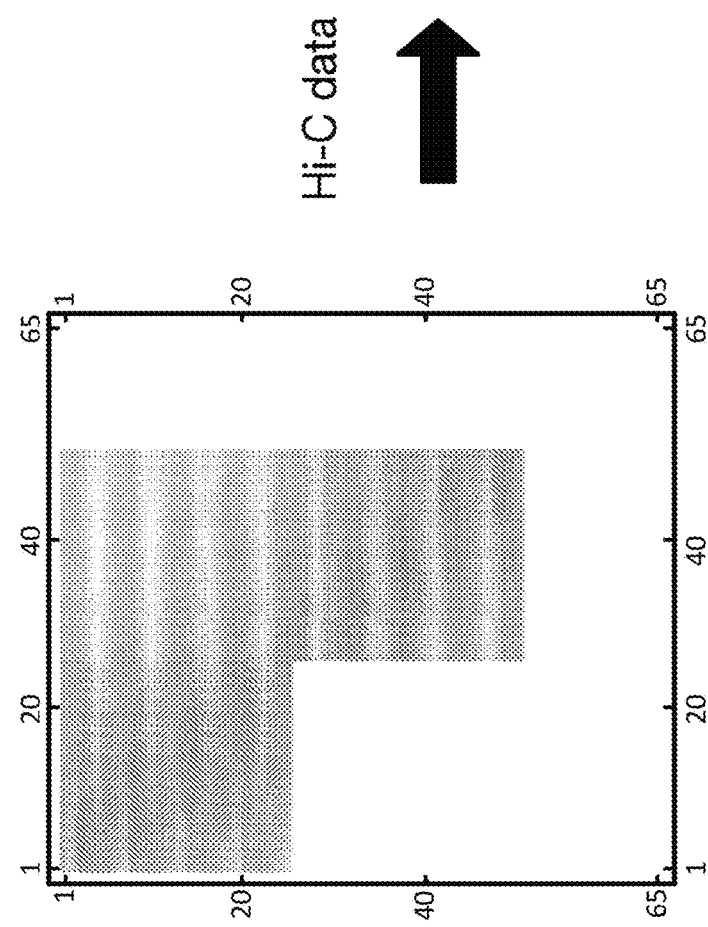

The methods disclosed herein may also be used to estimate the distance along the 1D sequence between any two given genomic sequences. See FIG. 26.

The methods disclosed herein may use the features of 3D contact maps. For example, identification of chromatin motifs in their proper convergent orientation can be use to properly orient other contigs in the assembly. See FIG. 27.

The invention is further described in the following examples, which do not limit the scope of the invention described in the claims.

EXAMPLES

Example 1

Interactive Genome Assembly and Re-Assembly Using Hi-C Data

Hi-C contact maps are valuable for genome assembly (Lieberman-Aiden, van Berkum et al. 2009; Burton et al. 2013; Dudchenko et al. 2017). Recently, we developed Juicebox (Durand, Robinson et al. 2016), a system for the visual exploration of Hi-C data, and 3D-DNA, an automated pipeline for using Hi-C data to assemble genomes (Dudchenko et al. 2017). Here, we introduce "Assembly Tools," a new module for Juicebox, which provides a point-and-click interface for using Hi-C heatmaps to identify and correct errors in a genome assembly. Together, 3D-DNA and the Juicebox Assembly Tools greatly reduce the cost of accurately assembling complex eukaryotic genomes. To illustrate, we generated de novo assemblies with chromosome-length scaffolds for three mammals: the wombat, *Vombatus ursinus* (3.3 Gb), the Virginia opossum, *Didelphis virginiana* (3.3 Gb), and the raccoon, *Procyon lotor* 2.5 Gb). The only inputs for each assembly were Illumina reads from DNA-Seq (300 million 150 bp paired-end reads) and in situ Hi-C (100 million), which cost <$1000.

Hi-C contact maps are valuable for genome assembly (Lieberman-Aiden, van Berkum et al. 2009; Burton et al. 2013; Dudchenko et al. 2017). Recently, we developed Juicebox (Durand, Robinson et al. 2016), a system for the visual exploration of Hi-C data, and 3D-DNA, an automated pipeline for using Hi-C data to assemble genomes (Dudchenko et al. 2017). Here, Applicant provides a new module ("Assembly Tools") for use with softwar like Juicebox, which provides a point-and-click interface for using Hi-C heatmaps to identify and correct errors in a genome assembly. Together, 3D-DNA and the Assembly Tools greatly reduce the cost of accurately assembling complex eukaryotic genomes. To illustrate, Appliant generated de novo assemblies with chromosome-length scaffolds for three mammals: the wombat, *Vombatus ursinus* (3.3 Gb), the Virginia opossum, *Didelphis virginiana* (3.3 Gb), and the raccoon, *Procyon lotor* 2.5 Gb). The only inputs for each assembly were Illumina reads from DNA-Seq (300 million 150 bp paired-end reads) and in situ Hi-C (100 million), which cost <$1000.

An accurate genome sequence is an essential basis for the study of any organism. To assemble a genome, a large number of DNA sequences derived from the organism of interest are overlapped with one another to create contiguous sequences, known as "contigs". Next, linking information—derived from a wide variety of sources, such as mate-pairs, physical maps, and read-clouds—is used to order and orient these contigs into "scaffolds." Unfortunately, errors can arise throughout the assembly process. Contigs may erroneously concatenate two sequences (a 'misjoin'). Scaffolds can contain errors in contig order (a 'translocation') or orientation (an 'inversion'). Examples of such errors can be found in the best available reference genomes for many species (Robert B. Norgren 2013; Shearer et al. 2014; Tang et al. 2014; Chen et al. 2015; Davey et al. 2016; Utsunomiya et al. 2016; Schneider et al. 2017; Korlach et al. 2017). Thus, there is a need for inexpensive methods that can reliably identify and correct a wide variety of assembly errors (Salzberg and Yorke 2005; Phillippy, Schatz, and Pop 2008; Tsai, Otto, and Berriman 2010; Salzberg et al. 2012; Hunt et al. 2013; Gurevich et al. 2013; Bradnam et al. 2013; Worley et al. 2018; Simão et al. 2015; Fierst 2015; Muggli et al. 2015; Yuan et al. 2017; Harewood et al. 2017).

Recently, Hi-C, a method for determining the 3D configuration of chromatin, has emerged as a valuable source of data for genome assembly (Lieberman-Aiden et al. 2009; Burton et al. 2013; Session et al. 2016; Bickhart et al. 2017; Dudchenko et al. 2017; Mascher et al. 2017). In Hi-C, DNA sequences that are near one another in 3D are transformed into chimeras through proximity ligation, and these "contacts" are then cataloged using high-throughput DNA sequencing. Because 3D proximity is closely correlated with proximity along the contour of the chromosome, Hi-C data has been used to create algorithms for scaffolding (Burton et al. 2013; Marie-Nelly et al. 2014; Putnam et al. 2016; Ghurye et al. 2017; Dudchenko et al. 2017), phasing (Selvaraj et al. 2013; Flot, Marie-Nelly, and Koszul 2015), and misjoin detection (Marie-Nelly et al. 2014; Dudchenko et al. 2017). Indeed, we recently showed that algorithmic analysis of Hi-C data using the 3D De Novo Assembly ("3D-DNA") algorithm makes it possible to generate de novo assemblies of mammalian genomes, with chromosome length scaffolds, at low cost (<$10,000) (Dudchenko et al. 2017).

In addition to the use of Hi-C data as an input to assembly algorithms, it can also facilitate the visual identification of errors in a genome assembly. Typically, Hi-C data is represented as a heatmap. This heatmap is generated by partitioning a reference genome assembly into loci of fixed size; each heatmap entry, called a 'pixel', indicates the frequency of contact between a pair of loci. When a chromosome is correctly assembled, sequences that are adjacent in the assembly are also in close physical proximity, leading to the appearance of a bright band of elevated contact frequency along the diagonal of the Hi-C heatmap. Conversely, when there are errors in a reference assembly, they are often visually obvious as anomalous patterns in the heatmap (Rao et al. 2014; Harewood et al. 2017; Dudchenko et al. 2017; Lapp et al. 2017).

These observations suggest that genome assemblies containing errors might be diagnosed and improved using an "interactive" Hi-C-based genome "re-assembly" procedure. In this procedure, a user examines a Hi-C heatmap, identifies an error in the reference assembly, corrects the error, re-generates the Hi-C heatmap, and repeats the process until no more errors can be identified. Indeed, the same procedure could be used to assemble chromosome-length scaffolds from much shorter scaffolds, simply by putting the scaffolds in a random order and orientation, and then removing the resulting ordering and orientation errors interactively. Unfortunately, when there are more than a handful of errors, performing these procedures by hand is impractical.

Recently, Applicant introduced Juicebox, a set of tools that facilitate the visual exploration of Hi-C heatmaps across a wide range of scales. Here, Applicant introduces "Assembly Tools," a new software module that facilitates interactive genome assembly and re-assembly using Hi-C data. Assembly Tools enables users to superimpose the positions of contigs or scaffolds in a reference assembly on top of the Hi-C heatmap, making assembly errors easier to find. When misassemblies are found, users can correct them, using a simple point-and-click interface, in a matter of seconds. Both the heatmap and the reference genome are updated in real-time to reflect these changes enabling a power tool for genome assembly. The Assembly Tools module provides a powerful tool for genome assembly.

In certain example embodiments, a user needs to specify an assembly to be modified. Like the 3D-DNA algorithm, Assembly Tools uses a custom format, .assembly, that can be quickly generated from a .fasta file by an accompanying command-line tool. The user also needs relevant Hi-C data in the .hic format. In practice, this will often entail performing a Hi-C experiment in the organism of interest (Rao, Huntley et al. 2014), generating between 0.01× and 20× coverage, and running Juicer (Durand, Shamim, et al. 2016).

Figure 56:
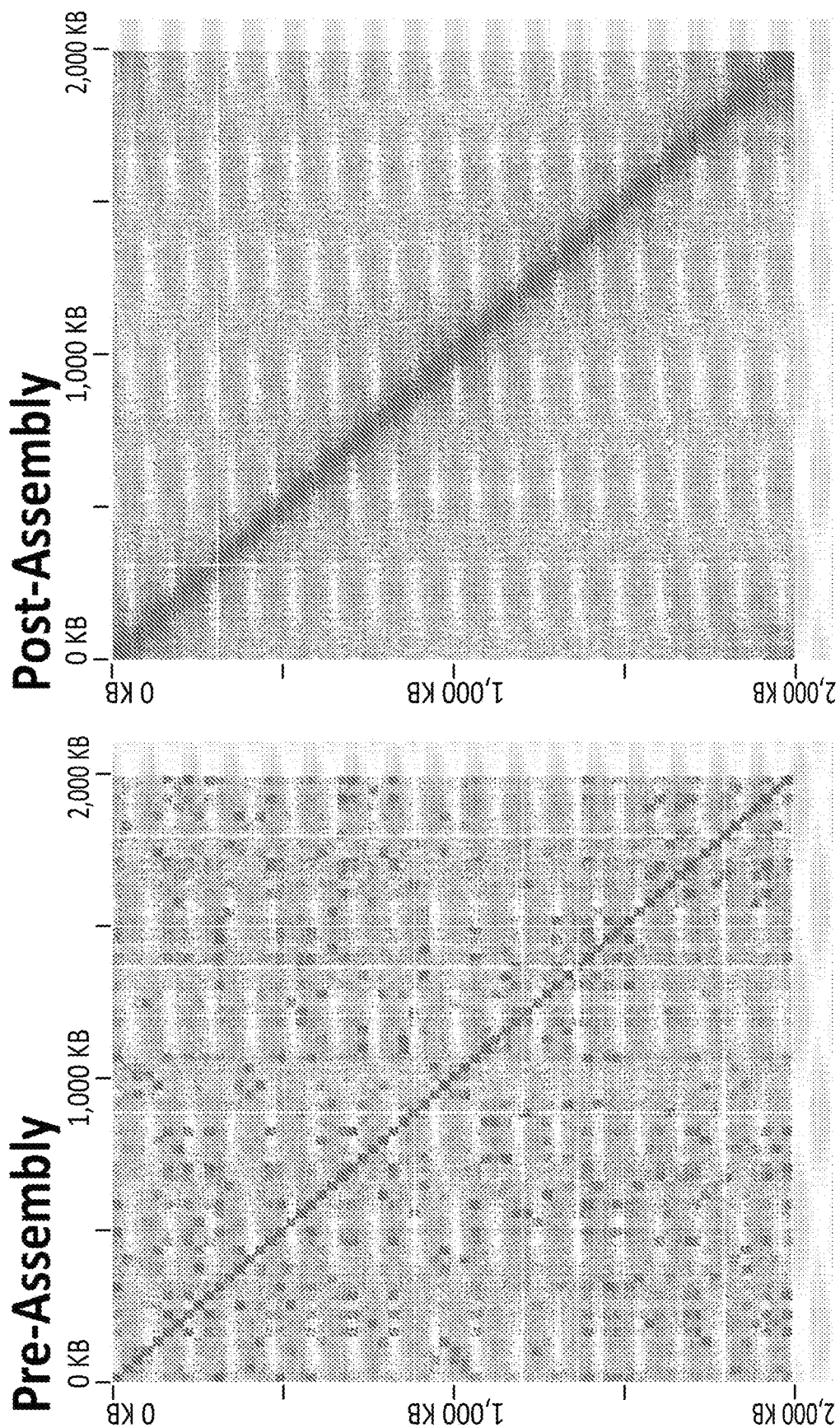
FIG. 56—shows application of Hi-C methods in accordance with example embodiments to assemble the genome of *L. acidophilus* bacterium from 30 kb input contigs.

Once the assembly and Hi-C dataset have been loaded, for example, via a pull-down menu, the user can begin to identify errors. For instance, a misjoin typically manifests as a point along the diagonal of the Hi-C heatmap where the upper-right and lower-left quadrants are extremely depleted, reflecting the lack of physical proximity between the erroneously concatenated loci (Dudchenko et al. 2017). A translocation typically manifests as an extremely bright bowtie motif pointing horizontally or vertically, whose midpoint corresponds to two loci that are proximate in the genome but lie far apart in the assembly (Rao, Huntley et al. 2014; Dudchenko et al. 2017). Similarly, an inversion error—when the sequence of bases in a genomic interval is reversed—often manifests as a bowtie parallel to the diagonal (Rao et al. 2014; Dudchenko et al. 2017; Harewood et al. 2017), (See FIG. 56)

Assembly Tools make it easy to correct such errors using a simple, intuitive interface. First, the user highlights a genomic interval—a single scaffold or a set of consecutive scaffolds—by clicking-and-dragging. Pointing at the corner of the highlighted region causes the mouse pointer to change into a circular arrow, and clicking inverts the selected interval in the reference genome assembly. This allows users to resolve inversion errors. Pointing between two scaffolds outside the selected interval leads to an arrow prompt, and clicking moves the selected interval to the indicated position in the reference genome assembly. This allows users to resolve translocation errors. Finally, misjoins within a selected scaffold can be corrected by moving the mouse along the diagonal—this causes the pointer to change into a scissor icon—and clicking on the position of the misjoin. The scaffold is then split in two in the reference genome assembly, allowing the two resulting scaffolds to be separately manipulated until they are correctly placed. In addition, a third, short scaffold, containing the misjoined sequence itself, is excised and relocated to the end of the reference genome assembly, where anomalous scaffolds are kept for future reference. The boundaries of super-scaffolds, such as chromosomes or chromosome arms, can be indicated by clicking between two scaffolds when no interval is currently selected. (See FIG. 56.)

After each change to the reference genome assembly, the Hi-C heatmap that is being displayed is updated accordingly. Crucially, the Assembly Tools module does not completely recalculate the .hic file storing the Hi-C heatmap at each step (Durand, Robinson, et al. 2016), a process which could take many hours (Durand, Shamim, et al. 2016). Instead, the new heatmap can be thought of as a rearrangement of the pixels in the old heatmap, permuting its rows and columns. The Assembly Tools module tracks this permutation, updating it each time a change is made to the reference genome assembly. As users navigate the Hi-C heatmap, the Assembly Tools module uses a strategy based on binary search and list condensation (Lindstrom 1974; Knuth 1998) to efficiently extract the pixels that are needed to reconstruct the local submatrix of the permuted heatmap for display, using only the original Hi-C heatmap, stored in the original .hic file. Thus, the .hic file need not be recalculated, even when the permutation being applied is very complex.

Figure 57:
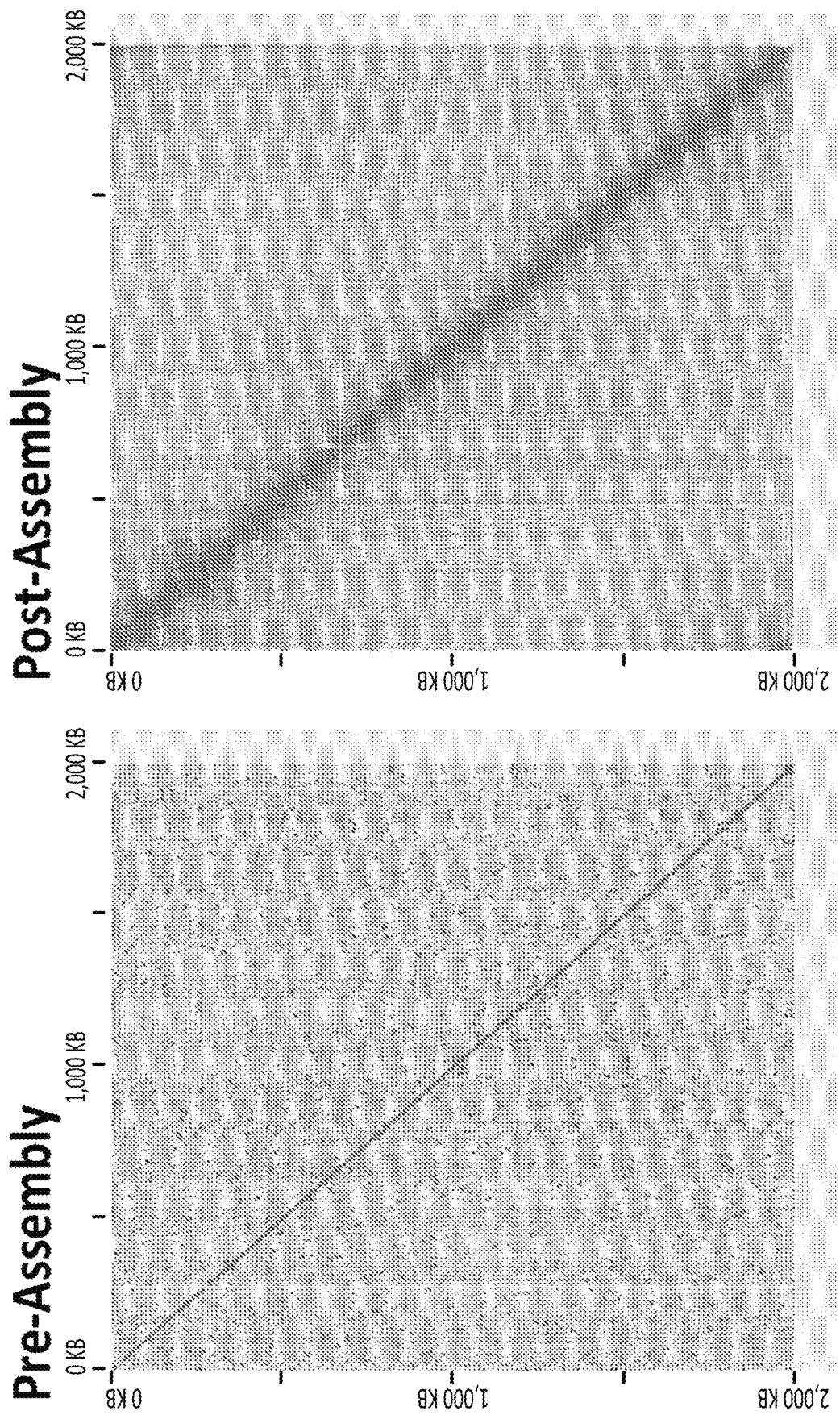
FIG. 57—shows application of Hi-C methods in accordance with example embodiments to assemble the genome of *L. acidophilus* bacterium from 10 kb input contigs.
Figure 58:
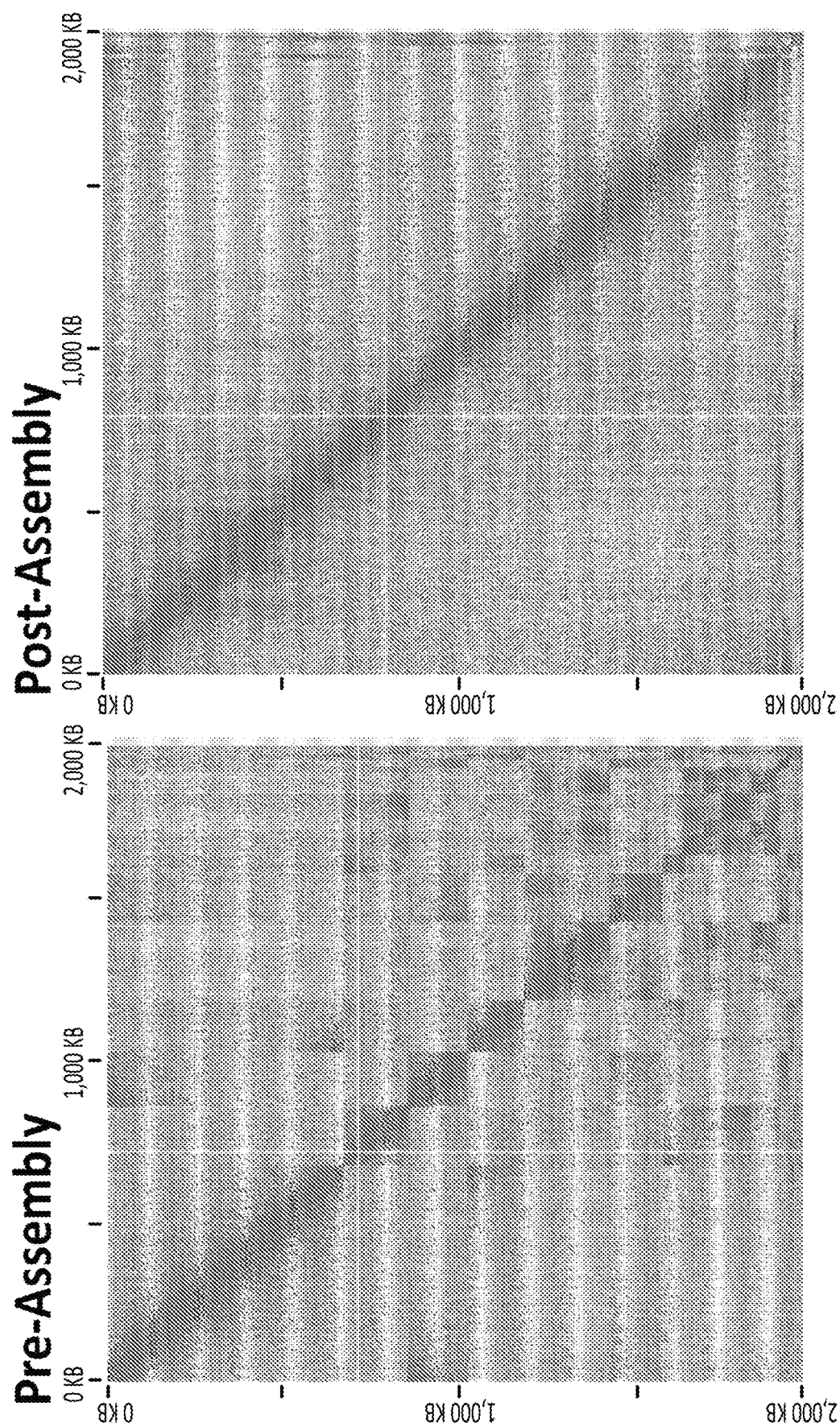
FIG. 58—shows application of Hi-C methods in accordance with example embodiments to assemble the genome of *L. acidophilus* using DNA-seq and Hi-C data as input. The input contigs were produced from DNA-seq using SPAdes genome assembler.
Figure 59:
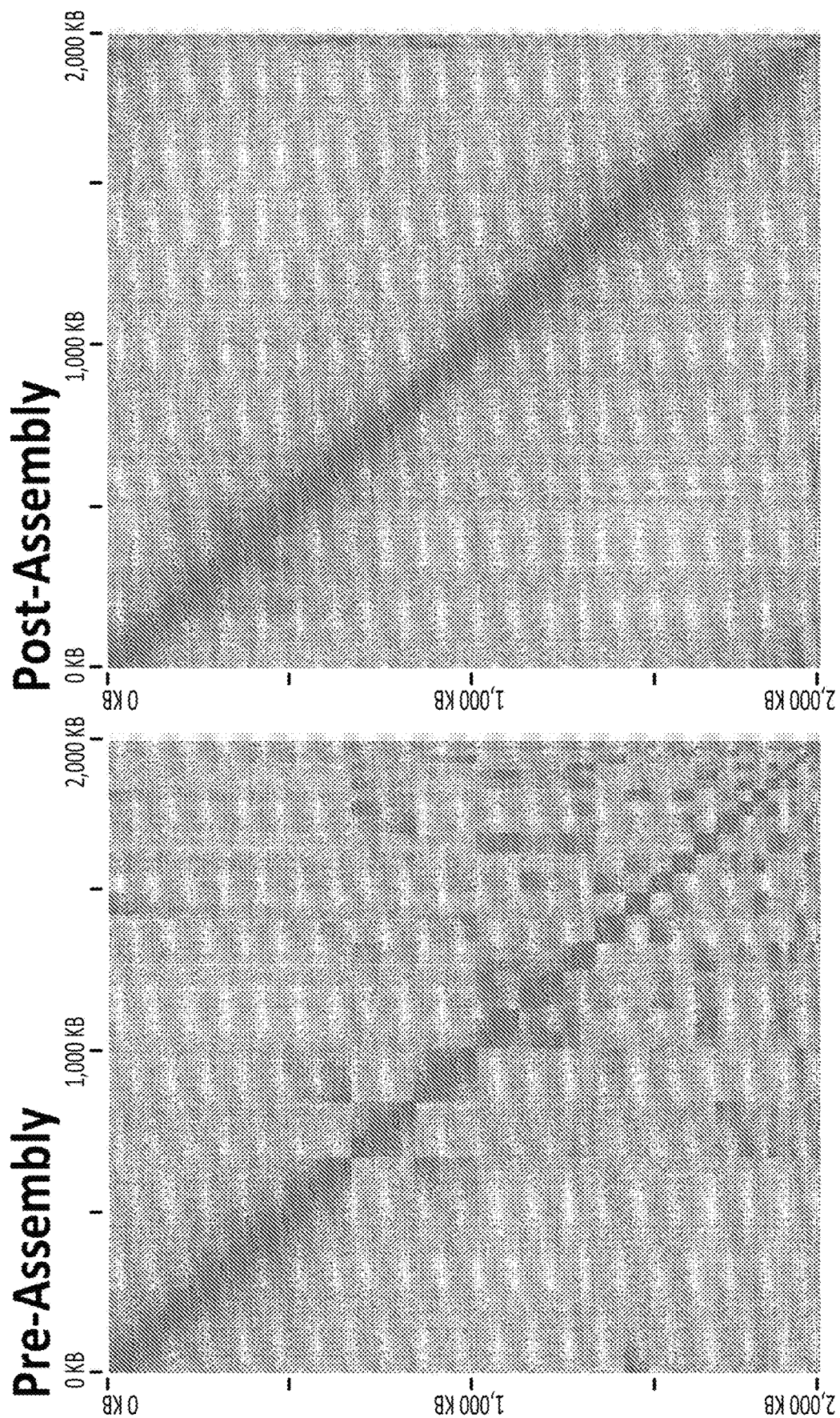
FIG. 59—shows application of Hi-C methods in accordance with example embodiments to assembling the genome of *L. acidophilus* assuming only Hi-C data as input. The input contigs were produced from Hi-C reads using SPAdes genome assembler.
Figure 60:
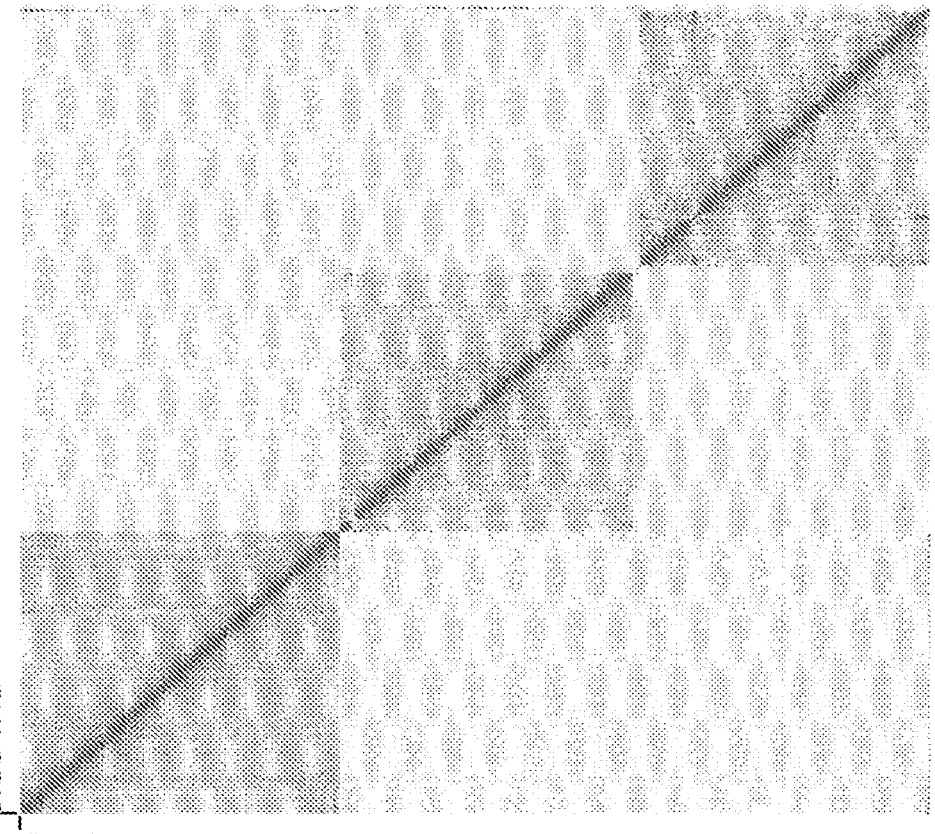
FIG. 60—shows application of Hi-C methods in accordance with certain example embodiments to assembling the genome of *L. acidophilus*, *L. delbueckii* (subspecies *blugaricus*) and *S. thermophiles* simultaneously.
Figure 60:
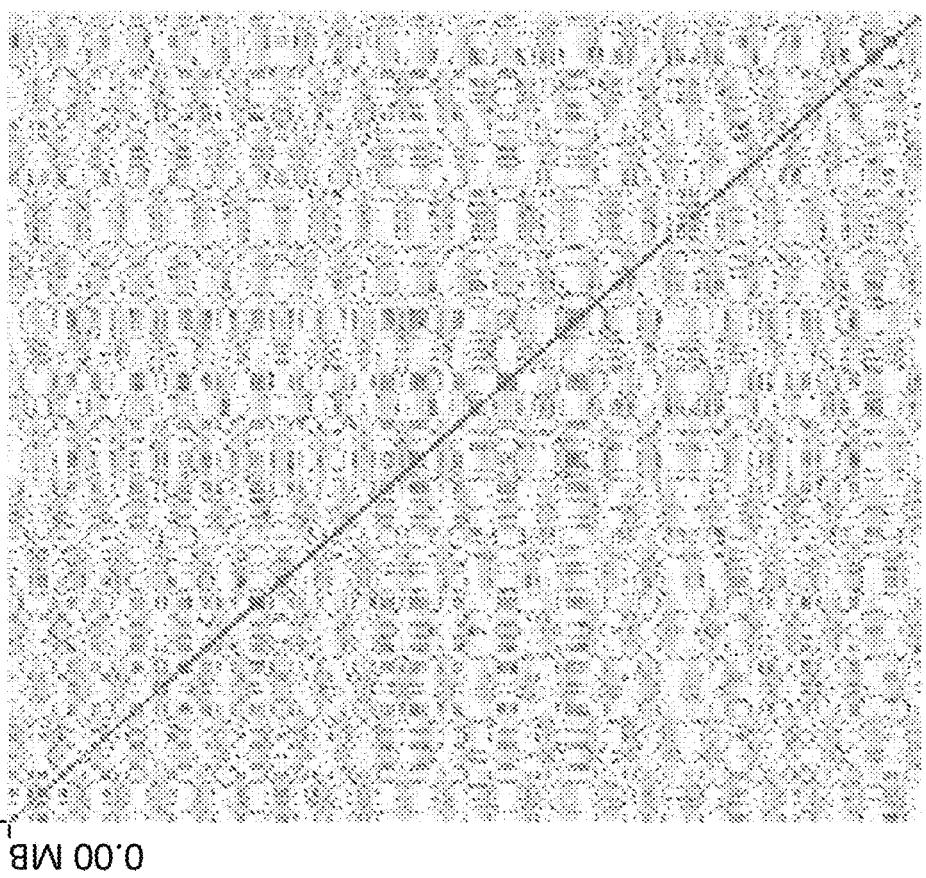
Figure 61:
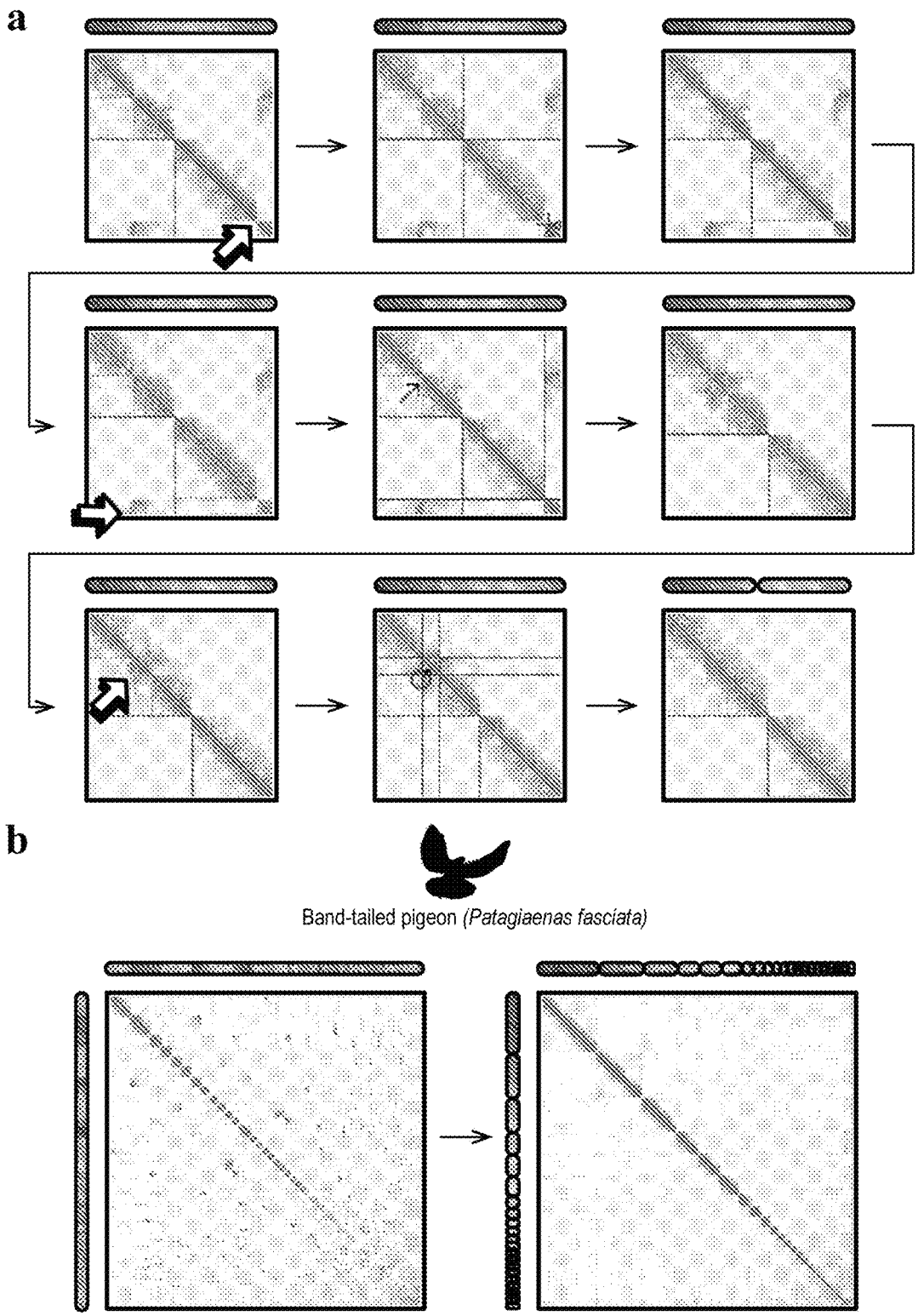
FIG. 61—Illustrates interactive genome assembly for the band-tail pigeon.
Figure 62:
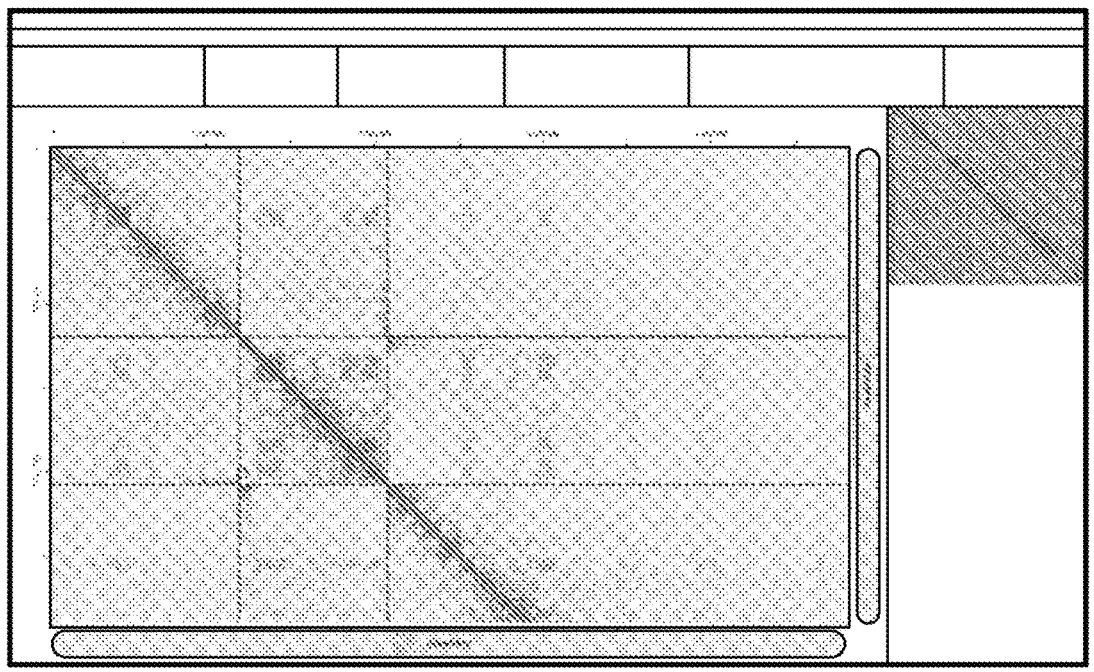
FIG. 62—Shows de novo assembly of three different species: the common wombat (*Vombatus ursinus*), Virginia opossum (*Didelphis virginiana*), and the common raccoon (*Procyon lotor*).
Figure 62:
Figure 62:
Figure 62:
Figure 62:
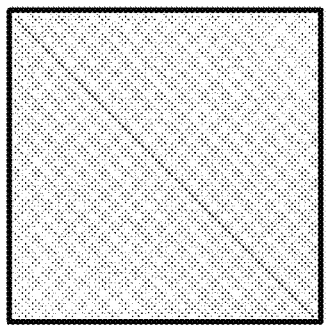
Figure 62:
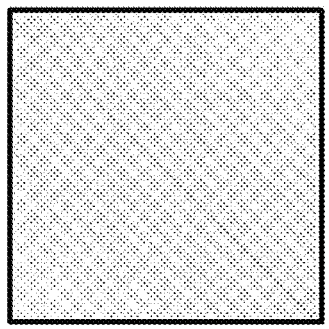
Figure 62:
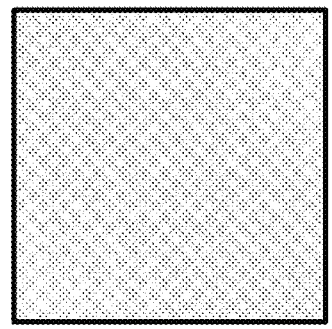
Figure 62:
Figure 62:
Figure 62:
Figure 62:
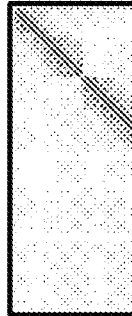
Figure 62:
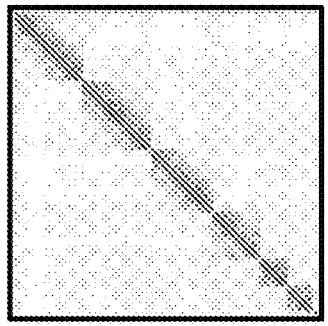
Figure 63:
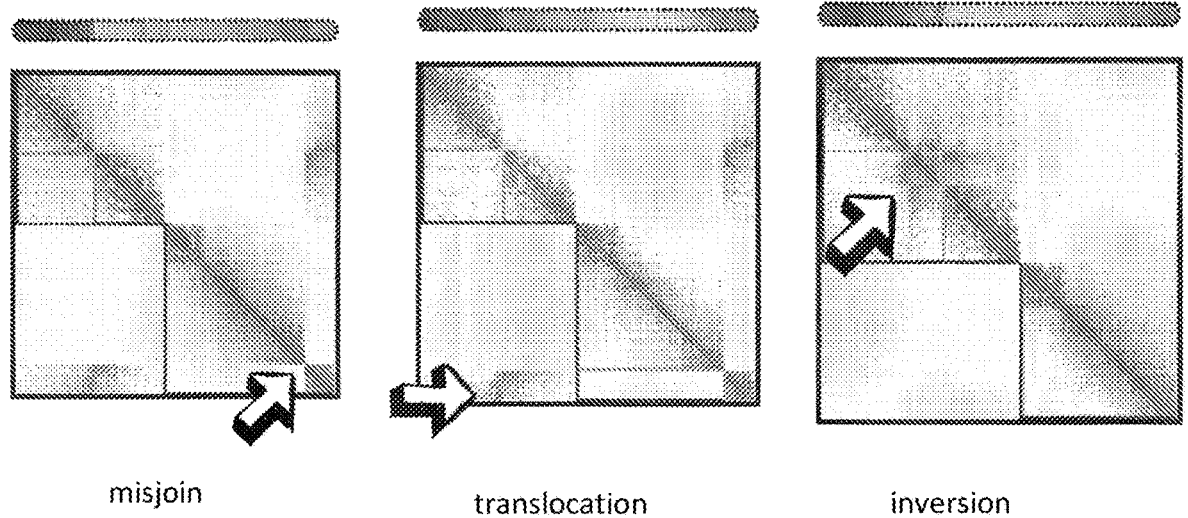
FIG. 63—show how misjoins, translocations, and inversions can be visualized on a Hi-C heatmap.
Figure 64:
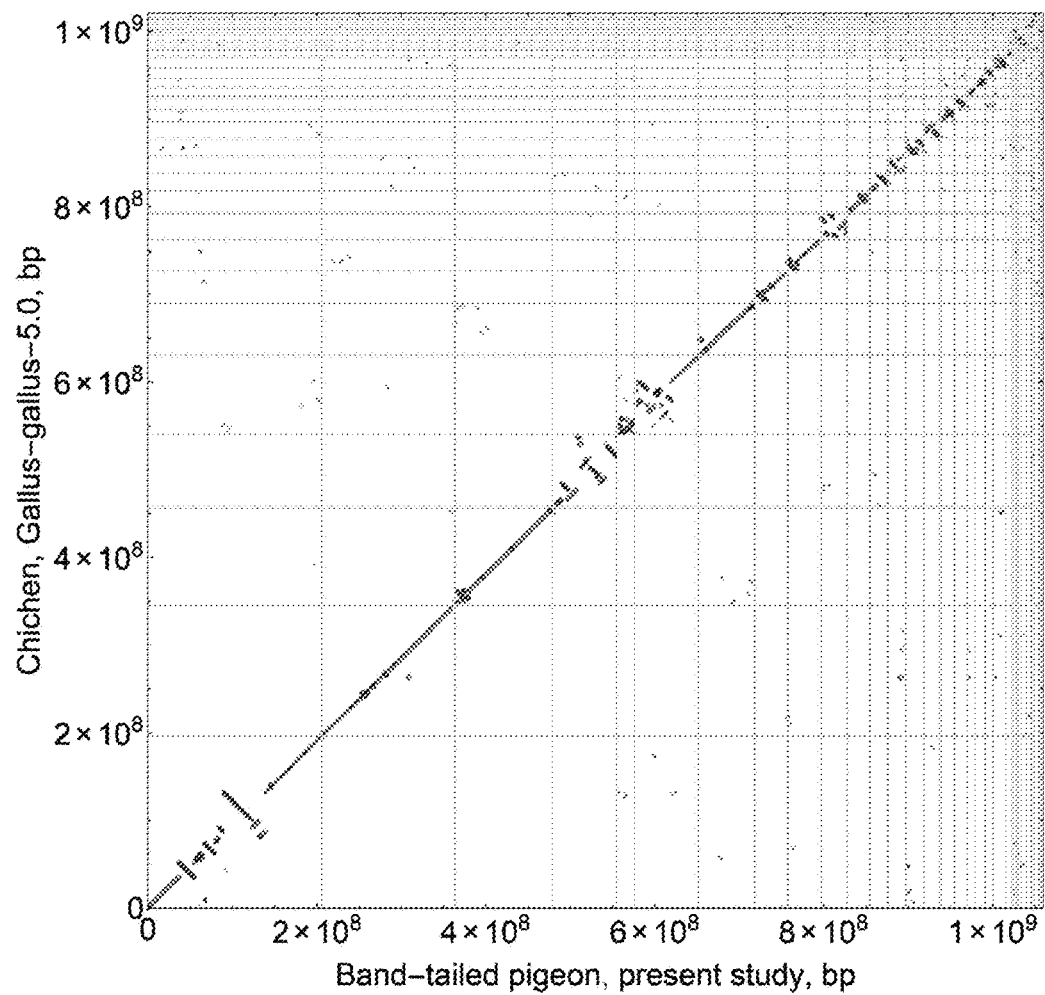
FIG. 64—The genome assembly for the band-tailed pigeon was created in this study to analyze synteny between the pigeon and the chicken. Applicant observed strong conservation of synteny between both species, including nearly perfect conservation of synteny between several pairs of chromosome-length scaffolds as well as several large-scale rearrangements. For this analysis, the chicken genome assembly (GCF_000002315.4) and the band-tailed pigeon fastas were aligned using the LastZ alignment algorithm (Robert S. Harris 2007) using "—notransition—step=20-nogapped" command options; the chicken assembly was used as a target. Here, alignment blocks with scores larger than 25,000 (Robert S. Harris 2007), are shown with direct synteny blocks colored red, and inverted blocks colored blue. Chromosome order and orientation has been modified in order to facilitate the comparison.
Figure 65:
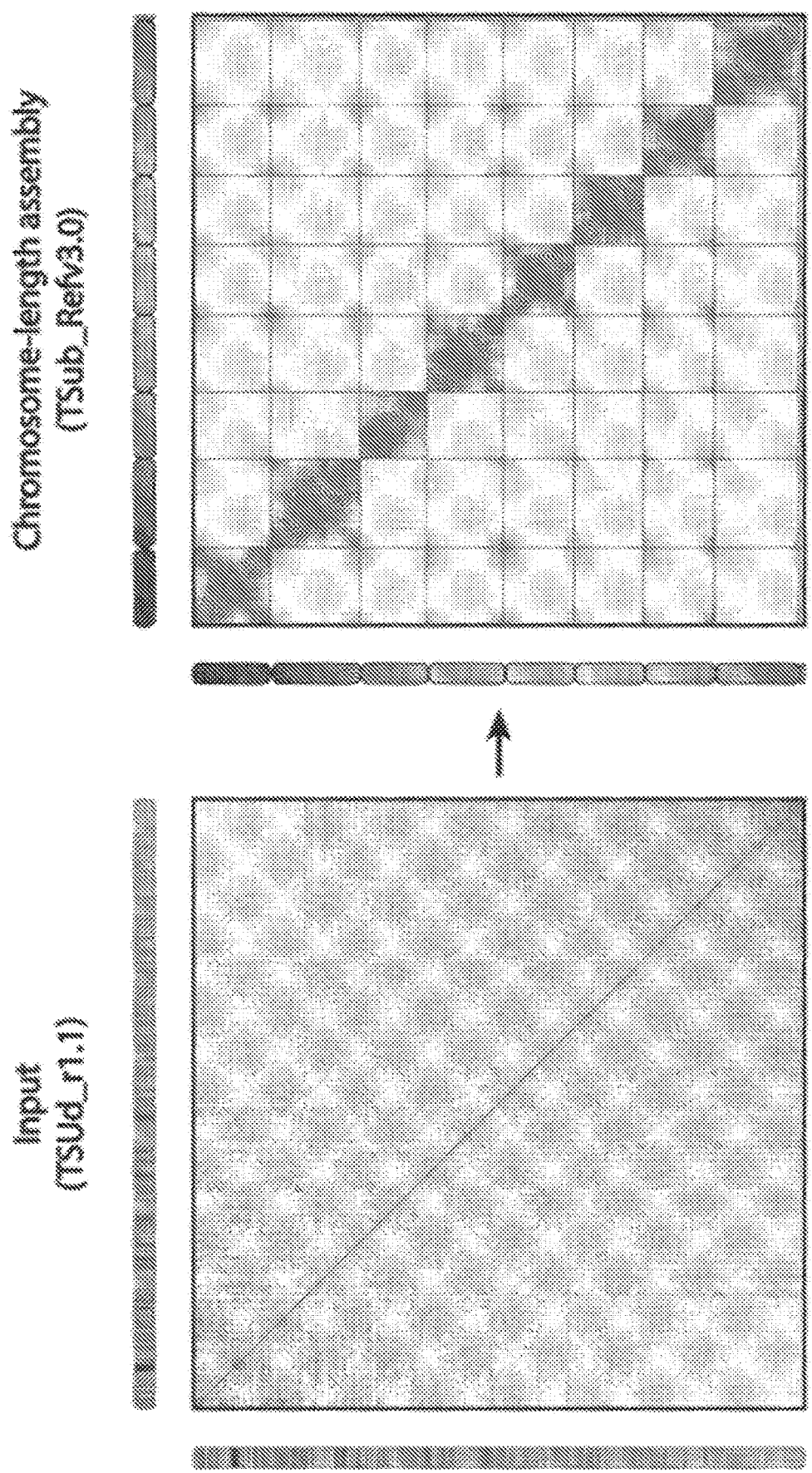
FIG. 65—shows a genome assembly, in accordance of certain example embodiments, of subterranean clover *T. subterraneum*.
Figure 66:
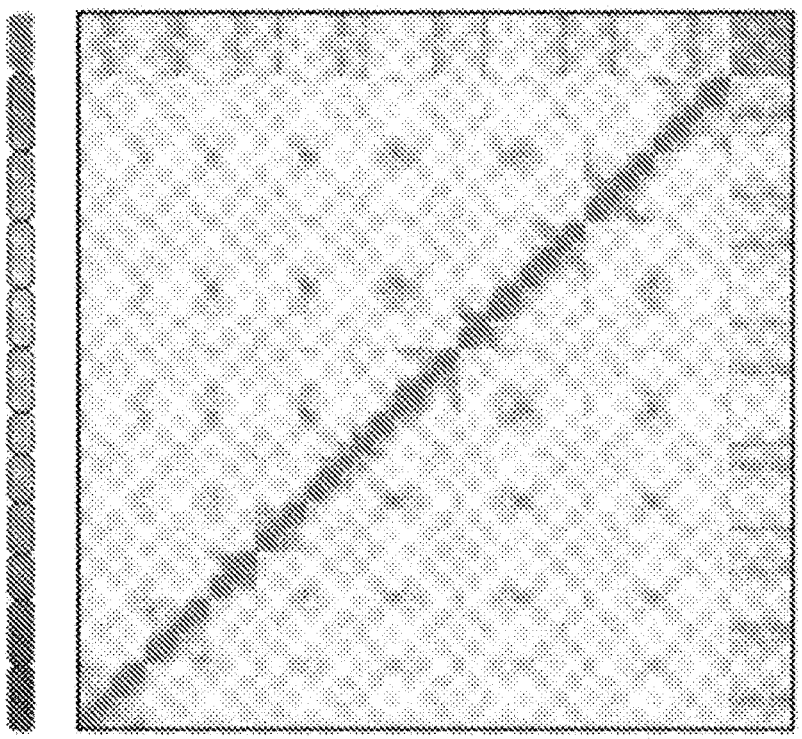
FIG. 66—shows a genome assembly, in accordance with certain example embodiments, of pigeon pea *Cajanus cajan*.
Figure 66:
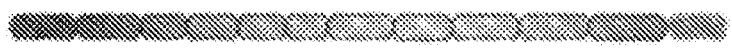
Figure 66:
Figure 66:
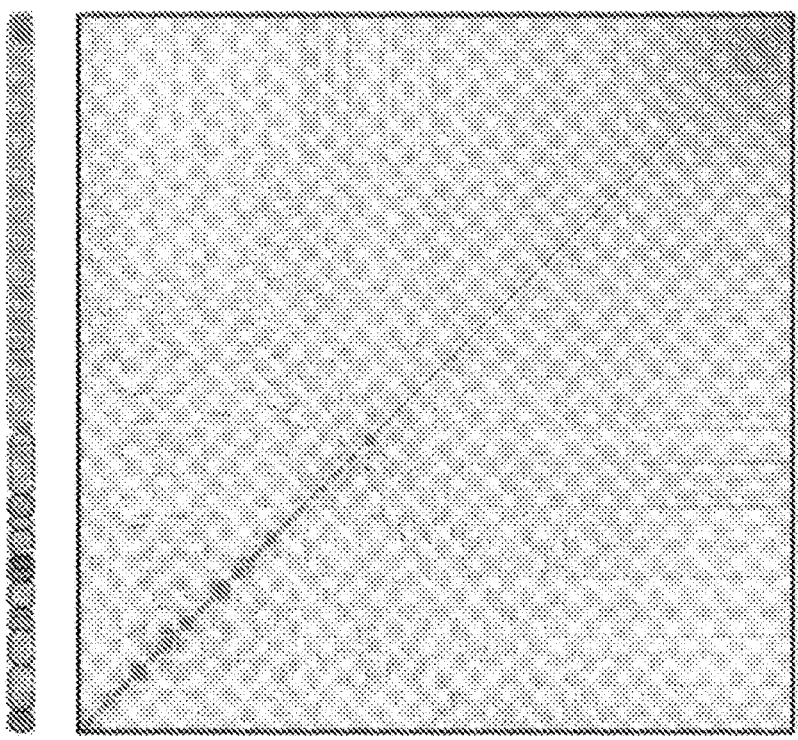
Figure 66:
Figure 67:
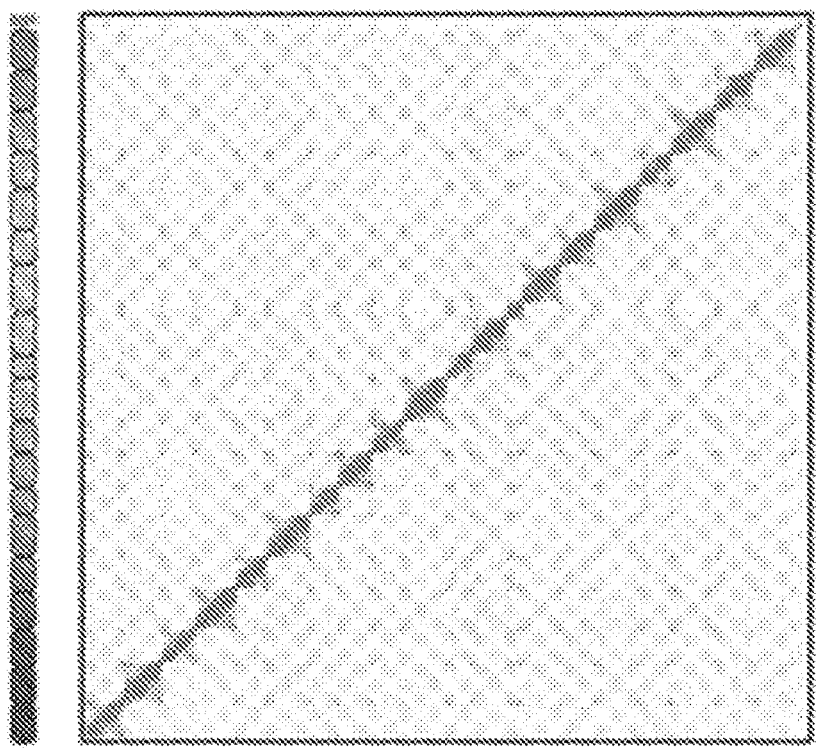
FIG. 67—shows a genome assembly, in accordance with certain example embodiments of tetraploid peanut *Arachis hypogaea*.
Figure 67:
Figure 67:
Figure 67:
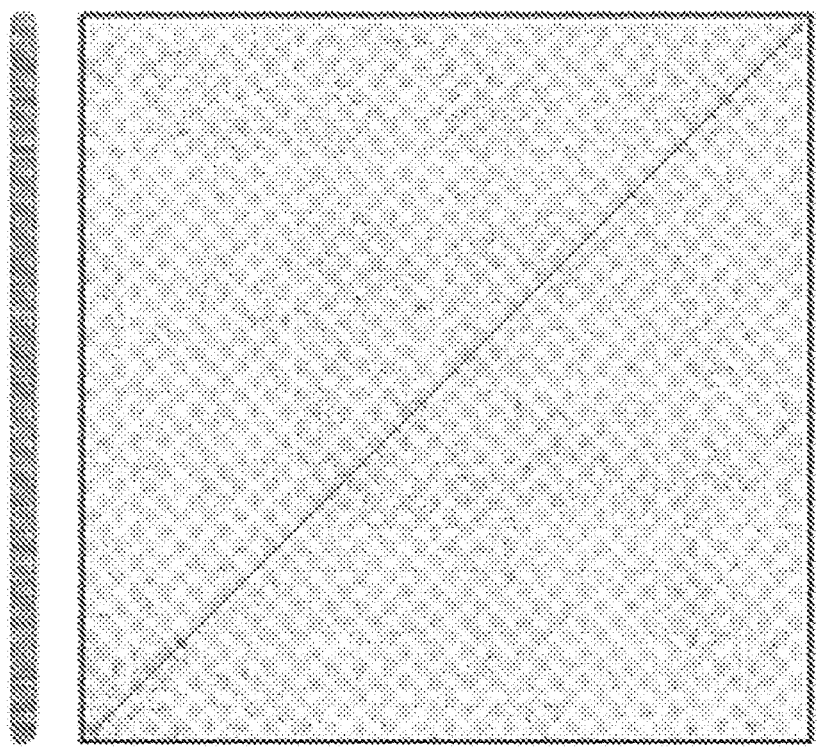
Figure 67:
Figure 68:
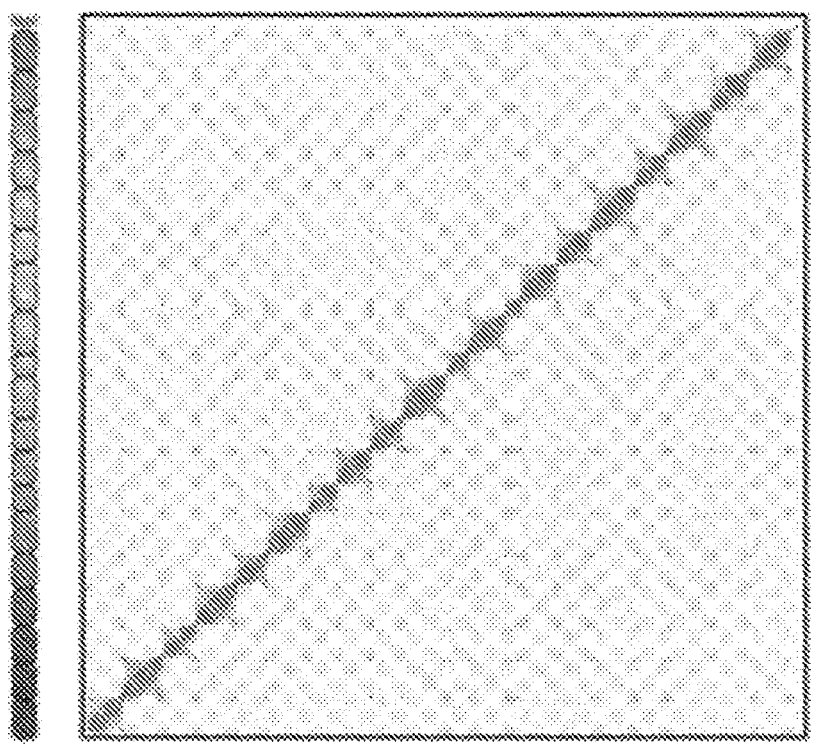
FIG. 68—shows a genome assembly, in accordance with certain example embodiments of chickpea, *Cicer arietnum*.
Figure 68:
Figure 68:
Figure 68:
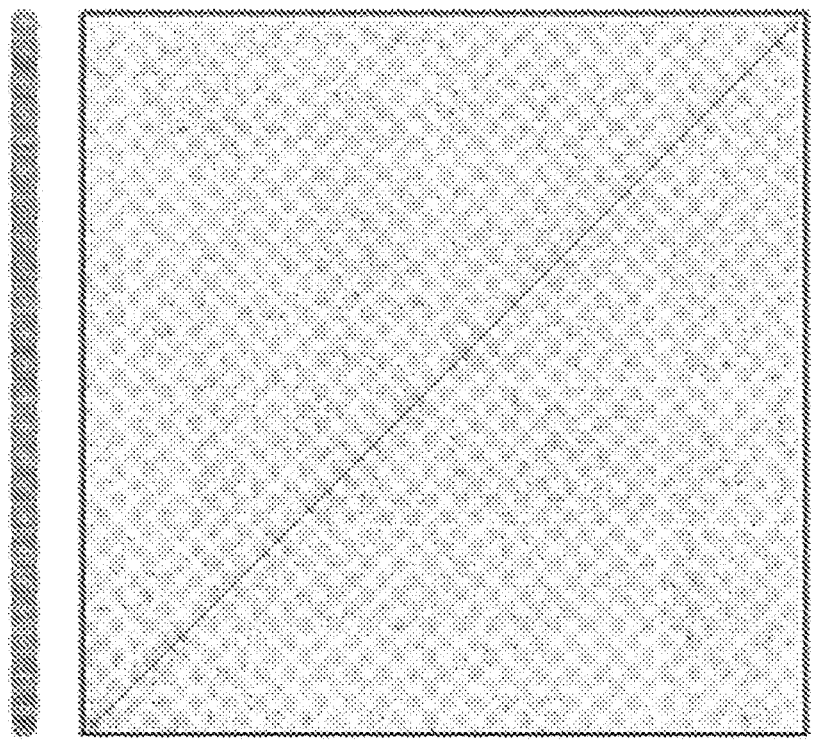
Figure 68:
Figure 69:
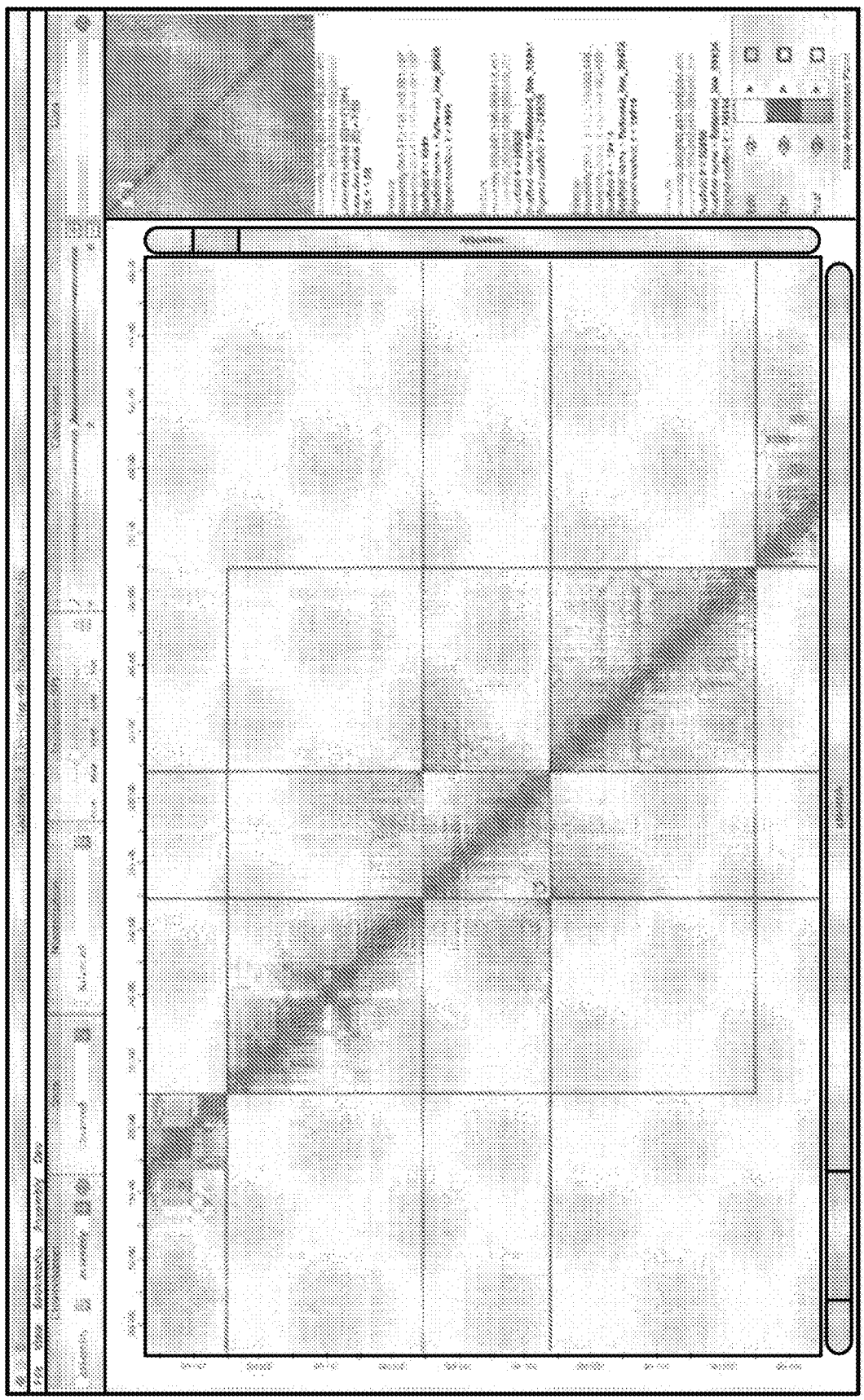
FIG. 69—provide an example Assembly Tools GUI in accordance with certain example embodiments.

While using the Assembly Tools module with Juicebox, users can also continue to employ standard Juicebox functions (see FIG. 57); for instance, they can modify the color scale, view 1D tracks, or zoom in and out (Durand, Shamim, et al. 2016). When finished, a user can save the results as a new .assembly file. After exiting Juicebox, a simple script can be run from the command line in order to apply this assembly file to the original reference assembly fasta file, producing an error-corrected assembly sequence.

To illustrate interactive genome assembly, Applicant re-examined data from a very recent study which assembled the genome of the band-tail pigeon, the closest living relative of the extinct passenger pigeon (Murray et al. 2017). This assembly incorporated Illumina and in vitro Hi-C (Chicago), yielding a scaffold N50 of 20 Mb. Applicant generated in situ Hi-C data for the band-tailed pigeon (239M read pairs, 66× coverage). Applicant then placed the extant scaffolds in random order, loaded them into Juicebox, and performed an interactive genome assembly, resulting in chromosome-length scaffolds (scaffold N50: 76 Mb). (See FIG. 56.)

To validate this assembly, Applicant aligned it to the chromosome-length scaffolds of the chicken genome (International Chicken Genome Sequencing Consortium 2004). Applicant observed strong conservation of synteny between both species, including nearly perfect conservation of synteny between several pairs of chromosome-length scaffolds (see Supplemental Online Materials). Applicant also observed several large inversions and rearrangements, consistent with the substantial evolutionary distance between the two species (~70M years, (Prum et al. 2015)).

Although the Assembly Tools module can be used independently, it can also be used as a validation and refinement system for our automated 3D-DNA pipeline, which uses Hi-C data to improve genome assemblies. This is accomplished by taking the output of 3D-DNA and manually exploring it using Assembly Tools in order to identify and remove any remaining assembly errors. This has two advantages as compared to the use of 3D-DNA alone. First, even when the goal is to assemble a single genome, automated Hi-C-based assembly algorithms are typically run over-and-over, sweeping across a wide array of input parameter settings in order to identify a reliable parameter setting for that particular genome (Bickhart et al. 2017). By performing manual validation and refinement using Assembly Tools, it is often possible to run 3D-DNA using default parameters and get a reliable final assembly regardless of the genome being examined. Second, by adding a manual validation and refinement step, reliable genome assemblies can often be generated using less input data, reducing the cost of de novo genome assembly.

To illustrate the use of 3D-DNA methods, such as those disclosed herein, and Assembly Tools in tandem, Applicant developed a procedure for assembling mammalian genomes with chromosome-length scaffolds for under $1000. Applicant's procedure involves three steps, and can be performed by a single person in roughly 10 days. First, Applicant generated a PCR-free DNA-Seq library, and sequence 300 million 150 bp paired-end reads. This corresponds to roughly 30× coverage for a typical (3 Gb) mammal. These reads are assembled into a draft assembly using the software package w2rap (B. Clavijo et al. 2017; B. J. Clavijo et al. 2017). Second, an in situ Hi-C library is generated (Rao et al. 2014), and 100 million 150 bp paired-end reads are sequenced, corresponding to roughly 10× coverage for a typical mammal. These are used to improve the draft assembly by providing both as inputs to 3D-DNA (Dudchenko et al. 2017). Finally, the improved assembly is validated and refined using Assembly Tools. Note that this procedure does not require advance knowledge of the exact size of the mammalian genome, or of the number of chromosomes.

To confirm the accuracy of the resulting genomes, Applicant used the procedure to generate a de novo assembly of a human genome (the GM12878 cell line). The resulting assembly, Hs-1K, contains 23 chromosome-length scaffolds which together span 88,735 contigs (contig N50: 36,914) and 2,399,853,403 sequenced bases, comprising 85.2% of the genome assembly. It also contains 1,169 small scaffolds, spanning 1,652 contigs (contig N50: 21,506) and 397,814,093 bases, comprising the remaining 14.1% of the assembly. These small scaffolds contain contigs that could not be positioned reliably using Hi-C data, typically because they were very short.

Comparison of Hs-1K with the human genome reference, hg38, showed that the 23 chromosome-length scaffolds in Hs-1K correctly corresponded to the 23 human chromosomes, with 98.46% of sequenced bases on chromosome-length scaffolds assigned to the correct chromosome. Together, the chromosome-length scaffolds in Hs-1K spanned 83.26% of the length and 82.435% of the sequence in the chromosome-length scaffolds of hg38.

Next Applicant examined the accuracy of the ordering of these chromosome-length scaffolds. When pairs of draft scaffolds assigned to the same chromosome were examined, the order in Hs-1K matched the order in hg38. As scaffold length increases an increase in matching accuracy was observed, with most errors arising from shorter scaffolds.

Having validated the above assembly procedure, Applicant repeated it in order to generate de novo assemblies of three mammals for which no sequence data has been published to date: the common wombat, *Vombatus ursinus*, the Virginia opossum, *Didelphis virginiana*, and the raccoon, *Procyon lotor*. In each case, the result was a set of chromosome length scaffolds: for wombat, the procedure generated 7 chromosome-length scaffolds, spanning 83.7% of the sequenced bases, with a total length of 2.72 Gb; for the Virginia opossum, 11 chromosome-length scaffolds; and for raccoon, 19 chromosome-length scaffolds, spanning 77.6% of sequenced bases, with a total length of 1.94 Gb. (See FIG. 57.)

Taken together, these findings demonstrate that the embodiments disclosed herein can be reliably employed in order to generate de novo assemblies of mammalian genomes with chromosome-length scaffolds.

It is interesting to compare the costs of the de novo genome assembly strategy described above to the cost of human genome re-sequencing, in which short DNA-Seq reads from an individual are compared to the existing human reference genome. Illumina's HiSeqX platform demonstrated that human genome re-sequencing could be achieved for under $1000 by using a strategy that achieved ~40× coverage of the human genome by means of 400 million 150 bp paired-end DNA-Seq reads (llumina, Inc. 2016). The de novo genome assembly strategy described above uses extremely similar inputs, simply replacing 100 million of the 400 million paired-end DNA-Seq reads with in situ Hi-C reads. Thus, Applicant's approach enables de novo assembly of mammalian genomes for under $1000. The same approach could also be used to generate individualized human genomes.

The genome assemblies generated using the strategy Applicant describes may be further improved. For example, it would be valuable to incorporate additional sequence into the chromosome-length scaffolds, and to thereby fill gaps. It is also possible to improve the genomes by correcting errors in the fine-scale ordering of small adjacent contigs. Issues, such as difficulties in correctly orienting genomic intervals separated by extremely large gaps, such as chromosome arms separated by very large centromeres, can be alleviated by additional short-read Illumina data. More expensive data types, such as long-read DNA sequences, can also be employed to further improve the genome assembly. Applicant provides examples for a variety of such use cases in Table 1.

TABLE 1

More expensive data types can be employed together with Hi-C to generate chromosome-length assemblies with larger percentage of sequenced bases in chromosome-length assemblies. Here we compare the results of the 3d-dna plus Assembly Tools strategy to generate chromosome-length human genomes from ~27X of PCR-free PE150 DNA-seq data (current study, reads subsampled from ftp-trace.ncbi.nlm.nih.gov/giab/ftp/data/NA12878/NIST__NA12878__HG001__HiSeq__300x/); ~60X of PCR-free PE250, downloaded from Sequence Read Archive (SRX297987); a recent draft genome assembly using Oxford Nanopore reads (Jain et al. 2017); and a high-quality draft from Pacific Biosciences long-read technology GCA__002077035.2.

| 7X Hi-C + contiger | PE150 (~$1K) w2rap | PE250 (~$7K)*** discovar | ONT ($50-100K) canu | PB ($50-100K) falcon |
|---|---|---|---|---|
| Draft, total seq bases (>1K) | 2,712,354,371 | 2,819,306,710 | 2,646,010,004 | 2,858,827,405 |
| Draft, number of contigs | 164,715 | 80,223 | 2,886 | 3,628 |
| Draft, contig n50 | 32,574 | 102,922 | 3,620,647 | 14,520,880 |
| Draft, contig ng50* | 28,415 | 102,922 | 3,024,148 | 13,176,815 |
| Draft, total length of scaffolds | 2,717,536,071 | 2,819,952,110 | 2,646,010,004 | 2,858,827,405 |
| Draft. number of scaffolds | 112,925 | 73,770 | 2,886 | 3,628 |
| Draft, scaffold n50 | 77,994 | 125,775 | 3,620,647 | 14,520,880 |
| Draft, scaffold ng50* | 67,475 | 115,268 | 3,024,148 | 13,176,815 |
| Chom-length total seq bases | 2,399,853,403 | 2,654,127,695 | 2,603,945,898 | 2,780,087,239 |
| Chrom-length number of contigs | 88,735 | 36,616 | 2,441 | 1,200 |
| Chrom-length contig n50 | 36,914 | 108,937 | 3,517,161 | 14,518,630 |
| Chrom-length contig ng50* | 28,200 | 93,928 | 2,935,826 | 14,518,630 |
| Chr-length total length of scaffolds | 2,423,876,603 | 2,669,861,395 | 2,605,154,898 | 2,780,675,739 |
| Chrom-length number of scaffolds | 23 | 23 | 23 | 23 |
| Chrom-length scaffolds n50** | 125,170,150 | 141,244,516 | 138,911,586 | 149,363,931 |
| Chrom-length scaffold ng50*,** | 114,962,098 | 136,507,704 | 133,352,303 | 141,190,470 |
| All output, total seq bases | 2,712,354,371 | 2,819,306,710 | 2,646,010,004 | 2,858,827,405 |
| All output, number of contigs | 165,597 | 80,725 | 3,749 | 4,668 |
| All output, contig n50 | 32,499 | 102,793 | 3,490,673 | 13,912,961 |
| All output, contig ng50 | 28,350 | 93,976 | 2,935,826 | 47,391,326 |

TABLE 1-continued

More expensive data types can be employed together with Hi-C to generate chromosome-length assemblies with larger percentage of sequenced bases in chromosome-length assemblies. Here we compare the results of the 3d-dna plus Assembly Tools strategy to generate chromosome-length human genomes from ~27X of PCR-free PE150 DNA-seq data (current study, reads subsampled from ftp-trace.ncbi.nlm.nih.gov/giab/ftp/data/NA12878/NIST_NA12878_HG001_HiSeq_300x/); ~60X of PCR-free PE250, downloaded from Sequence Read Archive (SRX297987); a recent draft genome assembly using Oxford Nanopore reads (Jain et al. 2017); and a high-quality draft from Pacific Biosciences long-read technology GCA_002077035.2.

| 7X Hi-C + contiger | PE150 (~$1K) w2rap | PE250 (~$7K)*** discovar | ONT ($50-100K) canu | PB ($50-100K) falcon |
|---|---|---|---|---|
| All output, total length of scaffolds | 2,736,505,371 | 2,835,055,510 | 2,647,366,504 | 2,859,645,405 |
| All output, number of scaffolds | 75,863 | 44,065 | 1,036 | 3,032 |
| All output, scaffolds n50** | 125,170,150 | 141,244,516 | 138,911,586 | 149,363,931 |
| All output, scaffold ng50*,** | 114,962,098 | 136,507,704 | 133,352,303 | 141,190,470 |
| % of draft assembly | 88.48% | 94.14% | 98.41% | 97.25% |
| % of hg38 chrom seq bases | 82.43% | 91.17% | 89.45% | 95.50% |
| % of IHGSC 2001 chrom seq bases | 90.33% | 99.90% | 98.01% | 104.64% |
| % of 10 kb chunks correctly anchored | 99.88% | 99.83% | 99.93% | 99.91% |
| % of 10 kb chunks correctly ordered, random | 99.73% | 99.13% | 99.83% | 99.76% |
| % of 10 kb chunks correctly ordered adjacent | 94.95% | 95.73% | 99.10% | 99.40% |
| % of correctly oriented 10 kb chunks | 94.82% | 95.58% | 99.06% | 99.33% |

Material for the mammalian samples described in this study has been collected in the Houston Zoo by performing three opportunistic blood draws, secondary to veterinary and/or husbandry procedures scheduled to maintain health and welfare of the animals. The blood draw (~1 ml) was split in two to prepare DNA-seq and Hi-C libraries. For the DNA-seq library, we extracted DNA using Quiagen DNeasy Mini Blood & Tissue Kit, following the manufacturer's protocols. The DNA was sheared and prepared for Illumina sequencing using the TruSeq DNA PCR-Free kit, following the manufacturer's protocols. For Hi-C, peripheral blood mononuclear cells were separated using a Percoll gradient. The cells were crosslinked and in situ Hi-C libraries were prepared in accordance with (Rao et al. 2014). The band-tailed pigeon sample (frozen liver) was provided by the Wildlife Conservation Society. Tissue was crosslinked and dounce homogenized. Nuclei were purified on a sucrose gradient and processed to prepare in situ Hi-C libraries as previously described (Rao et al. 2014).

|  | Common wombat | Virginia opossum | Common raccoon | Band-tailed pigeon |
|---|---|---|---|---|
| Binomial: | Vombatus ursinus | Didelphis virginiana | Procyon lotor | Patagioenas fasciata |
| Isolate: | Lilly | Luna | Gracie | N2016-0142 |
| Sex: | Female | Female | Female | Male |
| Source: | Houston Zoo | Houston Zoo | Houston Zoo | WCS |
| Tissue type: | Blood | Blood | Blood | Liver |
| Amount: | 2 ml | 0.75 ml | 0.75 ml | 10 mg |
| Notes: | — | leucism, wild caught | — | hatchling |

Finally, Applicant note that this methodology is not restricted to mammals, and can be applied successfully to many other clades. Depending on the size of the genome of interest, more or less input data may be required.

REFERENCES

A. Harmon, Team of Rival Scientists Comes Together to Fight Zika. N. Y. Times (2016).
S. Gnerre et al., High-quality draft assemblies of mammalian genomes from massively parallel sequence data. Proc. Natl. Acad. Sci. 108, 1513-1518 (2011).
L. J. S. Williams et al., Paired-end sequencing of Fosmid libraries by Illumina. Genome Res. 22, 2241-2249 (2012).
E. Lieberman-Aiden et al., Comprehensive mapping of long-range interactions reveals folding principles of the human genome. Science. 326, 289-293 (2009).
S. S. P. Rao et al., A 3D map of the human genome at kilobase resolution reveals principles of chromatin looping. Cell. 159, 1665-1680 (2014).
N. Kaplan, J. Dekker, High-throughput genome scaffolding from in vivo DNA interaction frequency. Nat. Biotechnol. 31, 1143-1147 (2013).
H. Marie-Nelly et al., High-quality genome (re)assembly using chromosomal contact data. Nat. Commun. 5, 5695 (2014).
C. L. Peichel, S. T. Sullivan, I. Liachko, M. A. White, Improvement of the threespine stickleback (Gasterosteus aculeatus) genome using a Hi-C-based Proximity-Guided Assembly method. bioRxiv, 068528 (2016).
N. H. Putnam et al., Chromosome-scale shotgun assembly using an in vitro method for long-range linkage. Genome Res. (2016), doi:10.1101/gr.193474.115.
J. N. Burton et al., Chromosome-scale scaffolding of de novo genome assemblies based on chromatin interactions. Nat. Biotechnol. 31, 1119-1125 (2013).
D. M. Bickhart et al., Single-molecule sequencing and conformational capture enable de novo mammalian reference genomes. bioRxiv, 064352 (2016).
A. M. Session et al., Genome evolution in the allotetraploid frog Xenopus laevis. Nature. 538, 336-343 (2016).
R. R. Love, N. I. Weisenfeld, D. B. Jaffe, N. J. Besansky, D. E. Neafsey, Evaluation of DISCOVAR de novo using a mosquito sample for cost-effective short-read genome assembly. BMC Genomics. 17, 187 (2016).
E. S. Lander et al., Initial sequencing and analysis of the human genome. Nature. 409, 860-921 (2001).
J. C. Venter et al., The Sequence of the Human Genome. Science. 291, 1304-1351 (2001).
M. Pendleton et al., Assembly and diploid architecture of an individual human genome via single-molecule technologies. Nat. Methods. 12, 780-786 (2015).
D. B. Jaffe et al., Whole-genome sequence assembly for mammalian genomes: Arachne 2. Genome Res. 13, 91-96 (2003).

V. Nene et al., Genome sequence of *Aedes aegypti*, a major arbovirus vector. *Science.* 316, 1718-1723 (2007).

P. Junej a et al., Assembly of the genome of the disease vector *Aedes aegypti* onto a genetic linkage map allows mapping of genes affecting disease transmission. *PLoS Negl. Trop. Dis.* 8, e2652 (2014).

P. Arensburger et al., Sequencing of *Culex quinquefasciatus* establishes a platform for mosquito comparative genomics. *Science.* 330, 86-88 (2010).

P. V. Hickner, A. Mori, D. D. Chadee, D. W. Severson, Composite linkage map and enhanced genome map for *Culex pipiens* complex mosquitoes. *J. Hered.* 104, 649-655 (2013).

N. C. Durand et al., Juicer Provides a One-Click System for Analyzing Loop-Resolution Hi-C Experiments. *Cell Syst.* 3, 95-98 (2016).

N. C. Durand et al., Juicebox Provides a Visualization System for Hi-C Contact Maps with Unlimited Zoom. *Cell Syst.* 3, 99-101 (2016).

M. R. Hubner, D. L. Spector, Chromatin Dynamics. *Annu. Rev. Biophys.* 39, 471-489 (2010).

M. A. Ferguson-Smith, V. Trifonov, Mammalian karyotype evolution. *Nat. Rev. Genet.* 8, 950-962 (2007).

A. L. Sanborn et al., Chromatin extrusion explains key features of loop and domain formation in wild-type and engineered genomes. *Proc. Natl. Acad. Sci.* 112, E6456-E6465 (2015).

O. Tange, GNU Parallel: The Command-Line Power Tool. *Login USENIX Mag.* 36 (2011), pp. 42-47.

Robert S. Harris, thesis, The Pennsylvania State University (2007).

J. B. Kruskal, On the Shortest Spanning Subtree of a Graph and the Traveling Salesman Problem. *Proc. Am. Math. Soc.* 7, 48-50 (1956).

J. P. Vinson et al., Assembly of polymorphic genomes: algorithms and application to Ciona savignyi. *Genome Res.* 15, 1127-1135 (2005).

C.-S. Chin et al., Phased diploid genome assembly with single-molecule real-time sequencing. *Nat. Methods.* 13, 1050-1054 (2016).

E. M. Darrow et al., Deletion of DXZ4 on the human inactive X chromosome alters higher-order genome architecture. *Proc. Natl. Acad. Sci.* 113, E4504-E4512 (2016).

N. I. Weisenfeld et al., Comprehensive variation discovery in single human genomes. *Nat. Genet.* 46, 1350-1355 (2014).

H. Li, R. Durbin, Fast and accurate short read alignment with Burrows-Wheeler transform. *Bioinformatics.* 25, 1754-1760 (2009).

H. Cao et al., Rapid detection of structural variation in a human genome using nanochannel-based genome mapping technology. *Giga Science.* 3, 34 (2014).

V. A. Timoshevskiy et al., Genomic composition and evolution of *Aedes aegypti* chromosomes revealed by the analysis of physically mapped supercontigs. *BMC Biol.* 12, 27 (2014).

M. F. Unger, M. V. Sharakhova, A. J. Harshbarger, P. Glass, F. H. Collins, A standard cytogenetic map of *Culex quinquefasciatus* polytene chromosomes in application for fine-scale physical mapping. *Parasit. Vectors.* 8, 307 (2015).

A. N. Naumenko et al., Correction: Mitotic-Chromosome-Based Physical Mapping of the *Culex quinquefasciatus* Genome. *PloS One.* 10, e0127565 (2015).

G. I. Giraldo-Calderon et al., VectorBase: an updated bioinformatics resource for invertebrate vectors and other organisms related with human diseases. *Nucleic Acids Res.* 43, D707-713 (2015).

A. Yates et al., Ensembl 2016. *Nucleic Acids Res.* 44, D710-D716 (2016).

N. Varoquaux et al., Accurate identification of centromere locations in yeast genomes using Hi-C. *Nucleic Acids Res.* 43, 5331-5339 (2015).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method for generating an error-corrected genome assembly for an organism, comprising:
    a) performing whole genome sequencing on one or more samples from the organism or closely related species, wherein a reference assembled genome is generated from the sequencing contains gaps in adjacent contigs or a scaffold;
    b) performing a DNA proximity ligation assay on one or more samples from the organism or closely related species and generating a genomic contact map derived from the DNA proximity ligation assay conducted on the one or more samples from the organism or a related species;
    c) superimposing the positions of adjacent contigs or scaffolds from the reference assembled genome derived from the whole genome sequencing of one or more samples from the organism on top of the genomic contact map using computer software, wherein computer software comprises using a density graph;
    d) correcting errors in the reference assembled genome through a computer user interface, wherein correcting errors comprises incorporating sequences from the genomic contact map derived from the DNA proximity ligation assay thereby filling the gaps in the reference assembled genome, to obtain a corrected assembly file, wherein errors in the reference assembled genome are visualized by observing aberrant contacts in the genomic contact map; and
    e) generating an error corrected genome assembly data file, wherein the error corrected genome assembly is the final permutated reference assembled genome.

2. The method of claim 1, wherein the DNA proximity ligation assay is Hi-C.

3. The method of claim 1, wherein the reference assembled genome is generated using short-read sequencing technology, long-read sequencing technology, insert clones, linkage mapping data, physical mapping data, optical mapping date, or a combination thereof.

4. The method of claim 1, wherein observing aberrant contacts in the genomic contact map is based, at least in part, on the frequency of contacts between one part of a contig or scaffold and other parts of the same contig or scaffold, or based on the frequency of contact between one part of a contig or scaffold and other contigs and scaffolds, or a combination thereof.

5. The method of claim 4, wherein the aberrant contacts are misjoins, rearrangements, translocations, inversions, insertion, deletions, repeats, alignment errors, due to features of how the genome folds in three dimensions, cyclic permutations of the chromosomes, or a combination thereof.

6. The method of claim 5, wherein the translocations are balanced translocations, unbalanced translocations, or a combination thereof.

7. The method of claim 5, wherein the repeats are tandem repeats.

8. The method of claim 5, wherein a misjoin comprises a point along the diagonal of the contact map, a translocation comprises an extremely bright arrowhead motif pointing towards the diagonal of the contact map, and an inversion comprises two arrowhead motifs pointing at one another.

9. The method of claim 1, wherein the organism is an animal or a plant.

* * * * *

UNITED STATES PATENT AND TRADEMARK OFFICE
CERTIFICATE OF CORRECTION

| | | |
|---|---|---|
| PATENT NO. | : 12,027,236 B2 | Page 1 of 1 |
| APPLICATION NO. | : 16/247502 | |
| DATED | : July 2, 2024 | |
| INVENTOR(S) | : Aiden et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1031 days.

Signed and Sealed this
Third Day of December, 2024

Katherine Kelly Vidal
*Director of the United States Patent and Trademark Office*